United States Patent [19]
Mochizuki et al.

[11] Patent Number: 5,856,334
[45] Date of Patent: Jan. 5, 1999

[54] IMIDAZOQUINOLINE DERIVATIVES

[75] Inventors: Hidenori Mochizuki; Kazuo Kato; Ichiro Yamamoto; Kiyoshi Mizuguchi, all of Tokyo, Japan

[73] Assignee: Mochida Pharmaceutical Co., Ltd., Tokyo, Japan

[21] Appl. No.: 776,435

[22] PCT Filed: Nov. 10, 1994

[86] PCT No.: PCT/JP94/01900

§ 371 Date: Jan. 28, 1997

§ 102(e) Date: Jan. 28, 1997

[87] PCT Pub. No.: WO96/04279

PCT Pub. Date: Feb. 15, 1996

[30] Foreign Application Priority Data

Jul. 29, 1994 [JP] Japan .................................. 6-178824

[51] Int. Cl.$^6$ ...................... C07D 471/06; C07D 471/04; A61K 31/435; A61K 31/44
[52] U.S. Cl. .............................. 514/292; 546/81; 546/86; 546/87; 546/88
[58] Field of Search ................. 546/86, 87, 81, 546/85; 514/292

[56] References Cited

U.S. PATENT DOCUMENTS

| | | | |
|---|---|---|---|
| 3,200,123 | 8/1965 | Richardson, Jr. et al. | 260/288 |
| 5,151,431 | 9/1992 | Inaba et al. | 514/292 |
| 5,212,186 | 5/1993 | Paal et al. | 514/338 |

FOREIGN PATENT DOCUMENTS

| | | | |
|---|---|---|---|
| 0386722A1 | 9/1990 | European Pat. Off. | C07D 471/04 |
| 0638570A1 | 2/1995 | European Pat. Off. | C07D 471/06 |
| 4027592A1 | 3/1992 | Germany . | |
| A327382 | 2/1991 | Japan | C07D 471/06 |
| WO9322313 | 11/1993 | WIPO | C07D 471/06 |

OTHER PUBLICATIONS

Peet et al., "Synthesis and Antiallergic Activity of Some Quinolinones and Immidazoquinolinones", *J. Med. Chem.,* vol. 28, pp. 298–302, 1985.

Richardson, Jr., et al., "Study off the Synthesis and Chemistry of thhe 5,6–Dihydroimidazo[ij]quinoline Series", *Journal of Organic Chemistry,* vol. 25, pp. 1138–1147, 1960.

*Primary Examiner*—Jose G. Dees
*Assistant Examiner*—Sabiha N. Qazi
*Attorney, Agent, or Firm*—Birch, Stewart, Kolasch & Birch LLP

[57] ABSTRACT

Specified imidazoquinoline derivatives represented by the formula (I):

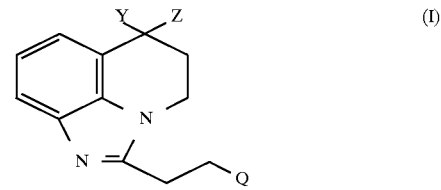

(I)

where Q represents an optionally substituted phenyl, pyridyl or furyl group; Y represents either a hydrogen atom or, when taken together with Z, an oxygen atom and a methylene group; Z represents a hydrogen atom, a hydroxymethyl group, a carboxymethyl group, a 2-oxo-1-pyrrolidinyl group or the following formula (III):

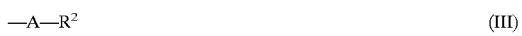

—A—R$^2$     (III)

(where A represents an oxygen atom, a sulfur atom or the group —NH—);

or salts of such derivatives inhibit the increase of eosinophils and are useful as agents for preventing and/or treating diseases that manifest the increase of eosinophils.

10 Claims, 12 Drawing Sheets

1,2,3

4

5

6,11
(+)-form 7,12
(−)-form 8,10
(+)-form 9
(−)-form

13

14

15

71

72

73

74

75

76

77

78

79

80

81

82

83

84

85

86

87

88

89

90

91

92

93

94

107

108

109

110

111

112

113

114

115

116

117

127
(+)-form 128
(-)-form

000000000000
IMIDAZOQUINOLINE DERIVATIVES

This application has been filed under 35 USC 371 as a national stage application of PCT/JP94/01900 filed Nov. 10, 1994.

TECHNICAL FIELD

This invention relates to novel imidazoquinoline derivatives, processes for producing them, and agents, that contain at least one of said imidazoquinoline derivatives as an active ingredient, for preventing and/or treating diseases manifesting the increase of eosinophils.

BACKGROUND ART

Phenomena characterized by the increase of eosinophils in blood or tissues, namely, their differentiation, induction and infiltration, are recognized in many diseases. For clinical purposes, it is important to distinguish between two groups of diseases, those in which the increase of eosinophils is often observed but is not assumed to participate directly in their pathophysiology and those in which eosinophils are believed to participate in their pathophysiology as the primary immunocytes. Diseases of the first group include Addison's disease, ulcerative colitis and the like. Diseases of the second group include verminations, hypereosinophilic syndrome (HES), eosinophilic pneumonia, eosinophilic enterogastritis and the like, as well as bronchial asthma. Eosinophils are closely involved in the pathophysiology of bronchial asthma and the pathophysiological concept, "eosinophilic bronchitis" is becoming established in these days. In particular, the actions of eosinophils participating in the diseases under consideration share several features, that may be summarized as the following three points: 1) accelerated eosinophil production and differentiation by interleukin-5 (IL-5) and other eosinophil growth lymphokines; 2) migration and accumulation of eosinophils in involved organs due to the eosinophil chemotactic activity; and 3) the activation of eosinophils in foci and the extension of their life survival. In the diseases under consideration, these three factors and events are believed to cause eosinophils to exhibit their cytotoxic and inflammation inducing actions, thereby participating in the pathophysiology of the diseases although their lesions, the severity of their clinical symptoms and other factors may vary to some extent [Shigenori Nakajima and Jun'ichi Chihara, Kosankyu no Rinshoshindanjo no Igi (Significance of Eosinophils in Clinical Diagnosis), in "Kosankyo (Eosinophils)", Sohei Makino and Takashi Ishikawa (eds.), pp. 165 –173, Kokusai Igaku Shuppan, 1991].

Therefore, compounds that can inhibit the increase or activation of eosinophils in blood or tissues have the potential of application to diseases in which eosinophils are believed to participate as primary immunocytes in their pathophysiology, namely, virminations, hypereosinophilic syndrome (HES), eosinophilic pneumonia, eosinophilic enterogastritis, bronchial asthma, etc.

The sole therapeutic approach currently taken against diseases that manifest the increase of eosinophils is symptomatic treatments involving the administration of steroids and no treatment methods are available that target against eosinophils. Steroids cause frequent occurrence of characteristic side effects such as the lowering of resistance to bacterial infections, hyperglycemia, glycosuria, gastric ulcer, hypercalcemia, osteoporosis and obesity. In addition, the method of using steroids is strictly regulated as exemplified by prohibition of sudden discontinuation of administration and, hence, the use of steroids is extremely difficult from a practical viewpoint. Conventional drugs for curing asthma have primarily been based on their ability to inhibit histamine release, however, it has become increasingly clear that eosinophils are also involved closely in the pathophysiology of asthma and targeting against eosinophils is believed to have the potential of application to asthma which cannot be completely cured by existing methods. Under these circumstances, compounds that are safe and which yet have great potency in controlling eosinophils will provide a radical therapy for various diseases in which the increase of eosinophils is involved and, hence, the development of such compounds useful for pharmaceutical composition is sincerely awaited.

Nitorogen-containing tricyclic compounds such as imidazoquinoline derivatives are already known and U.S. Pat. No. 3,200,123 teaches 2-substituted-5,6-dihydroimidazo[ij] quinoline derivatives having an anti-inflammatory action; however, due to the total absence of disclosed pharmacological data, details about the potency of the individual compounds and the mechanism of their action are unknown. The inventors of the patent reported in Journal of Organic Chemistry, Vol. 25, pp. 1138–1147, 1960 that only part of the dihydroimidazo[ij]quinoline derivative compounds mentioned above were effective in an animal edema model prepared with dextran sulfate. However, neither prior art reference describes the action on eosinophils. According to Journal of Medicinal Chemistry, Vol. 28, pp. 298–302, 1985, 6-oxo-6H-imidazo[4,5,1-ij]quinoline-4-carboxylic acid derivative inhibited a rat passive cutaneous anaphylaxis (PCA) reaction. However, this compound not only differs in structure from the compounds of the present invention, but the prior art also fails to teach the inhibitory effect of the compound on the increase or activation of eosinophils; what is more, this prior art compound was reported to have significant renal toxicity and cause a serious side effect by inhibiting the gain in the body weight of rats.

Another teaching of imidazoquinoline derivatives is found in Unexamined Published Japanese Patent Application Hei 3-27382, which shows the diuretic action of dihydroimidazoquinoline oxime sulfonic acid derivatives. According to WO93/22313, imidazoquinoline and pyrroloquinoline derivatives, both being nitrogen-containing tricyclic compounds, inhibited IgE production in mice. However, the imidazoquinoline derivatives taught in these prior art references have different structures from the compounds of the present invention and there is no teaching at all of their action on eosinophils.

The situation is the same with other compounds having a nitrogen-containing tricyclic skeleton and no reports have ever been made on their action against eosinophils.

It is generally important in the development of pharmaceuticals that they exhibit satisfactory results not only in pharmacological tests but also in safety tests such as a subacute toxicity test (e.g. two-week drug tolerance test in rats), chronic toxicity test, reproduction and genesis toxicity test, mutagenicity test, carcinogenicity test and metabolism test. It is very useful to provide drugs that are highly safe (i.e., exhibiting satisfactory endogenous kinetics as evidenced by the absence of any disorders in drug metabolism mediated by hepatic cytochrome P450 or any serological or pathological disorders), that prove effective in smaller doses and that are easy to handle; however, no compound inhibiting eosinophils that can meet these requirements have been taught in the prior art.

DISCLOSURE OF INVENTION

Diseases in which eosinophils are believed to participate in their pathophysiology as primary immunocytes are diverse and include verminations, hypereosinophilic syndrome (HES), eosinophilic pneumonia, eosinophilic enterogastritis and bronchial asthma. These diseases are known to be accompanied by the increase of eosinophils in blood or tissues and the increase and activation of eosinophils are closely associated with the aggravation of their pathophysiology. Therefore, compounds that inhibit the increase of eosinophils are expected to prove very useful in the treatment of diseases in which eosinophils are closely involved in their pathophysiology.

Under these circumstances, the present inventors conducted many years of search for compounds that have great potency in inhibiting the increase of eosinophils. As a result, it was found that compounds having a specified imidazoquinoline skeleton had great potency in inhibiting the increase of eosinophils but that they would cause less side effects while featuring high safety. The present invention has been accomplished on the basis of this finding.

Thus, the present invention relates to imidazoquinoline derivatives represented by the following formula (I) or salts thereof:

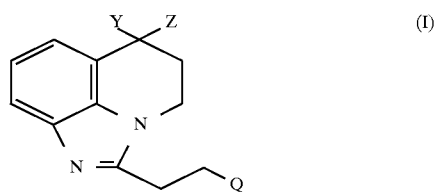

(I)

[where Q represents phenyl group that may be mono- or di-substituted with any group selected from the group consisting of a halogen atom, a nitro group, a straight or branched alkyl group having 1–4 carbon atoms that may be substituted with one or more halogen atoms, a straight or branched alkoxy group having 1–4 carbon atoms, an optionally protected hydroxyl group, an optionally protected amino group and an optionally protected carboxyl group, pyridyl group, or furyl group; Y represents either a hydrogen atom or, when taken together with Z to be described later, an oxygen atom, a methylene group that may be substituted with a carboxyl group, or the following formula (II):

=N—OR$^1$ (II)

(where R$^1$ represents an alkyl group having 1–4 carbon atoms that may be mono- or di-substituted with any group selected from the group consisting of a phenyl group and an optionally protected carboxyl group, a tosyl group, an alkanoyl group whose alkyl group has 1–6 carbon atoms, a benzoyl group, an alkenyl group having 2–4 carbon atoms, or a benzyl group that may be mono-substituted with an optionally protected carboxyl group in the phenyl moiety); Z represents a hydrogen atom, a hydroxymethyl group, a carboxymethyl group, a 2-oxo-1-pyrrolidinyl group or the following formula (III):

—A—R$^2$ (III)

(where A represents an oxygen atom, a sulfur atom or the group —NH—; R$^2$ represents a hydrogen atom, an alkyl group having 1–4 carbon atoms, an aminoalkyl group having 1–4 carbon atoms, a phenylsulfonyl group, an alkanoyl group whose alkyl group has 1–6 carbon atoms that may be mono- or di-substituted with any group selected from the group consisting of a phenyl group, an alkoxycarbonyl group whose alkyl group has 1–4 carbon atoms and an optionally protected carboxyl group, a benzoyl group that may be mono- or di-substituted with any group selected from the group consisting of a halogen atom, a nitro group, an alkyl group having 1–4 carbon atoms, an alkoxy group having 1–4 carbon atoms, an optionally protected hydroxyl group, an optionally protected carboxyl group and an optionally protected amino group, a benzyl group that may be mono- or di-susbstituted in the phenyl moiety with any group selected from the group consisting of a halogen atom, a nitro group, a phenyl group, a cyano group, a carbamoyl group, a hydroxymethyl group, a sulfo group, a carboxymethyl group, an alkyl group having 1–4 carbon atoms that may be substituted with one or more halogen atoms, an alkoxy group having 1–4 carbon atoms, an alkoxycarbonyl group whose alkyl group has 1–4 carbon atoms, an optionally protected hydroxyl group, an optionally protected carboxyl group and an optionally protected amino group, an alkoxyoxalyl group whose alkyl group has 1 or 2 carbon atoms, a cycloalkylcarbonyl group whose cycloalkyl group has 3–6 carbon atoms, a pyridinecarbonyl group or a thiophenecarbonyl group)]. The present invention also relates to processes for producing such imidazoquinoline derivatives or salts thereof, as well as therapeutics that are characterized by containing those derivatives or salts thereof and which are effective against diseases that manifest the increase of eosinophils.

Preferred substituents in the compounds represented by the formula (I), or combinations thereof include the following. Substituent Q in the formula (I) is preferably an unsubstituted phenyl group; Y is preferably either a hydrogen atom or, when taken together with Z, an oxygen atom; Z is preferably a hydrogen atom or the formula (III) [A and R$^2$ each have the same meaning as defined in the formula (I)].

When Y is a hydrogen atom and Z is the formula (III), it is more preferred that A is an oxygen atom and that R$^2$ is a hydrogen atom or a benzyl group that may be mono- or di-substituted in the phenyl moiety with any group selected from the group consisting of an alkoxycarbonyl group whose alkyl group has 1–4 carbon atoms and an optionally protected carboxyl group.

Other aspects of the present invention are exemplified below.

Use of the compounds of the formula (I) or salts thereof in the production of agents for preventing and/or treating diseases that manifest the increase of eosinophils;

Method of preventing and/or treating diseases that manifest the increase of eosinophils that is characterized by using the compounds of the formula (I) or salts thereof;

Pharmaceutical composition for preventing and/or treating diseases that manifest the increase of eosinophils, which composition comprises the compounds of the formula (I) and a pharmaceutically acceptable vehicle (carrier)

Process for producing an agent for preventing and/or treating diseases that manifest the increase of eosinophils, which agent is characterized by using the compounds of the formula (I).

BEST MODE FOR CARRYING OUT THE INVENTION

Figure 1:
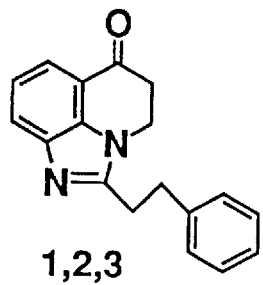
FIG. 1 is a drawing that gives chemical formulae describing the structures of the imidazoquinoline derivatives prepared in Examples 1–15.
Figure 1:
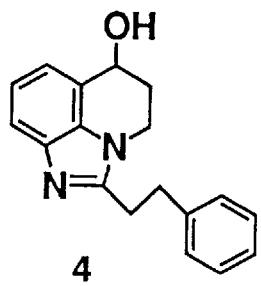
Figure 1:
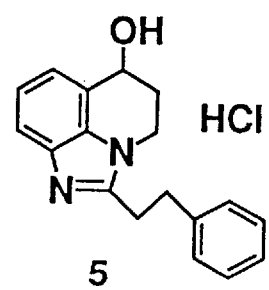
Figure 1:
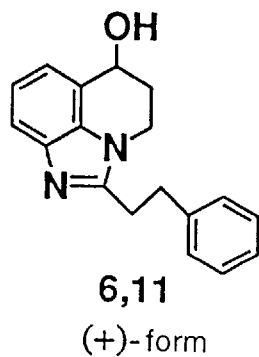
Figure 1:
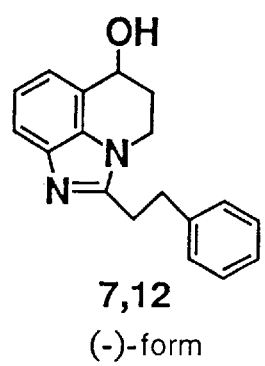
Figure 1:
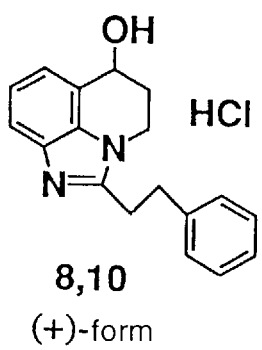
Figure 1:
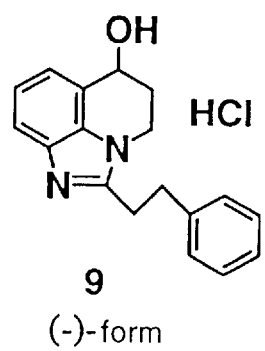
Figure 1:
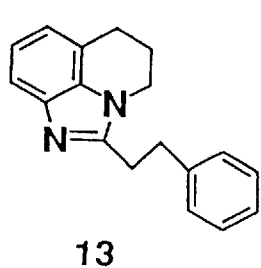
Figure 1:
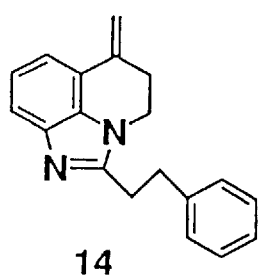
Figure 1:
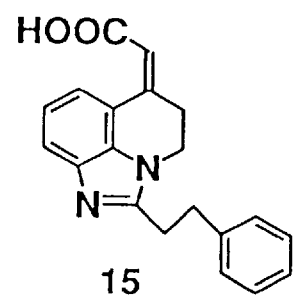

The present invention will now be described in detail.

The compounds of the invention are represented by the following formula (I):

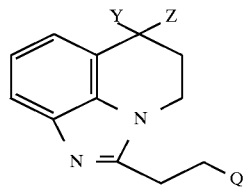

where Q represents phenyl group that may be mono- or di-substituted with any group selected from the group consisting of a halogen atom, a nitro group, a straight or branched alkyl group having 1–4 carbon atoms that may be substituted with one or more halogen atoms, a straight or branched alkoxy group having 1–4 carbon atoms, an optionally protected hydroxyl group, an optionally protected amino group and an optionally protected carboxyl group, pyridyl group, or furyl group. More specifically, the halogen atom represents a fluorine atom, a chlorine atom, a bromine atom or the like; the straight or branched alkyl group having 1–4 carbon atoms that may be substituted with one or more halogen atoms represents a trifluoromethyl group, a methyl group, an ethyl group, an n-propyl group, an i-propyl group or the like, and the straight or branched alkoxy group having 1–4 carbon atoms represents a methoxy group, an ethoxy group, an i-propoxy group, an n-propoxy group, an n-butoxy group or the like; the phenyl group that may be mono- or di-substituted with any selected group represents an unsubstituted phenyl group, a 2-substituted phenyl group, a 3-substituted phenyl group, a 4-substituted phenyl group, a 2,3-disubstituted phenyl group, a 2,4-disubstituted phenyl group, a 2,5-disubstituted phenyl group, a 2,6-disubstituted phenyl group, a 3,4-disubstituted phenyl group or the like. Preferred examples are a phenyl group, a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2,3-dichlorophenyl group, a 2,4-dichlorophenyl group, a 2,5-dichlorophenyl group, a 2,6-dichlorophenyl group, a 3,4-dichlorophenyl group, a 2-nitrophenyl group, a 3-nitrophenyl group, a 4-nitrophenyl group, a 2-trifluoromethylphenyl group, a 3-trifluoromethylphenyl group, a 4-trifluoromethylphenyl group, a 2-methylphenyl group, a 3-methylphenyl group, a 4-methylphenyl group, a 2-ethylphenyl group, a 3-ethylphenyl group, a 4-ethylphenyl group, a 4-n-propylphenyl group, a 4-i-propylphenyl group, a 2-methoxyphenyl group, a 3-methoxyphenyl group, a 4-methoxyphenyl group, a 2-ethoxyphenyl group, a 3-ethoxyphenyl group, a 4-ethoxyphenyl group, a 2-hydroxyphenyl group, a 3-hydroxyphenyl group, a 4-hydroxyphenyl group, a 2-aminophenyl group, a 3-aminophenyl group, a 4-aminophenyl group, a 2-carboxyphenyl group, a 3-carboxyphenyl group, a 4-carboxyphenyl group, a 2-furyl group, a 3-furyl group, a 4-furyl group, a 2-pyridyl group, a 3-pyridyl group and a 4-pyridyl group. A phenyl group is particularly preferred.

In the formula (I), Y and Z which are described below may be taken together to represent an oxygen atom, a methylene group that may be substituted with a carboxyl group, or the following formula (II):

$$=N—OR^1 \qquad (II)$$

(where $R^1$ represents an alkyl group having 1–4 carbon atoms that may be mono- or di-substituted with any group selected from between a phenyl group and an optionally protected carboxyl group, a tosyl group, an alkanoyl group having 1–6 carbon atoms, a benzoyl group, an alkenyl group having 2–4 carbon atoms, or a benzyl group that may be mono-substituted with an optionally protected carboxyl group in the phenyl moiety). Speaking of $R^1$ more specifically, the alkanoyl group having 1–6 carbon atoms represents an acetyl group, a propanoyl group, a butanoyl group, a pentanoyl group, a hexanoyl group or the like; the alkyl group having 1–4 carbon atoms that may be mono- or di-substituted with any group selected from between a phenyl group and an optionally protected carboxyl group represents a methyl group, an ethyl group, an n-propyl group, an n-butyl group, a mono-substituted methyl group, a mono-substituted ethyl group, a mono-substituted n-propyl group, a mono-substituted n-butyl group or the like; the alkenyl group having 2–4 carbon atoms represents a vinyl group, a 1-propenyl group, a 2-propenyl group, a 1-butenyl group, a 2-butenyl group, a 3-butenyl group or the like; the benzyl group that may be mono-substituted with an optionally protected carboxyl group in the phenyl moiety represents a benzyl group, a 2-carboxybenzyl group, a 3-carboxybenzyl group, 4-carboxybenzyl group or the like. Preferably, Y and Z combine together to represent an oxygen atom, a methylene group, a carboxymethylene group, a tosyloxyimino group, an acetoxyimino group, a propanoyloxyimino group, a butanoyloxyimino group, a pentanoyloxyimino group, a hexanoyloxyimino group, a benzoyloxyimino group, a methoxyimino group, an ethoxyimino group, an n-propoxyimino group, an n-butoxyimino group, a 2-carboxyphenylmethoxyimino group, a phenylmethoxyimino group, a 2-phenylethoxyimino group, a 3-phenyl-n-propoxyimino group, a 4-phenyl-n-butoxyimino group, a carboxymethoxyimino group, a 2-carboxyethoxyimino group, a 3-carboxy-n-propoxyimino group, a 4-carboxy-n- butoxyimino group, a methoxycarbonylmethoxyimino group, a 2-methoxycarbonylethoxyimino group, a 3-methoxycarbonyl-n-propoxyimino group, a 4-methoxycarbonyl-n-butoxyimino group, a vinyloxyimino group, a 1-propenyloxyimino group, a 2-propenyloxyimino group, a 1-butenyloxyimino group, a 2-butenyloxyimino group, a 3-butenyloxyimino group or the like.

When Y in the formula (I) is a hydrogen atom, Z represents a hydrogen atom, a hydroxymethyl group, a carboxymethyl group, a 2-oxo-1-pyrrolidinyl group or the following formula (III):

(where A represents an oxygen atom, a sulfur atom or the group —NH—; $R^2$ represents a hydrogen atom, an alkyl group having 1–4 carbon atoms, an aminoalkyl group having 1–4 carbon atoms, a phenylsulfonyl group, an alkanoyl group whose alkyl group has 1–6 carbon atoms that may be mono- or di-substituted with any group selected from the group consisting of a phenyl group, an alkoxycarbonyl group whose alkyl group has 1–4 carbon atoms and an optionally protected carboxyl group, a benzoyl group that may be mono- or di-substituted with any group selected from the group consisting of a halogen atom, a nitro group, an alkyl group having 1–4 carbon atoms, an alkoxy group having 1–4 carbon atoms, an optionally protected hydroxyl group, an optionally protected carboxyl group and an optionally protected amino group, a benzyl group that may be mono- or di-subsbituted in the phenyl moiety with any group selected from the group consisting of a halogen atom, a nitro group, a phenyl group, a cyano group, a carbamoyl group, a hydroxymethyl group, a sulfo group, a carboxymethyl group, an alkyl group having 1–4 carbon atoms that may be substituted with one or more halogen atoms, an alkoxy group having 1–4 carbon atoms, an alkoxycarbonyl group whose alkyl group has 1–4 carbon atoms, an optionally protected hydroxyl group, an optionally protected carboxyl group and an optionally protected amino group, an alkoxyoxalyl group whose alkyl group has 1 or 2 carbon atoms, a cycloalkylcarbonyl group whose cycloalkyl group has 3–6 carbon atoms, a pyridinecarbonyl group or a thiophenecarbonyl group). Speaking of $R^2$ more specifically, the alkyl group having 1–4 carbon atoms represents a methyl group, an ethyl group, an n-propyl group, an i-propyl group, an n-butyl group or the like; the aminoalkyl group having 1–4 carbon atoms represents an aminomethyl group, a 2-aminoethyl group, a 3-amino-n-propyl group, a 4-amino-n-butyl group or the like; the alkanoyl group having 1–6 carbon atoms that may be mono- or di-substituted with any group selected from the group consisting of a phenyl group, an alkoxycarbonyl group having 1–4 carbon atoms and an optionally protected carboxyl group represents an acetyl group, a propanoyl group, a butanoyl group, a pentanoyl group, a hexanoyl group, a phenylacetyl group, a 3-phenylpropanoyl group, a 4-phenylbutanoyl group, a 5-phenylpentanoyl group, a 6-phenylhexanoyl group, a methoxycarbonylacetyl group, a 3-methoxycarbonylpropanoyl group, a 4-methoxycarbonylbutanoyl group, a 5-methoxycarbonylpentanoyl group, a 6-methoxycarbonylhexanoyl group, an ethoxycarbonylacetyl group, a 3-ethoxycarbonylpropanoyl group, a 4-ethoxycarbonylbutanoyl group, a 5-ethoxycarbonylpentanoyl group, a 6-ethoxycarbonylhexanoyl group, a carboxyacetyl group, a 3-carboxypropanoyl group, a 4-carboxybutanoyl group, a 5-carboxypentanoyl group, a 6-carboxyhexanoyl group or the like; the benzoyl group that may be mono- or di-substituted with any group selected from the group consisting of a halogen atom, a nitro group, an alkyl group having 1–4 carbon atoms, an alkoxy group having 1–4 carbon atoms, an optionally protected hydroxyl group, an optionally protected carboxyl group and an optionally protected amino group represents a benzoyl group, a 2-fluorobenzoyl group, a 3-fluorobenzoyl group, a 4-fluorobenzoyl group, a 2-chlorobenzoyl group, a 3-chlorobenzoyl group, a 4-chlorobenzoyl group, a 2-bromobenzoyl group, a 3-bromobenzoyl group, a 4-bromobenzoyl group, a 2-nitrobenzoyl group, a 3-nitrobenzoyl group, a 4-nitrobenzoyl group, a 2-methylbenzoyl group, a 3-methylbenzoyl group, a 4-methylbenzoyl group, a 2-ethylbenzoyl group, a 3-ethylbenzoyl group, a 4-ethylbenzoyl group, a 2-n-propylbenzoyl group, a 3-n-propylbenzoyl group, a 4-n-propylbenzoyl group, a 2-i-propylbenzoyl group, a 3-i-propylbenzoyl group, a 4-i-propylbenzoyl group, a 2-n-butylbenzoyl group, a 3-n-butylbenzoyl group, a 4-n-butylbenzoyl group, a 2-i-butylbenzoyl group, a 3-i-butylbenzoyl group, a 4-i-butylbenzoyl group, a 2-t-butylbenzoyl group, a 3-t-butylbenzoyl group, a 4-t-butylbenzoyl group, a 2-methoxybenzoyl group, a 3-methoxybenzoyl group, a 4-methoxybenzoyl group, a 2-ethoxybenzoyl group, a 3-ethoxybenzoyl group, a 4-ethoxybenzoyl group, a 2-n-propoxybenzoyl group, a 3-n-propoxybenzoyl group, a 4-n-propoxybenzoyl group, a 2-n-butoxybenzoyl group, a 3-n-butoxybenzoyl group, a 4-n-butoxybenzoyl group, a 2-hydroxybenzoyl group, a 3-hydroxybenzoyl group, a 4-hydroxybenzoyl group, a 2-carboxybenzoyl group, a 3-carboxybenzoyl group, a 4-carboxybenzoyl group, a 2-aminobenzoyl group, a 3-aminobenzoyl group, a 4-aminobenzoyl group, a 2,3-dichlorobenzoyl group, a 2,4-dichlorobenzoyl group, a 2,5-dichlorobenzoyl group, a 2,6-dichlorobenzoyl group, a 3,4-dichlorobenzoyl group, a 3,5-dichlorobenzoyl group, a 2,3-dimethylbenzoyl group, a 2,4-dimethylbenzoyl group, a 2,5-dimethylbenzoyl group, a 2,6-dimethylbenzoyl group, a 2,3-dimethoxybenzoyl group, a 2,4-dimethoxybenzoyl group, a 2,5-dimethoxybenzoyl group, a 2,6-dimethoxybenzoyl group, a 3,4-dimethoxybenzoyl group, a 3,5-dimethoxybenzoyl group or the like; the benzyl group that may be mono- or di-substituted in the phenyl moiety with any group selected from the group consisting of a halogen atom, a nitro group, a phenyl group, a cyano group, a carbamoyl group, a hydroxymethyl group, a sulfo group, a carboxymethyl group, an alkyl group having 1–4 carbon atoms that may be substituted with one or more halogen atoms, an alkoxy group having 1–4 carbon atoms, an alkoxycarbonyl group having 1–4 carbon atoms, an optionally protected hydroxyl group, an optionally protected carboxyl group and an optionally protected amino group represents a benzyl group, a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, a 2-nitrobenzyl group, a 3-nitrobenzyl group, a 4-nitrobenzyl group, a 2-phenylbenzyl group, a 3-phenylbenzyl group, a 4-phenylbenzyl group, a 2-cyanobenzyl group, a 3-cyanobenzyl group, a 4-cyanobenzyl group, a 2-carbamoylbenzyl group, a 3-carbamoylbenzyl group, a 4-carbamoylbenzyl group, a 2-hydroxymethylbenzyl group, a 3-hydroxymethylbenzyl group, a 4-hydroxymethylbenzyl group, a 2-sulfobenzyl group, a 3-sulfobenzyl group, a 4-sulfobenzyl group, a 2-carboxymethylbenzyl group, a 3-carboxymethylbenzyl group, a 4-carboxymethylbenzyl group, a 2-trifluoromethylbenzyl group, a 3-trifluoromethylbenzyl group, a 4-trifluoromethylbenzyl group, a 2-methylbenzyl group, a 3-methylbenzyl group, a 4-methylbenzyl group, a 2-ethylbenzyl group, a 3-ethylbenzyl group, a 4-ethylbenzyl group, a 2-n-propylbenzyl group, a 3-n-propylbenzyl group, a 4-n-propylbenzyl group, a 2-i-propylbenzyl group, a 3-2-i-propylbenzyl group, a 4-3-i-propylbenzyl group, a 2-n-butylbenzyl group, a 3-n-butylbenzyl group, a 4-n-butylbenzyl group, a 2-i-butylbenzyl group, a 3-i-butylbenzyl group, a 4-i-butylbenzyl group, a 2-t-butylbenzyl group, a 3-t-butylbenzyl group, a 4-t-butylbenzyl group, a 2-methoxybenzyl group, a 3-methoxybenzyl group, a 4-methoxybenzyl group, a 2-ethoxybenzyl group, a 3-ethoxybenzyl group, a 4-ethoxybenzyl group, a 2-n-propoxybenzyl group, a 3-n-propoxybenzyl group, a 4-n-propoxybenzyl group, a 2-n-butoxybenzyl group, a 3-n-butoxybenzyl group, a 4-n-butoxybenzyl group, a 2-methoxycarbonylbenzyl group, a 3-methoxycarbonylbenzyl group, a 4-methoxycarbonylbenzyl group, a 2-ethoxycarbonylbenzyl group, a 3-ethoxycarbonylbenzyl group, a 4-ethoxycarbonylbenzyl group, a 2-n-propoxycarbonylbenzyl group, a 3-n-propoxycarbonylbenzyl group, a 4-n-propoxycarbonylbenzyl group, a 2-n-butoxycarbonylbenzyl group, a 3-n-butoxycarbonylbenzyl group, a 4-n-butoxycarbonylbenzyl group, a 2-hydroxybenzyl group, a 3-hydroxybenzyl group, a 4-hydroxybenzyl group, a 2-carboxybenzyl group, a 3-carboxybenzyl group, a 4-carboxybenzyl group, a 2-aminobenzyl group, a 3-aminobenzyl group, a 4-aminobenzyl group, a 2-carboxy-4-chlorobenzyl group, a 2-carboxy-4-nitrobenzyl group, a 2-carboxy-4-trifluoromethylbenzyl group, a 2-carboxy-4-methoxybenzyl group, a 2-carboxy-4-methoxycarbonylbenzyl group, a 2,4-dicarboxybenzyl group, a 4-amino-2-carboxybenzyl group, a 2-carboxy-4-hydroxymethylbenzyl group, a 2,4-bis(methoxycarbonyl) benzyl group, a 4-chloro-2-hydroxymethylbenzyl group, a 2-hydroxymethyl-4-nitrobenzyl group, a 2-hydroxymethyl-4-trifluoromethylbenzyl group, a 2-hydroxymethyl-4-methoxybenzyl group, a 2-hydroxymethyl-4-methoxycarbonylbenzyl group, a 4-carboxy-2-hydroxymethylbenzyl group, a 4-amino-2-hydroxymethylbenzyl group, a 2-carboxy-6-chlorobenzyl group, a 2-carboxy-6-nitrobenzyl group, a 2-carboxy-6-trifluoromethylbenzyl group, a 2-carboxy-6-methoxybenzyl group, a 2-carboxy-6-methoxycarbonylbenzyl group, a 2,6-dicarboxybenzyl group, a 2-amino-6-carboxybenzyl group, a 2-carboxy-6-hydroxymethylbenzyl group, a 2,6-bis(methoxycarbonyl)benzyl group, a 2-chloro-6-hydroxymethylbenzyl group, a 2-hydroxymethyl-6-nitrobenzyl group, a 2-hydroxymethyl-6-trifluoromethylbenzyl group, a 2-hydroxymethyl-6-methoxybenzyl group, a 2-hydroxymethyl-6-methoxycarbonylbenzyl group, a 2-amino-6-hydroxymethylbenzyl group, a 2-carboxy-3-chlorobenzyl group, a 2-carboxy-3-methoxybenzyl group, a 2,3-dicarboxybenzyl group, a 2,3-bis(methoxycarbonyl)benzyl group, a 2-carboxy-3-hydroxymethylbenzyl group, a 3-chloro-2-hydroxymethylbenzyl group, a 2-hydroxymethyl-3-methoxybenzyl group, a 3-carboxy-2-hydroxymethylbenzyl group, a 2-carboxy-5-chlorobenzyl group, a 2-carboxy-5-methoxybenzyl group, a 2,5-dicarboxybenzyl group, a 2,5-bis(methoxycarbonyl)benzyl group, a 2-carboxy-5-hydroxymethylbenzyl group, a 5-chloro-2-hydroxymethylbenzyl group, a 2-hydroxymethyl-5-methoxylbenzyl group, a 5-carboxy-2-hydroxymethylbenzyl group, a 3,4-dicarboxybenzyl group, a 3,4-bis(methoxycarbonyl)benzyl group or the like; the alkoxyoxalyl group having 1 or 2 carbon atoms represents a methoxyoxalyl group or an ethoxyoxalyl group; the cycloalkylcarbonyl group having 3–6 carbon atoms represents a cyclopropylcarbonyl group, a cyclobutylcarbonyl group, a cyclopentylcarbonyl group or a cyclohexylcarbonyl group; the pyridinecarbonyl group represents a 2-pyridinecarbonyl group, a 3-pyridinecarbonyl group or a 4-pyridinecarbonyl group; the thiophenecarbonyl group represents a 2-thiophenecarbonyl group, a 3-thiophenecarbonyl group or a 4-thiophenecarbonyl group.

Preferably, Y represents a hydrogen atom or, when taken together with Z, an oxygen atom, or Z represents a hydrogen atom or the formula (III).

When Z represents the formula (III), A represents preferably an oxygen atom.

When A in the formula (III) is an oxygen atom, $R^2$ represents preferably a hydrogen atom or a benzyl group that may be mono- or di-substituted in the phenyl moiety with any group selected from the group consisting of a halogen atom, a nitro group, a phenyl group, a cyano group, a carbamoyl group, a hydroxymethyl group, a sulfo group, a carboxymethyl group, an alkyl group having 1–4 carbon atoms that may be substituted with one or more halogen atoms, an alkoxy group having 1–4 carbon atoms, an alkoxycarbonyl group whose alkyl group has 1–4 carbon atoms, an optionally protected hydroxyl group, an optionally protected carboxyl group and an optionally protected amino group and in the case of substitution in the phenyl moiety, at least one substitution is preferably in the ortho position.

Hence, specifically, Z is preferably a hydroxyl group, a phenylmethoxy group, a 2-fluorophenylmethoxy group, a 2-chlorophenylmethoxy group, a 2-bromophenylmethoxy group, a 2-nitrophenylmethoxy group, a 2-phenylphenylmethoxy group, a 2-cyanophenylmethoxy group, a 2-carbamoylphenylmethoxy group, a 2-hydroxymethylphenylmethoxy group, a 2-sulfophenylmethoxy group, a 2-carboxymethylphenylmethoxy group, a 2-trifluoromethylphenylmethoxy group, a 2-methylphenylmethoxy group, a 2-ethylphenylmethoxy group, a 2-n-propylphenylmethoxy group, a 2-i-propylphenylmethoxy group, a 2-n-butylphenylmethoxy group, a 2-i-butylphenylmethoxy group, a 2-t-butylphenylmethoxy group, a 2-methoxyphenylmethoxy group, a 2-ethoxyphenylmethoxy group, a 2-n-propoxyphenylmethoxy group, a 2-n-butoxyphenylmethoxy group, a 2-methoxycarbonylphenylmethoxy group, a 2-ethoxycarbonylphenylmethoxy group, a 2-n-propoxycarbonylphenylmethoxy group, a 2-n-butoxycarbonylphenylmethoxy group, a 2-hydroxyphenylmethoxy group, a 2-carboxyphenylmethoxy group, a 2-aminophenylmethoxy group, a 2-carboxy-4-chlorophenylmethoxy group, a 2-carboxy-4-nitrophenylmethoxy group, a 2-carboxy-4-trifluoromethylphenylmethoxy group, a 2-carboxy-4-methoxyphenylmethoxy group, a 2-carboxy-4-methoxycarbonylphenylmethoxy group, a 2-carboxy-4-dicarboxyphenylmethoxy group, a 4-amino-2-carboxyphenylmethoxy group, a 2-carboxy-4-hydroxymethylphenylmethoxy group, a 2,4-bis(methoxycarbonyl)phenylmethoxy group, a 2-carboxy-6-chlorophenylmethoxy group, a 2-carboxy-6-nitrophenylmethoxy group, a 2-carboxy-6- trifluoromethylphenylmethoxy group, a 2-carboxy-6-methoxyphenylmethoxy group, a 2-carboxy-6-methoxycarbonylphenylmethoxy group, a 2,6-dicarboxyphenylmethoxy group, a 2-amino-6-carboxyphenylmethoxy group, a 2-carboxy-6-hydroxymethylphenylmethoxy group, a 2,6-bis (methoxycarbonyl)phenylmethoxy group, a 2-carboxy-3-chlorophenylmethoxy group, a 2-carboxy-3-methoxyphenylmethoxy group, a 2,3-dicarboxyphenylmethoxy group, a 2,3-bis (methoxycarbonyl)phenylmethoxy group, a 2-carboxy-3-hydroxymethylphenylmethoxy group, a 2-carboxy-3-nitrophenylmethoxy group, a 2-carboxy-3-trifluorophenylmethoxy group, a 2-carboxy-3-methoxycarbonylphenylmethoxy group, a 3-amino-2-carboxyphenylmethoxy group, a 2-carboxy-5-chlorophenylmethoxy group, a 2-carboxy-5-methoxyphenylmethoxy group, a 2,5-dicarboxyphenylmethoxy group, a 2,5-bis (methoxycarbonyl)phenylmethoxy group, a 2-carboxy-5-hydroxymethylphenylmethoxy group or the like, and more preferably Z is a hydroxy group, a 2-methoxycarbonylphenylmethoxy group, a 2-carboxyphenylmethoxy group or 2,3-dicarboxyphenylmethoxy group.

Protective groups may be introduced as appropriate into the compounds of the formula (I) in the process of reactions and removed at the final stage. Exemplary protective groups for the hydroxyl or carboxyl group include lower alkyl groups such as a methyl group, an ethyl group or a t-butyl group, aralkyl groups such as a benzyl group or a 4-nitrobenzyl group and various others; lower alkyl groups are preferred from handling and reactivity viewpoints. Exemplary protective groups for the amino or hydrazono group include a trityl group, a tosyl group, a mesyl group, a formyl group, a chloroacetyl group, a t-butoxycarbonyl group, etc. Exemplary protective groups for the sulfo group are lower alkyl groups such as a methyl group, an ethyl group or a t-butyl group.

Stereoisomers of the compounds of the invention will now be described.

If Y and Z differ in the compounds represented by the formula (I), they can provide optically active forms. Stated more specifically, the carbon to which Y and Z are bound is asymmetric, providing two enantiomers.

If Y and Z together represent a methylene group that may be substituted with a carboxyl group, cis-trans isomers can exist. If Y and Z together represent the formula (II):

  (II)

(where $R^1$ represents an alkyl group having 1–4 carbon atoms that may be mono- or di-substituted with any group selected from the group consisting of a phenyl group and a carboxyl group, a tosyl group, an alkanoyl group whose alkyl group has 1–6 carbon atoms, a benzoyl group, an alkenyl group having 2–4 carbon atoms, or a benzyl group that may be mono-substituted with an optionally protected carboxyl group in the phenyl moiety), syn-anti isomers can occur. Cis-trans isomers are also occur if $R^1$ is an alkenyl group having 3 or 4 carbon atoms.

The present invention encompasses all of these optically active or inactive forms of stereoisomerism, as well as any of their mixtures.

The compounds of the invention may form salts with inorganic or organic acids. Examples of such salts include salts with inorganic acids such as hydrochlorides, hydrobromides, phosphates and sulfates, salts with organic acids such as acetates, oxalates, citrates, tartrates, maleates, alginates, p-toluenesulfonates and salicylates, and salts with acidic amino acids such as glutamates and aspartates. Depending on the type of substituents, the compounds of the invention may form salts with inorganic or organic bases. Examples of these salts include alkali metal salts such as sodium salts and potassium salts, alkaline earth metal salts such as magnesium salts and calcium salts, salts with inorganic bases such as ammonium salts, salts with organic bases such as triethylamine salts and pyridine salts, and salts with basic amino acids such as arginine salts, lysine salts and histidine salts. The compounds of the invention or salts thereof may also form solvates with solvents such as water, ethanol and glycerol.

The compounds of the invention having an imidazoquinoline skeleton have a great potency in inhibiting the increase of eosinophils. Therefore, the therapeutics of the invention for diseases that manifest the increase of eosinophils can be used to prevent, relieve or treat diseases that manifest the increase of eosinophils, namely those diseases in which eosinophils are believed to participate in their pathophysiology as primary immunocytes. The diseases that are to be controlled with the therapeutics of the invention and in which eosinophils are believed to participate in their pathophysiology as primary immunocytes are various eosinophil-caused diseases including verminations, hypereosinophilic syndrome (HES), eosinophilic pneumonia, eosinophilic enterogastritis and bronchial asthma.

The nitrogen-containing tricyclic compounds of the invention or salts thereof can be produced by the production steps to be described below or modifications thereof. In the following formulae, the substituents in the formula (I) are defined as above and in the other formulae, the following definitions hold unless otherwise noted:

Q represents a phenyl group that may be mono- or di-substituted with any group selected from the group consisting of a halogen atom, a nitro group, a straight or branched alkyl group having 1–4 carbon atoms that may be substituted with one or more halogen atoms, a straight or branched alkoxy group having 1–4 carbon atoms, an optionally protected hydroxyl group, an optionally protected amino group and an optionally protected carboxyl group, pyridyl group or furyl group; Y represents either a hydrogen atom or, when taken together with Z to be described later, an oxygen atom, a methylene group that may be substituted with a carboxyl group, or the following formula (II):

  (II)

(where $R^1$ represents an alkyl group having 1–4 carbon atoms that may be mono- or di-substituted with any group selected from the group consisting of a phenyl group and an optionally protected carboxyl group, a tosyl group, an alkanoyl group whose alkyl group has 1–6 carbon atoms, a benzoyl group, an alkenyl group having 2–4 carbon atoms, or a benzyl group that may be mono-substituted with an optionally protected carboxyl group in the phenyl moiety); z represents a hydrogen atom, a hydroxymethyl group, a carboxymethyl group, a 2-oxo-1-pyrrolidinyl group or the following formula (III):

  (III)

(where A represents an oxygen atom, a sulfur atom or the group —NH—; $R^2$ represents a hydrogen atom, an alkyl group having 1–4 carbon atoms, an aminoalkyl group having 1–4 carbon atoms, a phenylsulfonyl group, an alkanoyl group whose alkyl group has 1–6 carbon atoms that may be mono- or di-substituted with any group selected from the group consisting of a phenyl group, an alkoxycarbonyl group whose alkyl group has 1–4 carbon atoms and an optionally protected carboxyl group, a benzoyl group that may be mono- or di-substituted with any group selected from the group consisting of a halogen atom, a nitro group, an alkyl group having 1–4 carbon atoms, an alkoxy group having 1–4 carbon atoms, an optionally protected hydroxyl group, an optionally protected carboxyl group and an optionally protected amino group, a benzyl group that may be mono- or di-subsbituted in the phenyl moiety with any group selected from the group consisting of a halogen atom, a nitro group, a phenyl group, a cyano group, a carbamoyl group, a hydroxymethyl group, a sulfo group, a carboxymethyl group, an alkyl group having 1–4 carbon atoms that may be substituted with one or more halogen atoms, an alkoxy group having 1–4 carbon atoms, an alkoxycarbonyl group whose alkyl group has 1–4 carbon atoms, an optionally protected hydroxyl group, an optionally protected carboxyl group and an optionally protected amino group, an alkoxyoxalyl group whose alkyl group has 1 or 2 carbon atoms, a cycloalkylcarbonyl group whose cycloalkyl group has 3–6 carbon atoms, a pyridinecarbonyl group or a thiophenecarbonyl group).

The processes for producing the compounds of the invention will now be described, and the individual reaction steps will be explained.

by reacting 8-amino-2,3-dihydro-4(1H)-quinoline which is a he formula (V) with a compound represented by the following formula (VI):

[where Q has the same meaning as defined in the formula (I)], or a compound represented by the following formula (VII):

[where Q has the same meaning as defined in the formula (I) and R' represents a lower alkyl group], or a compound represented by the following formula (VIII):

[where Q has the same meaning as defined in the formula (I)], or a compound represented by the following formula (IX):

[where Q has the same meaning as defined in the formula (I) and R' represents a lower alkyl group], or a compound represented by the following formula (X):

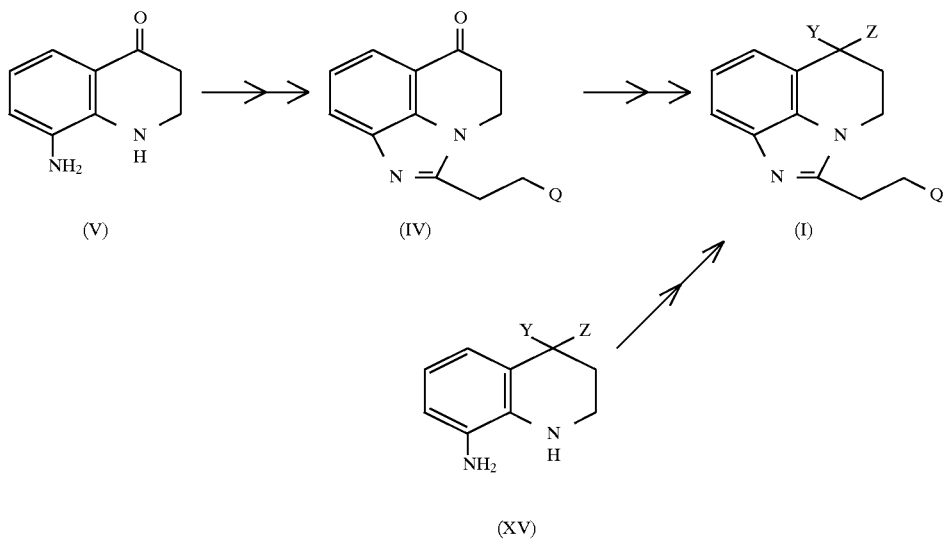

Compounds of the formula (IV) in which Y and Z in the formula (I) combine together to represent an oxygen atom can be obtained in accordance with the reaction step A:

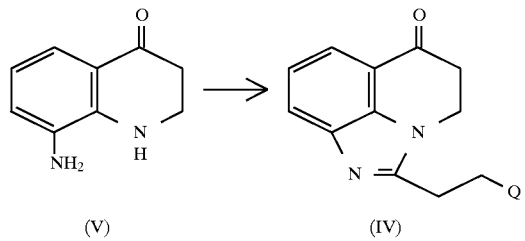

[where Q has the same meaning as defined in the formula (I)] under appropriate reaction conditions. These reactions may be carried out in accordance with the procedures disclosed in Unexamined Published Japanese Patent Application Hei 3-27382 and WO93/22313.

These references are incorporated into this specification.

Process for Producing Compounds of the Formula (I)

Reaction Step B-1

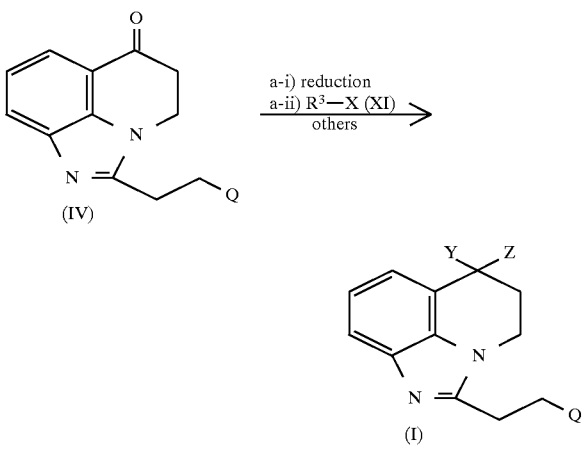

Reaction Step B-2

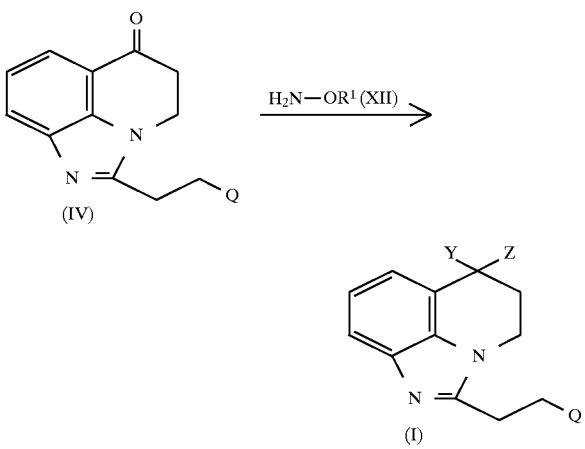

Reaction Step B-3

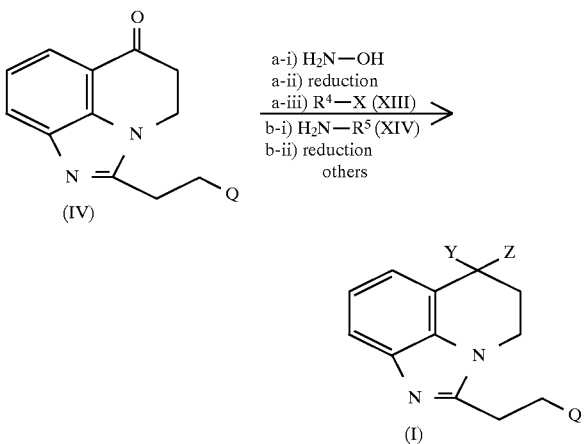

The ketone derivative represented by the formula (IV) is subjected to a suitable reduction reaction, for example, reduction with a reducing agent such as sodium borohydride or the Meerwein-Ponndorf reduction, in an alcoholic solvent such as methanol or ethanol at a temperature from −70° C. to the boiling point of the solvent, preferably from 0° C. to 100° C., thereby yielding a hydroxy derivative. If necessary, it may be reacted with a compound represented by the following formula (XI):

$$R^3\text{—}X \qquad (XI)$$

(where X represents a leaving group capable of generating a stable anion, such as a halide (e.g. chlorine), a carboxylate (e.g. acetate or benzoate), a sulfonate such as tosylate or an alkylphosphonate, and $R^3$ represents an alkyl group having 1–4 carbon atoms, a benzoyl group that may be mono- or di-substituted with any group selected from the group consisting of a halogen atom, a nitro group, an alkyl group having 1–4 carbon atoms, an alkoxy group having 1–4 carbon atoms, an optionally protected hydroxyl group, an optionally protected carboxyl group and an optionally protected amino group, or a benzyl group that may be mono- or di-substituted in the phenyl moiety with any group selected from the group consisting of a halogen atom, a nitro group, a phenyl group, a cyano group, an optionally protected carbamoyl group, an optionally protected hydroxymethyl group, an optionally protected sulfo group, an optionally protected carboxymethyl group, an alkyl group having 1–4 carbon atoms that may be substituted with one or more halogen atoms, an alkoxy group having 1–4 carbon atoms, an alkoxycarbonyl group whose alkyl group has 1–4 carbon atoms, an optionally protected hydroxyl group, an optionally protected carboxyl group or an optionally protected amino group) in a reaction-inert solvent such as an aromatic hydrocarbon, a halogen-containing organic solvent such as dichloromethane or 1,2-dichloroethane, an ether (e.g. diethyl ether, tetrahydrofuran or dioxane) or N,N-dimethylformamide, a basic solvent (e.g. pyridine or 4-dimethylaminopyridine) or a solvent system consisting of a mixture of these solvents at a temperature ranging from −70° C. to the boiling point of the solvent, preferably from room temperature to 130° C., thereby yielding a compound of the formula (I) in an ether or ester derivative. Depending on the need, the compound thus obtained may be subjected to a reaction such as hydrolysis or reduction, thereby producing a compound of the formula (I).

Alternatively, the above-mentioned hydroxy derivative may be reacted with a reagent such as a Lawesson reagent, or a halogeno or sulfonyloxy derivative that are obtained by halogenation or sulfonylation may be reacted with a reagent such as sodium hydrosulfide, thereby producing a compound of the formula (I) in a thiol derivative. If necessary, the thiol derivative may be reacted with an alkyl halide having 1–4 carbon atoms or a benzyl halide that may be mono- or di-substituted in the phenyl moiety with any group selected from the group consisting of a halogen atom, a nitro group, a phenyl group, a cyano group, an optionally protected carbamoyl group, an optionally protected hydroxymethyl group, an optionally protected sulfo group, an optionally protected carboxymethyl group, an alkyl group having 1–4 carbon atoms that may be substituted with one or more halogen atoms, an alkoxy group having 1–4 carbon atoms, an alkoxycarbonyl group whose alkyl group has 1–4 carbon atoms, an optionally protected hydroxyl group, an optionally protected carboxyl group or an optionally protected amino group), thereby producing a compound of the formula (I) in a sulfide derivative.

The ketone derivative represented by the formula (IV) may be treated with hydrazine or substituted hydrazine or salts thereof in a reaction-inert solvent such as an aromatic hydrocarbon, a halogen-containing organic solvent such as dichloromethane or 1,2-dichloroethane, an ether (e.g. diethyl ether, tetrahydrofuran or dioxane) or an alcoholic solvent (e.g. ethanol or methanol), a basic solvent such as pyridine or solvent systems consisting of mixtures of these solvents at a temperature ranging from −70° C. to the boiling point of the solvent, preferably from room temperature to 130° C., thereby yielding hydrazone, which is further treated with sodium borohydride or the like or heated under an alkaline condition; alternatively, the compound of the formula (IV) may be subjected to the Clemmensen reduction or thioketal reduction; alternatively, the above-described hydroxy derivative may be placed in a reaction-inert solvent such as a halogen-containing organic solvent such as dichloromethane, an ether (e.g. diethyl ether or dioxane) or N,N-dimethylformamide, a basic solvent (e.g. pyridine or 4-dimethylaminopyridine) or solvent systems consisting of mixtures of these solvents at a temperature ranging from −70° C. to the boiling point of the solvent, preferably from −30° C. to 100° C. and are either converted to a halogeno form by treatment with a halogenating reagent such as hydrogen chloride, phosphorus trichloride, phosphorus pentachloride, phosphorus oxychloride or bromides corresponding thereto or treated with a suitable sulfonylating reagent such as mesyl chloride or tosyl chloride so that the compound is converted to the corresponding sulfonyloxy derivative, followed by either hydrogenation in the presence of a metal catalyst such as palladium or reduction with lithium aluminum hydride or the like, thereby yielding a compound of the formula (I) where Y and Z are both a hydrogen atom (the above procedure is reaction step B-1).

The ketone derivative of the formula (IV) may be reacted with a compound represented by the following formula (XII):

   (XII)

(where $R^1$ is an alkyl group having 1–4 carbon atoms that may be mono- or di-substituted with any group selected from the group consisting of a phenyl group and a carboxyl group, a tosyl group, an alkanoyl group whose alkyl group has 1–6 carbon atoms, a benzoyl group, an alkenyl group having 2–4 carbon atoms, or a benzyl group that may be mono-substituted with an optionally protected carboxyl group in the phenyl moiety) in the above-mentioned inert aromatic hydrocarbon, an inert halogen-containing organic solvent such as dichloromethane or 1,2-dichloroethane, reaction inert solvent such as an ether (e.g. diethyl ether, tetrahydrofuran or dioxane) or an alcoholic solvent (e.g. ethanol or methanol), basic solvent (e.g. pyridine) or a solvent system consisting of a mixture of these solvents at a temperature ranging from −70° C. to the boiling point of the solvent, preferably from room temperature to 130° C., thereby yielding a compound of the formula (I) that is an oxime ether, oxime ester or the like (the above procedure is reaction step B-2).

The ketone derivative of the formula (IV) may be reacted with hydroxylamine or a salt thereof in an inert aromatic hydrocarbon, an inert halogen-containing organic solvent such as dichloromethane or 1,2-dichloroethane, a reaction inert solvent such as an ether (e.g. diethyl ether, tetrahydrofuran or dioxane) or an alcoholic solvent (e.g. ethanol or methanol), a basic solvent such as pyridine or solvent systems consisting of mixtures of these solvents at a temperature ranging from −70° C. to the boiling point of the solvent, preferably from room temperature to 130° C., thereby yielding the corresponding oxime form of the following formula (Ivb):

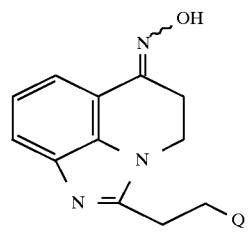

(where Q is phenyl group that may be mono- or di-substituted with any group selected from the group consisting of a halogen atom, a nitro group, a straight or branched alkyl group having 1–4 carbon atoms that may be substituted with one or more than halogen atoms, a straight or branched alkoxy groups having 1–4 carbon atoms, an optionally protected hydroxyl group, an optionally protected amino group and an optionally protected carboxyl group, pyridyl group or furyl group; N~O represents a syn or anti bond).

The resulting oxime derivative may be either hydrogenated in the presence of a metal catalyst such as palladium or reduced with lithium aluminum hydride or the like to give the corresponding amino derivative (Y and Z in the formula (I) represent a hydrogen atom and an amino group, respectively); if necessary, the amino derivative may be reacted with a compound represented by the following formula (XIII):

   (XIII)

(where X represents a leaving group capable of generating a stable anion, as exemplified by a halide such as chlorine atom, a carboxylate such as acetate or benzoate, a sulfonate such as tosylate or an alkylphosphonate, and $R^4$ represents an amino group, a phenylsulfonyl group, a pyridinecarbonyl group, a thiophenecarbonyl group, an alkyl group having 1–4 carbon atoms, an aminoalkyl group having 1–4 carbon atoms, an alkanoyl group whose alkyl group has 1–6 carbon atoms that may be mono- or di-substituted with any group selected from the group consisting of a phenyl group, an alkoxycarbonyl group whose alkyl group has 1–4 carbon atoms and an optionally protected carboxyl group, a benzoyl group that may be mono- or di-substituted with any group selected from the group consisting of a halogen atom, a nitro group, an alkyl group having 1–4 carbon atoms, an alkoxy group having 1–4 carbon atoms, an optionally protected hydroxyl group, an optionally protected carboxyl group and an optionally protected amino group, an alkoxyoxalyl group whose alkyl group has 1 or 2 carbon atoms or a cycloalkylcarbonyl group whose cycloalkyl group has 3–6 carbon atoms) in the above-described inert aromatic hydrocarbon, a reaction-inert solvent such as a halogenated hydrocarbon, an ether or N,N-dimethylformamide or solvent systems consisting of mixtures of these solvents in the presence of a basic catalyst typified by tertiary amines such as triethylamine, pyridine, Dabco and DBU at a temperature ranging from −70° C. to the boiling point of the solvent, preferably from −30° C. to 100° C., thereby yielding a compound of the formula (I).

It is to be noted here that the compound of the formula (IVb) may have the oxime group modified by reaction with an alkyl halide having 1–4 carbon atoms that may be mono- or di-substituted with a phenyl group or a carboxyl group, an alkenyl halide having 2–4 carbon atoms, a benzyl halide that may be mono-substituted with an optionally protected carboxyl group in the phenyl moiety, an alkanoyl halide whose alkyl group has 1–4 carbon atoms, a benzoyl chloride or tosyl chloride.

The ketone derivative represented by the formula (IV) may be reacted with ammonium acetate or an alkylamine having 1–5 carbon atoms that may be substituted with a carboxyl or alkoxycarbonyl group in an inert aromatic hydrocarbon, an inert halogen-containing organic solvent such as dichloromethane or 1,2-dichloroethane, a reaction inert solvent such as an ether (e.g. diethyl ether, tetrahydrofuran or dioxane) or an alcoholic solvent (e.g. ethanol or methanol) or solvent systems consisting of mixtures of these solvents and subsequently treated with a reducing reagent such as sodium cyanoborohydride or sodium triacetoxyborohydride, optionally followed by alkali hydrolysis to yield a compound of the formula (I) in an amino or substituted amino derivative. The resulting amino derivative (Y and Z in the formula (I) represent a hydrogen atom and an amino group, respectively) may be reacted with a ketone such as acetone and subsequently reacted with a reducing reagent such as sodium cyanoborohydride, thereby yielding a compound of the formula (I) in a substituted amino form.

Alternatively, the compound of the formula (IV) may be reacted with a compound of the following formula (XIV):

(where $R^5$ represents an alkyl group having 1–4 carbon atoms or an aminoalkyl group having 1–4 carbon atoms) and subsequently reduced with a reducing reagent such as sodium borohydride or hydrogenated in the presence of a metal catalyst such as palladium or platinum oxide, thereby yielding a compound of the formula (I) in a substituted amino form.

A hydroxy derivative derived from the compound of the above-described formula (IV) may be placed in a reaction-inert solvent such as a halogen-containing organic solvent such as dichloromethane or an ether (e.g. diethyl ether or dioxane) or N,N-dimethylformamide, a basic solvent (e.g. pyridine or 4-dimethylaminopyridine) or solvent systems consisting of mixtures of these solvents at a temperature ranging from −70° C. to the boiling point of the solvent, preferably from −30° C. to 100° C. and are either converted to a halogeno form by treatment with a halogenating reagent such as hydrogen chloride, phosphorus trichloride, phosphorus pentachloride, phosphorus oxychloride or bromide corresponding thereto or treated with a suitable sulfonylating reagent such as mesyl chloride or tosyl chloride so that said hydroxy form is converted to the corresponding sulfonyloxy form, followed by reaction with ammonia or a compound of the formula (XIV) in the above-described inert aromatic hydrocarbon, reaction inert solvent such as a halogenated hydrocarbon or an ether or solvent systems consisting of mixtures of these solvents in the presence of a basic catalyst typified by tertiary amines such as triethylamine, pyridine, Dabco and DBU at a temperature ranging from −70° C. to the boiling point of the solvent, preferably from −30° C. to 100° C., thereby yielding a compound of the formula (I) in a substituted amino derivative.

The ketone derivative represented by the formula (IV) may be reacted with an alkylphosphonium salt having 1–4 carbon atoms that may be substituted with a carboxyl or alkoxycarbonyl group, or an alkylphosphonium salt having 1–5 carbon atoms that may be substituted with a hydroxyl group optionally substituted with an alkyl group having 1–4 carbon atoms, or corresponding alkylphosphonate esters in a reaction-inert solvent such as an ether (e.g. diethyl ether, tetrahydrofuran or dioxane) or N,N-dimethylformamide or solvent systems consisting of mixtures of these solvents at a temperature ranging from −70° C. to the boiling point of the solvent in the presence of a base such as sodium hydride, potassium hydroxide, potassium t-butoxide or butyl lithium, thereby yielding a compound of the formula (I). If necessary, hydrolysis or reduction with a reducing reagent such as sodium borohydride or hydrogenation in the presence of a metal catalyst such as palladium or platinum oxide or suitable combinations of these reactions may be performed to yield a compound of the formula (I) (these procedures may be grouped in reaction step B-3).

In addition to the above-described process, the following reaction step C may also be employed to produce compounds of the formula (I).

Reaction Step C

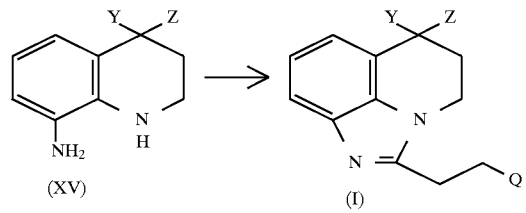

A compound of the formula (XV) that is produced by a method to be described below may be used as a starting material and reacted according to the above reaction step C with a compound represented by the following formula (VI):

[where Q has the same meaning as defined in the formula (I)], or a compound represented by the following formula (VII):

[where Q has the same meaning as defined in the formula (I) and R' represents a lower alkyl group], or a compound represented by the following formula (VIII):

[where Q has the same meaning as defined in the formula (I)], or a compound represented by the formula (IX):

[where Q has the same meaning as defined in the formula (I) and R' represents a lower alkyl group], or a compound represented by the following formula (X):

[where Q has the same meaning as defined in the formula (I)], or any other suitable compounds under appropriate reaction conditions. These reactions may be carried out in accordance with the methods described in Unexamined Published Japanese Patent Application Hei 3-27382 and WO93/22313. These references are incorporated into this specification.

The compound of the formula (XV) can be obtained by chemically modifying the carbonyl group in 8-amino-2,3-dihydro-4(1H)-quinolinone, which is a compound of the formula (V), in accordance with modifications of the above-described described reaction steps B-1 to B-3. The amino group in 8-amino-2,3-dihydro-4(1H)-quinolinone (V) may preliminarily be protected with any of the amino protecting groups to be described later during the reaction steps A to C.

If, during the reaction steps A to C, there is a reactive group such as a hydroxyl, amino, carboxyl or hydrazono group as a substituent Y, Z or Q, these groups may appropriately be protected in the course of reactions and the protective group may be removed at the final stage. The protective groups may be introduced and removed as appropriate depending on the type of the group to be protected and the protective group; for suitable methods that can be employed, reference may be made to T. W. Greene, "Protective Groups in Organic Synthesis", Wiley Company, 1981. This reference is incorporated into this specification.

Hydroxyl or carboxyl group may be protected with various groups including lower alkyl groups such as methyl, ethyl or t-butyl groups, and aralkyl groups such as benzyl or 4-nitrobenzyl groups, and lower alkyl groups are preferred from handling and reactivity viewpoints. Amino and hydrazono groups may be protected with groups such as trityl, tosyl, mesyl, formyl, chloroacetyl or t-butoxycarbonyl groups. A sulfo group may be protected with lower alkyl groups such as methyl, ethyl, or t-butyl groups.

If Y and Z differ in compounds represented by the formula (I), such compounds can provide optically active forms. Namely, the carbon to which Y and Z are bound becomes asymmetric and provides two enantiomers. Methods for obtaining the respective optical isomers are described in texts such as "Fusei Gosei to Kogaku Bunkatsu no Shinpo (Advances in Asymmetric Synthesis and Optical Resolution)", Ohtsuka and Mukaiyama (eds.), in Kagaku (Chemistry), Extra Issue No. 97, 1982, Kagaku Dojin Shuppan and "Kosentakuteki Hanno (Highly Selective Reactions)", Nozaki, Mukaiyama and Noyori, (eds.), in Kagaku (Chemistry), Extra Issue No. 91, 1981, Kagaku Dojin Shuppan and reference may be had to these texts; thus, optical isomers of compounds of the formula (I) can be obtained by asymmetric synthesis in accordance with known procedures. These references are incorporated into this specification. In the case of compounds of the formula (I) where Y is a hydrogen atom and Z is a hydroxyl group, the ketone form of the formula (VI) can be readily converted to an optically active hydroxyl form by the action of optically active organoboron reagents (e.g. diisopinocamphenylchloroborane), optically active organoaluminum reagents or baker's yeast. The resulting hydroxyl form may be converted to optically active ether and ester forms by the above-described procedures. In practice, derivatives with extremely high optical purity can be obtained by these procedures. Alternatively, said ketone form may first be converted to an oxime form as already described and then subjected to asymmetric reduction in the presence of a suitable catalyst such as a rhodium catalyst, thereby achieving conversion to an optically active amino form. The resulting optically active forms may, if necessary, be subjected to oxidation, reduction, hydrolysis or other reactions in the usual manner, thereby altering the functional groups.

If optically active forms represented by the formula (I) are obtained as mixtures, or racemates or compounds of low optical purity, they can be separated into the respective isomers by high-performance liquid chromatography (HPLC) using optical resolving columns such as CHIRALCEL OD™ and CHIRALPAK AD™ (in hexane/ethanol system), both being manufactured by DAICEL CHEMICAL IND. LTD. The resulting optically active forms may, if necessary, be subjected to oxidation, reduction, hydrolysis or other reactions in the usual manner, thereby altering the functional groups as appropriate. For instance, if compounds of the formula (I) are such that Y represents hydrogen atom, and Z represents the formula (III) where A represents an oxygen atom and $R^2$ represents a 2,3-bis(methoxycarbonyl) benzyl group, respectively, the mixture of the respective optically active forms can be separated by HPLC, then subjected to hydrolysis, thereby yielding optically active 2,3-dicarboxyl derivatives. Separation of these isomers can also be accomplished by optical resolution in accordance with known methods. For instance, the hydroxy derivative may be reacted with an optically active compound, (−)-4,7,7-trimethyl-3-oxo-2-oxabicyclo[2,2,]heptane-1-carbonyl chloride to give corresponding esters, which are separated by chromatography and hydrolyzed to yield the respective optical isomers.

If Y and Z in compounds of the formula (I) combine together to represent the following formula (II):

$$=N—OR^1 \quad (II)$$

(where $R^1$ represents an alkyl group having 1–4 carbon atoms that may be mono- or di-substituted with any group selected from between a phenyl and a carboxyl group, a tosyl group, an alkanoyl group whose alkyl group has 1–6 carbon atoms, a benzoyl group, an alkenyl group having 2–4 carbon atoms, or a benzyl group that may be monosubstituted with an optionally protected carboxyl group in the phenyl moiety), syn-anti isomers can exist. If compounds of the formula (I) are obtained as a mixture in the process of their synthesis, the mixture can be separated by high-performance liquid chromatography (HPLC) to yield the respective isomers. The isomers can be analyzed in terms of optical rotation or by nuclear magnetic resonance.

On the pages that follow, the activities of the compounds of the invention and the pharmaceutical compositions of the invention will be described in detail. As regards specific pharmacological actions, toxicity and other data, the activities of representative compounds are shown in the following cases of experiment but it should be understood that they are by no means intended to limit the invention.

Experiment 1: Activity on Mouse Intraperitoneal Hypereosinophilic Model

BALB/c male mice (body weight=ca. 25 g), divided in groups each consisting of five animals, were sensitized by intraperitoneal injection of physiological saline (0.11 mL) containing 0.1 mg of *Ascaris suum* extract. Seven days later, the same treatment was conducted; three days later, the animals were bled to death and injected intraperitoneally with 3 mL of physiological saline containing 1% dipotassium ethylenediaminetetraacetate (EDTA) and massaged on the abdominal part for about 30 sec. The abdominal part was incised to collect the intraperitoneal fluid, which was centrifuged at 130×g for 10 min. Fetal bovine serum (500 µl) containing 1% EDTA was added to the pellet to prepare a cell suspension. Part of the cell suspension was smeared on a glass slide with a centrifugal smearing device and subjected to Difquick staining. Thereafter, the total white blood cell (WBC) count and the eosinophil count were taken to determine the percentage of eosinophils in the total WBC. The total number of WBCs in the cell suspension was measured with an automatic hemocytometer. Multiplying the percentage of eosinophils in the total WBC by the total number of WBCs provided the number of eosinophils in the cell suspension.

Each of the test compounds was suspended in 5% aqueous gum arabic and administered perorally to mice immediately after the initial sensitization on a once-a-day basis for a total of 10 administrations (test compound-administered group). The mice neither sensitized nor administered the test compounds (untreated group), as well as the mice that were sensitized but not administered the test compounds (control group) were similarly administered 5% aqueous gum arabic perorally.

Test Compounds

Example 1: 4,5-dihydro-2-(2-phenylethyl)-6H-imidazo[4,5,1-ij]quinolin-6-one
Example 4: 5,6-dihydro-2-(2-phenylethyl)-4H-imidazo[4,5,1-ij]quinolin-6-ol
Example 11: (+)-5,6-dihydro-2-(2-phenylethyl)-4H-imidazo[4,5,1-ij]quinolin-6-ol
Example 13: 5,6-dihydro-2-(2-phenylethyl)-4H-imidazo[4,5,1-ij]quinoline
Example 18: 5,6-dihydro-2-(2-phenylethyl)-4H-imidazo[4,5,1-ij]quinolin-6-amine hydrochloride
Example 24: (+)-6-(2-carboxyphenyl)methoxy-5,6-dihydro-2-(2-phenylethyl)-4H-imidazo[4,5,1-ij]quinoline
Example 64: 6-(2,3-dicarboxyphenyl)methoxy-5,6-dihydro-2-(2-phenylethyl)-4H-imidazo[4,5,1-ij]quinoline
Prednisolone acetate: 11β, 17α, 21-trihydroxypregna-1,4-diene-3,20-dione 21-acetate The doses of the respective test compounds adminisered and the inhibition of the increase of intraperitoneal eosinophils as determined for each test compound by the following formula are shown in Table 1:

Inhibition of the Increase in Eosinophils (%)={1−(test compound administered group−untreated group)/(control group−untreated group)}×100

TABLE 1

| Test Compound (Example No.) | Dose (mg/kg/day) | Inhibition of the Increase of Eosinophils (%) |
| --- | --- | --- |
| 1 | 30 | 48 |
|   | 100 | 68 |
| 4 | 30 | 67 |
|   | 100 | 57 |
| 11 | 30 | 43 |
| 13 | 30 | 49 |
|   | 100 | 64 |
| 18 | 30 | 53 |
| 24 | 30 | 45 |
| 64 | 30 | 57 |
| Prednisolone Acetate | 10 | 65 |

Each of the compounds of the invention under test showed a marked activity in inhibiting the increase of intraperitoneal eosinophils in the BALB/c mice sensitized with the ascaris extract.

Experiment 2: Activity on Model for the Increase of Eosinophils in the Rat Bronchial Alveolar Lavage Fluid (BALF)

Sd male rats (8 wk old), divided in groups each consisting of five animals, were sensitized by an intravenous injection into tail vein of Sephadex G200 suspension (1 mL), that had been prepared to give a concentration of 0.75 mg/ml physiological saline. Seven days later, the same treatment was conducted; three days later, each rat was fitted with an tracheal cannula under anesthetization with pentobarbital and 7 mL of physiological saline containing 1% EDTA was injected via the cannula and recovered; this procedure was repeated three times to collect the BALF, which were centrifuged at 130×g for 10 min. Physiological saline (200 μl) containing 1% EDTA was added to the pellet to prepare a cell suspension. Part of the cell suspension was resuspended in fetal bovine serum containing 1% EDTA, smeared on a glass slide with a centrifugal smearing device and subjected to Difquick staining. Thereafter, the total WBC count and the eosinophil count were taken to determine the percentage of eosinophils in the total WBC. The total number of WBCs in the cell suspension was measured with a hemocytometer after staining with a Turck solution. Multiplying the percentage of eosinophils in the total WBC by the total number of WBCs provided the number of eosinophils in the cell suspension.

Each of the test compounds was suspended in 5% aqueous gum arabic and administered perorally to mice immediately after the initial sensitization on a once-a-day basis for a total of 10 administrations (test compound-treated group). The mice neither sensitized nor administered the test compounds (untreated group), as well as the mice that were sensitized but not administered the test compounds (control group) were similarly administered 5% aqueous gum arabic perorally.

Test Compounds

Example 1: 4,5-dihydro-2-(2-phenylethyl)-6H-imidazo[4,5,1-ij]quinolin-6-one
Example 4: 5,6-dihydro-2-(2-phenylethyl)-4H-imidazo[4,5,1-ij]quinolin-6-ol
Example 35: 5,6-dihydro-6-methoxyimino-2-(2-phenylethyl)-4H-imidazo[4,5,1-ij]quinoline The doses of the respective test compounds administered and the inhibition of the increase of eosinophils in the BALF as determined for each test compound by the following formula are shown in Table 2:

Inhibition of the Increase of Eosinophils (%)={1−(test compound administered group−untreated group)/(control group−untreated group)}×100

TABLE 2

| Test Compound (Example No.) | Dose (mg/kg/day) | Inhibition of the Increase of Eosinophils in BALF (%) |
| --- | --- | --- |
| 1 | 30 | 68 |
| 4 | 30 | 90 |
| Prednisolone Acetate | 10 | 76 |
| 35 | 30 | 73 |
| Prednisolone Acetate | 10 | 69 |

Each of the compounds of the invention under test showed a marked action in inhibiting the increase of eosinophils in the BALF in the SD rats sensitized with Sephadex G200.

Experiment 3: Experiment on Acute Toxicity

ICR male mice (body weight=ca. 35 g) weighing about 30 g were divided in groups each consisting of one or three animals and administered perorally each of the test compounds as suspended in 5% aqueous gum arabic. The mice were then examined for their survival until the 7th day of the administration.

Test Compounds

Example 1: 4,5-dihydro-2-(2-phenylethyl)-6H-imidazo[4,5,1-ij]quinolin-6-one
Example 4: 5,6-dihydro-2-(2-phenylethyl)-4H-imidazo[4,5,1-ij]quinolin-6-ol Example 13: 5,6-dihydro-2-(2-phenylethyl)-4H-imidazo[4,5,1-ij]quinoline Example 35: 5,6-dihydro-6-methoxyimino-2-(2-phenylethyl)-4H-imidazo[4,5,1-ij]quinoline Example 41: 5,6-dihydro-6-(o-carboxybenzoyloxy)-2-(2-phenylethyl)-4H-imidazo[4,5,1-ij]quinoline The doses of the respective test compounds administered and the number of rats that survived until the 7th day of the administration are shown in Table 3.

TABLE 3

| Test Compound (Example No.) | Dose (mg/kg) | No. of Survivals |
| --- | --- | --- |
| 1 | 1000 | 3 cases/3 cases |
| 4 | 1000 | 3 cases/3 cases |
| 13 | 1000 | 3 cases/3 cases |
| 35 | 1000 | 3 cases/3 cases |
| 41 | 1000 | 3 cases/3 cases |

None of the the compounds of the invention under test caused death in the ICR mice even when they were administered with 1,000 mg/kg.

As will be understood from the foregoing description and the experimental results, the compounds of the invention showed a great potency in inhibiting the increase of intraperitoneal eosinophils in the animal experimental model sensitized with the ascaris extract. The compounds of the invention also showed a great potency in inhibiting the increase of eosinophils in the BALF in the animal experimental model sensitized with Sephadex G200. In addition, the compounds of the invention exhibited satisfactory absorbability by oral route and their toxicity was extremely low, indicating their high safety features.

The compounds of the invention having an imidazoquinoline skeleton have a great potency in inhibiting the increase of eosinophils and their toxicity is extremely low featuring high safety. Therefore, they are anticipated to show effectiveness in preventing, alleviating and/or treating diseases that manifest the increase of eosinophils, with reduced side effects.

Since the compounds of the invention having an imidazoquinoline skeleton have a great potency in inhibiting the increase of eosinophils, they can be used in measures that are taken against diseases in which eosinophils are believed to participate in their pathophysiology as primary immunocytes, such as verminations, hypereosinophilic syndrome (HES), eosinophilic pneumonia, eosinophilic enterogastritis and bronchial asthma, said measures including the prevention of the diseases, retarding their onset, ensuring against the aggravation of their symptoms, amelioration of the symptoms and their treatment.

The compounds of the invention or salts thereof are typically administered perorally as drugs to the human and other animals but they can also be administered parenterally (e.g. intravenously, intramuscularly, subcutaneously, intrarectally, by transdermal absorption or by absorption through the mucosa).

The compounds of the invention or salts thereof may be administered on their own or, alternatively, they may be formulated into suitable pharmaceutical preparations in appropriate combinations with common suitable vehicles or media, such as excipients, binders, lubricants, coloring agents and flavoring agents, optionally used sterilized water or vegetable oils, physiologically acceptable solvents or solubilizers, as well as emulsifiers or suspending agents.

The formulations may assume various dosage forms including capsules, pills, tablets, granules, subtilized granules and powders, as well liquids for internal application such as suspensions, emulsions, medicated lemonades, elixirs and syrups, liquids for external application such as inhalants, aerosols and liniments, eye drops, nasal drops, plasters, ointments, lotions, liniments, cataplasms, suppositories, aqueous or non-aqueous injections, emulsifying or suspending injections, and solid injections that are dissolved, emulsified or suspended just prior to use.

The compounds of the invention, when formulated as drugs, are administered in amounts that are sufficient to treat the disease of interest but which are adjustable as appropriate for the dosage form of the therapeutic, method of administration, the number of administrations per day, the severity of the disease, the body weight of the patient and his or her age. The compounds of the invention, when formulated as drugs, are administered to adults at doses of 0.1–5,000 mg, preferably 1–500 mg, per day. For peroral administration to adults, the dose is 1–5,000 mg, preferably 1–300 mg. The daily administration may be single or divided in 2–6 portions.

The compounds of the invention may be used in combination with conventional therapeutics.

EXAMPLES

The following examples are provided for the purpose of further illustrating the invention.

Exemplary compounds of the invention that are represented by the formula (I), salts thereof, examples of their preparation and pharmaceutical formulations thereof will now be described specifically with reference to working examples but it should be noted that the invention is by no means limited to the following examples.

It should be noted that IR (infrared absorption) data were measured with potassium bromide tablets or thin films (designated "neat") and expressed in $cm^{-1}$. NMR data were those of nuclear magnetic resonance absorption at 90 MHz or 270 MHz (marked with *), which were measured at room temperature and expressed in ppm, with TMS (tetramethylsilane) as an internal standard. For the solvents used, $CDCl_3$ designates deuterochloroform, DMSO-d6 designates deuterodimethylsulfoxide and $CD_3OD$ designates deuteromethanol. The multiplicities of absorption lines were expressed as follows: s, singlet; d, doublet; t, triplet; q, quartet; dd, doublet of doublet; dt, doublet of triplet; m, multiplet; brs, broad singlet. The intensity of integrals is noted in parentheses. The optical rotation refers to specific rotation, which was measured at room temperature unless otherwise specified. For the solvents used, $CHCl_3$ designates chloroform and $CH_3OH$ designates methanol.

Example 1

Preparation of 4,5-dihydro-2-(2-phenylethyl)-6H-imidazo[4,5,1-ij]quinolin-6-one

Fifteen grams of 8-amino-2,3-dihydro-4(1H)-quinolinone was dissolved in methanol (300 mL), and after addition of 3-phenylpropionaldehyde (14.6 mL) and 1N HCl (3 mL), the mixture was stirred at room temperature for 2 hrs, followed by addition of silica gel (60 g) to the reaction mixture, and the solvent was removed under reduced pressure. The residue was heated at 100° C. for 2 hrs and purified by silica gel column chromatography (eluent: hexane/ethyl acetate) to yield the titled compound as yellow crystals (13.2 g).

m.p.: 111.8°–112.7° C.; IR: 1687, 1603, 1502, 1481, 1313, 1227, 1099, 806, 756, 700; NMR (*$CDCl_3$): 7.9 dd (1H), 7.7 dd (1H), 7.4–7.1 m (6H), 4.0 t (2H), 3.3–3.2 m(4H), 2.9 t (2H)

Example 2
Preparation of 4,5-dihydro-2-(2-phenylethyl)-6H-imidazo[4,5,1-ij]quinolin-6-one (compound of Example 1)

A hundred grams of 3-phenylpropionitrile was dissolved in anhydrous ether (200 mL), followed by addition of dry methanol (38 mL) and bubbling with hydrogen chloride gas. The reaction solution was stored overnight in a refrigerator and the precipitating crystals were collected by filtration with ether, yielding colorless crystals (152 g). The resulting crystals (15 g) and 8-amino-2,3-dihydro-4(1H)-quinolinone (10 g) were dissolved in acetic acid (50 mL) and heated under reflux for 8 hrs. The solvent was removed under reduced pressure and a saturated aqueous solution of sodium hydrogencarbonate was added to the residue, thereby making it alkaline. Following extraction with ethyl acetate, the organic layer was washed with saturated brine, then dried over anhydrous sodium sulfate. The solvent was removed under reduced pressure and the residue was purified by silica gel column chromatography to yield the titled compound as pale yellow crystals (7.0 g). The crystals thus obtained had spectrum data and a melting point that agreed with those obtained in Example 1.

Example 3
Preparation of 4,5-dihydro-2-(2-phenylethyl)-6H-imidazo[4,5,1-ij]-quinolin-6-one (compound of Example 1)

Thirty grams of 8-amino-2,3-dihydro-4(1H)-quinolinone was dissolved in anhydrous dichloromethane (450 mL); following the addition of triethylamine (38.7 mL), the mixture was cooled with ice and a solution of 3-phenylpropionyl chloride (46.9 g) in anhydrous dichloromethane (30 mL) was added dropwise over 35 min. Following 1.5 hr stirring on ice cooling, ice water (400 mL) was added to the reaction solution, and two layers were separated. The aqueous layer was extracted with dichloromethane and the organic layers were combined, washed with water and saturated brine successively, and dried over anhydrous sodium sulfate. The solvent was removed under reduced pressure and the residue was crystallized from ether and filtered to yield pale brown crystals (47.5 g). The resulting crystals (47.5 g) were suspended in toluene (950 mL) and, following the addition of p-toluenesulfonic acid monohydrate (36.9 g), the mixture was heated under reflux for 1 hr. After standing to cool, the solvent was removed under reduced pressure and the crystals were collected by filtration with ether. To the resulting crystals, dichloromethane (800 mL) and a saturated aqueous solution of sodium hydrogencarbonate (500 mL) were added, and two layers were separated. The aqueous layer was extracted with dichloromethane and the organic layers were combined and washed with water and saturated brine successively, followed by the addition of activated charcoal (4.8 g) and drying over anhydrous sodium sulfate. Both the activated charcoal and the drying agent were filtered off and the filtrate was concentrated under reduced pressure. The residue was crystallized from ether and hexane, and filtered to yield the titled compound as pale yellow crystals (39.4 g). The crystals thus obtained had spectrum data and a melting point that agreed with those obtained in Example 1.

Example 4
Preparation of 5,6-dihydro-2-(2-phenylethyl)-4H-imidazo[4,5,1-ij]quinolin-6-ol Fourteen grams of 4,5-dihydro-2-(2-phenylethyl)-6H-imidazo[4,5,1-ij]quinolin-6-one obtained in Example 1 was dissolved in dry methanol (140 mL); following the addition of sodium borohydride (0.76 g) under ice cooling and subsequent stirring at room temperature for 1 hr, the solvent was removed under reduced pressure and water was added to the residue, followed by extraction with dichloromethane. The organic layers were combined, washed with water and saturated brine successively, and dried over anhydrous sodium sulfate; thereafter, the solvent was removed under reduced pressure and the residue was purified by silica gel column chromatography (eluting solution: hexane/ethyl acetate) to yield the titled compound as colorless crystals (13.3 g).

m.p.: 124.9°–125.9° C.; IR: 3165, 1500, 1477, 1446, 1414, 752; NMR (*CDCl$_3$): 7.7–7.6 m (1H), 7.3–7.1 m (7H), 5.1 dd (1H), 3.9–3.7 m (2H), 3.2–3.0 m (4H), 2.3–2.2 m (1H), 2.0–1.9 m (1H)

Example 5
Preparation of 5,6-dihydro-2-(2-phenylethyl)-4H-imidazo[4,5,1-ij]quinolin-6-ol hydrochloride A portion (0.2 g) of 5,6-dihydro-2-(2-phenylethyl)-4H-imidazo[4,5,1-ij]quinolin-6-ol obtained in Example 4 was dissolved in ether (10 mL) and dichloromethane (10 mL); following the addition of 10% HCl-methanol solution (0.5 g), the solvents were removed under reduced pressure, followed by crystallization from ether; upon filtration, the titled compound was obtained as colorless crystals (0.23 g).

m.p.: 195.7°–198.3° C.; IR: 3342, 3309, 2771, 1491, 1456, 1090, 949, 760, 704; NMR (*DMSO-d$_6$): 7.7 dd (1H), 7.6–7.5 m (2H), 7.3–7.2 m (5H), 5.0 dd (1H), 4.4–4.2 m (2H), 3.5–3.4 m (2H), 3.3–3.2 m (2H), 2.3–2.0 m (2H)

Examples 6 and 7
Preparation of (+)-5,6-dihydro-2-(2-phenylethyl)-4H-imidazo[4,5,1-ij]quinolin-6-ol (Example 6) and (−)-5,6-dihydro-2-(2-phenylethyl)-4H-imidazo[4,5,1-ij]quinolin-6-ol

Example 7
(Step 1) Preparation of 5,6-dihydro-2-(2-phenylethyl)-6-((−)-4,7,7-trimethyl-3-oxo-2-oxabicyclo[2.2.1]heptane-1-carbonyloxy)-4H-imidazo[4,5,1-ij]quinoline After adding 60% sodium hydride (1.8 g) to dry N,N-dimethylformamide (130 mL) under an argon atmosphere, 10.5 g of 5,6-dihydro-2-(2-phenylethyl)-4H-imidazo[4,5,1-ij]quinolin-6-ol obtained in Example 4 was added slowly. After stirring for 30 min at room temperature, the mixture was cooled with ice and 12.2 g of (−)-4,7,7-trimethyl-3-oxo-2-oxabicyclo[2.2.1]heptane-1-carbonyl chloride was added slowly, followed by stirring at room temperature for 17 hrs. After adding water to the reaction solution, the mixture was extracted with ethyl acetate and the organic layer was dried over anhydrous sodium sulfate, followed by removing the solvent under reduced pressure; the residue was separated by medium-pressure liquid chromatography (eluent: Hexane/Ethanol/Diisopropylamine) to yield the diastereoisomers of the titled compound, which were a less polar fraction (2.8 g), a more polar fraction (3.7 g) and a mixture thereof (4.2 g).

less polar fraction m.p.: 143.6°–148.2° C.; IR: 2964, 1792, 1749, 1475, 1408, 1267, 1059, 756; NMR (*CDCl$_3$): 7.7 d (1H), 7.3–7.1 m (7H), 6.3 t (1H), 3.9–3.7 m (2H), 3.3–3.2 m (4H), 2.5–2.3 m (2H), 2.2–1.8 m (3H), 1.7–1.6 m (1H), 1.1 s (3H), 1.0 s (3H), 0.6 s (3H) Optical rotation ([α]Na589) : +112.2° (cl.17 CHCl$_3$)

more polar fraction m.p.: 143.8°–162.9° C.; IR: 2966, 1786, 1747, 1500, 1412, 1261, 1061, 756; NMR (*CDCl$_3$): 7.7 dd (1H), 7.3–7.1 m (7H), 6.3 t (1H), 3.9–3.7 m (2H), 3.3–3.2 m (4H), 2.4–2.3 m (2H), 2.2–1.6 m (4H), 1.1 s (3H), 0.9 s (6H); Optical rotation ([α]Na589): −124.1° (cl.64 CHCl$_3$)

(Step 2) Preparation of (+)-5,6-dihydro-2-(2-phenylethyl)-4H-imidazo[4,5,1-ij]quinolin-6-ol and (−)-5,6-dihydro-2-(2-phenylethyl)-4H-imidazo[4,5,1-ij]quinolin-6-ol A portion (2.7 g) of the less polar fraction of 5,6-dihydro-2-(2-phenylethyl)-6-((−)-4,7,7-trimethyl-3-oxo-2-oxabicyclo[2.2.1]heptane-1-carbonyloxy)-4H-imidazo[4,5,1-ij]quinoline obtained in Step 1 was dissolved in methanol (200 mL), followed by the addition of 2N aqueous sodium hydroxide (60 mL) and subsequent stirring at room temperature for 2 hrs; thereafter, the mixture was concentrated under reduced pressure and, to the residue was added water followed by extraction with ethyl acetate. The organic layer was washed with saturated brine, dried over anhydrous sodium sulfate, then the solvents was removed under reduced pressure, and the residue was recrystallized from acetone-hexane to yield the titled (+)-5,6-dihydro-2-(2-phenylethyl)-4H-imidazo[4,5,1-ij]quinolin-6-ol (1.2 g). The more polar fraction (3.7 g) was similarly treated to yield the titled (−)-5,6-dihydro-2-(2-phenylethyl)-4H-imidazo[4,5,1-ij]quinolin-6-ol (1.7 g).

(1) (+)-5,6-dihydro-2-(2-phenylethyl)-4H-imidazo[4,5,1-ij]quinolin-6-ol (Example 6)

m.p.: 151.8°–152.2° C.; IR: 3151, 1506, 1450, 1433, 1414, 1088, 754, 696; NMR (*CDCl$_3$): 7.7 dd (1H), 7.3–7.1 m (7H), 5.1–5.0 m (1H), 3.9–3.8 m (2H), 3.2–3.1 m (4H), 2.3–2.2 m (1H), 2.1–2.0 m (1H) Optical rotation ( [α]Hg577) : +18.7° (c1.004 CHCl$_3$)

(2) (−)-5,6-dihydro-2-(2-phenylethyl)-4H-imidazo[4,5,1-ij]quinolin-6-ol (Example 7)

m.p.: 151.8°–152.3° C.; IR: 3151, 1506, 1450, 1431, 1412, 1088, 754, 696; NMR (*CDCl$_3$): 7.7 dd (1H), 7.3–7.1 m (7H), 5.1–5.0 m (1H), 3.9–3.8 m (2H), 3.2–3.1 m (4H), 2.3–2.2 m (1H), 2.1–2.0 m (1H); Optical rotation ([α]Hg577) : −18.5° (c1.058 CHCl$_3$)

Example 8

Preparation of (+)-5,6-dihydro-2-(2-phenylethyl)-4H-imidazo[4,5,1-ij]quinolin-6-ol hydrochloride (+)-5,6-dihydro-2-(2-phenylethyl)-4H-imidazo[4,5,1-ij]quinolin-6-ol obtained in Example 6 was treated in the same manner as in Example 5 to yield the titled compound as colorless crystals.

m.p.: 143.0°–148.0° C.; IR: 3400, 3199, 3118, 1495, 1103, 804, 758; NMR (*DMSO-d$_6$): 7.7 dd (1H), 7.6–7.5 m (2H), 7.3–7.2 m (5H), 5.0 dd (1H), 4.4–4.2 m (2H), 3.5–3.4 m (2H), 3.3–3.2 m (2H), 2.3–2.0 m (2H); Optical rotation ( [α]Na589): +10.8° (c0.993 CH$_3$OH)

Example 9

Preparation of (−)-5,6-dihydro-2-(2-phenylethyl)-4H-imidazo[4,5,1-ij]quinolin-6-ol hydrochloride (−)-5,6-dihydro-2-(2-phenylethyl)-4H-imidazo[4,5,1-ij]quinolin-6-ol obtained in Example 7 was treated in the same manner as in Example 5 to yield the titled compound as colorless crystals.

m.p.: 144.0°–146.0° C.; IR: 3398, 3199, 3116, 1495, 1103, 804, 758; NMR (*DMSO-d$_6$): 7.7 dd (1H), 7.6–7.5 m (2H), 7.3–7.2 m (5H), 5.0 dd (1H), 4.4–4.2 m (2H), 3.5–3.4 m (2H), 3.3–3.2 m (2H), 2.3–2.0 m (2H); Optical rotation ([α]Na589): −10.4° (c0.228 CH$_3$OH)

Example 10

Preparation of (+)-5,6-dihydro-2-(2-phenylethyl)-4H-imidazo[4,5,1-ij]quinolin-6-ol hydrochloride (compound of Example 8)

(+)-Diisopinocanphenylchloroborane (5.26 g) was dissolved in dry tetrahydrofuran (10 mL) under an argon atmosphere. A portion (3.0 g) of the 4,5-dihydro-2-(2-phenylethyl)-6H-imidazo[4,5,1-ij]quinolin-6-one obtained in Example 1 was dissolved in 20 mL of dry tetrahydrofuran and the solution was added slowly at −20° C. to −25° C. After stirring for 3 hrs at the same temperature, the solvent was removed under reduced pressure. The residue was dissolved in ethyl acetate (40 mL) and, following the addition of diethanolamine (3.13 mL), the mixture was stirred at room temperature for 2 hrs. The precipitate was separated by filtration and washed with ethyl acetate; thereafter, the filtrate was concentrated. The residue was purified by silica gel column chromatography and converted to a hydrochloride salt by the same procedure as in Example 5, yielding 3.4 g of the titled compound with an optical purity of 80.2% ee. This hydrochloride salt was dissolved in hot ethanol and left to cool; the precipitating crystals were separated by filtration and the filtrate was concentrated to yield the titled compound with an optical purity of 92.4% ee as colorless crystals (2.7 g).

Example 11

Preparation of (+)-5,6-dihydro-2-(2-phenylethyl)-4H-imidazo[4,5,1-ij]quinolin-6-ol (compound of Example 6)

(+)-Diisopinocanphenylchloroborane (87.2 g) was dissolved in dry tetrahydrofuran (170 mL) under an argon atmosphere. Fifty grams of the 4,5-dihydro-2-(2-phenylethyl)-6H-imidazo[4,5,1-ij]quinolin-6-one obtained in Example 1 was dissolved in 340 mL of dry tetrahydrofuran and the solution was added slowly at −20° C. to −25° C. After stirring for 3 hrs at the same temperature, the solvent was removed under reduced pressure. The residue was dissolved in ethyl acetate (700 mL) and, following the addition of diethanolamine (52.2 mL), the mixture was stirred at room temperature for 2 hrs. The precipitate was separated by filtration and washed with ethyl acetate; thereafter, the filtrate was concentrated. The residue was purified by silica gel column chromatography to yield 40 g of the titled compound with an optical purity of 76.2% ee. The compound was recrystallized from a solvent system consisting of a mixture of ethanol (100 mL) and hexane (400 mL) to yield the titled compound with an optical purity of 99.6% ee or more as colorless crystals (17.4 g).

m.p.: 151.7°–152.6° C.; Optical rotation ([α]Na589): +18.9° (29.5° C., c1.009 CHCl$_3$)

The IR and NMR spectra data were identical to those obtained in Example 6. The optical purities were determined by HPLC (CHIRALPAK AD of DAICEL CHEMICAL IND., LTD.; 4.6×250 mm; hexane/ethanol=3/2).

Example 12

Preparation of (−)-5,6-dihydro-2-(2-phenylethyl)-4H-imidazo[4,5,1-ij]quinolin-6-ol (compound of Example 7)

(−)-Diisopinocanphenylchloroborane (87.2 g) was dissolved in dry tetrahydrofuran (170 mL) under an argon atmosphere. Fifty grams of 4,5-dihydro-2-(2-phenylethyl)-6H-imidazo[4,5,1-ij]quinolin-6-one obtained in Example 1 was dissolved in 340 mL of dry tetrahydrofuran and the solution was added slowly at −20° C. to −25° C. After stirring for 3 hrs at the same temperature, the solvent was removed under reduced pressure. The residue was dissolved in ethyl acetate (700 mL) and, following the addition of diethanolamine (52.2 mL), the mixture was stirred at room temperature for 2 hrs. The precipitate was separated by filtration and washed with ethyl acetate; thereafter, the filtrate was concentrated. The residue was purified by silica gel column chromatography to yield 40 g of the titled compound with an optical purity of 71.8% ee. The compound was recrystallized from a solvent system consisting of a mixture of ethanol (100 mL) and hexane (400 mL) to yield the titled compound with an optical purity of 99.6% ee or more as colorless crystals (19.9 g).

m.p.: 151.7°–152.2° C.; Optical rotation ([α]Na589): −18.5° (27.5° C., c1.023 CHCl$_3$)

The IR and NMR spectra data were identical to those obtained in Example 7. The optical purities were determined by HPLC (CHIRALPAK AD of DAICEL CHEMICAL IND., LTD.; 4.6×250 mm; hexane/ethanol=3/2).

Example 13

Preparation of 5,6-dihydro-2-(2-phenylethyl)-4H-imidazo[4,5,1-ij]quinoline

Thirty-five grams of 8-amino-1,2,3,4-tetrahydroquinoline was dissolved in methanol (700 mL) and, following the addition of 3-phenylpropionaldehyde (37.4 mL) and 1N HCl (7 mL) and subsequent stirring at room temperature for 1 hr, silica gel (75 g) was added to the reaction solution and the solvent was removed under reduced pressure. The residue was heated at 100° C. for 1 hr, purified by silica gel column chromatography (eluent: dichloromethane/ethyl acetate) and recrystallized with ethyl acetate to yield the titled compound as pale yellow crystals (19.3 g).

m.p.: 107.4°–108.3° C.; IR: 3022, 2953, 2937, 1502, 1408, 1263, 758, 702; NMR (*CDCl$_3$): 7.6 dd (1H), 7.3–7.1 m (6H), 7.0 dd (1H), 3.8 t (2H), 3.2–3.1 m (4H), 2.9 t (2H), 2.1–2.0 m (2H)

Example 14

Preparation of 5,6-dihydro-6-methylene-2-(2-phenylethyl)-4H-imidazo[4,5,1-ij]quinoline Methyltriphenylphosphonium bromide (1.29 g) was suspended in anhydrous tetrahydrofuran (10 mL) and a solution of potassium t-butoxide (0.45 g) in tetrahydrofuran (10 mL) was added dropwise at room temperature, followed by stirring for 1 hr at room temperature. Subsequently, 0.50 g of 4,5-dihydro-2-(2-phenylethyl)-6H-imidazo[4,5,1-ij]quinolin-6-one obtained in Example 1 was dissolved in anhydrous tetrahydrofuran (10 mL) and the solution was added dropwise and the mixture was stirred at room temperature for 1 hr. To the reaction solution, a saturated aqueous solution of sodium hydrogencarbonate (50 mL) and ethyl acetate (50 mL) were added and then two layers were separated. The organic layer was washed with saturated brine, dried over anhydrous sodium sulfate and concentrated under reduced pressure. The residue was purified by silica gel column chromatography (eluent: dichloromethane/ethyl acetate) to yield the titled compound as colorless crystals (0.41 g).

m.p.: 81.0°–82.2° C.; IR: 1498, 1404, 1248, 899, 750, 692; NMR (*CDCl$_3$): 7.6 d (1H), 7.4 d (1H), 7.3–7.1 m (6H), 5.7 s (1H), 5.2 d (1H), 3.8 t (2H), 3.3–3.1 m (4H), 2.8 t (2H)

Example 15

Preparation of 6-carboxymethylene-5,6-dihydro-2-(2-phenylethyl)-4H-imidazo[4,5,1-ij]quinoline A portion (3.2 g) of 4,5-dihydro-2-(2-phenylethyl)-6H-imidazo[4,5,1-ij]quinolin-6-one obtained in Example 1 was dissolved in anhydrous N,N-dimethylformamide (23 mL), followed by the addition of ethyl diethylphosphonoacetate (4.0 mL). After ice cooling under an argon atmosphere, 60% sodium hydride (0.79 g) was added portionwise and the mixture was stirred for 80 min under ice cooling, then for an additional 30 min at room temperature; thereafter, ice water (100 mL) was added to the reaction solution, followed by extraction with dichloromethane. The organic layer was washed with saturated brine and dried over anhydrous sodium sulfate; thereafter, the solvent was removed under reduced pressure and the residue was purified by silica gel column chromatography to yield an oil (2.64 g). A portion (0.64 g) of the oil and potassium hydroxide (150 mg) were dissolved in ethanol (5 mL) and the solution was stirred for 3 hrs at 40° C. To the reaction solution, water and ethyl acetate were added and then two layers were separated and conc. HCl was added to the aqueous layer to adjust its pH to 1, followed by extraction with ethyl acetate. The organic layer was washed with saturated brine and dried over anhydrous sodium sulfate. The solvent was removed under reduced pressure and the residue was washed with ethyl acetate and acetone to yield the titled compound as pale yellow crystals (140 mg).

m.p.: 204.0° C. - (with dec.) IR: 3028, 2929, 2501, 1693, 1595, 1497, 1412, 1323, 1200, 702; NMR (DMSO-d$_6$): 7.9 d (1H), 7.6 d (1H), 7.2–7.0 m (6H), 6.1 s (1H), 4.1 t (2H), 3.1 s (4H), 2.8 t (2H)

Example 16

Preparation of 4,5-dihydro-2-(2-phenylethyl)-6H-imidazo[4,5,1-ij]quinolin-6-one oxime carboxymethyl ether A portion (0.30 g) of 4,5-dihydro-2-(2-phenylethyl)-6H-imidazo[4,5,1-ij]quinolin-6-one obtained in Example 1 was suspended in ethanol (3 mL) and carboxymethoxyamine hemihydrochloride (0.24 g) and pyridine (0.088 mL) were added; following stirring for 65 hrs at room temperature, the precipitating crystals were collected by filtration and washed successively with ethanol and ether to yield the titled compound as slightly reddish white crystals (0.15 g).

m.p.: 198.0°–202.8° C.; IR: 3442, 2929, 1730, 1450, 1421, 1227, 1088; NMR (*DMSO-d$_6$): 7.6 d (1H), 7.4 d (1H), 7.3–7.1 m (6H), 4.7 s (2H), 4.2 t (2H), 3.2–3.1 m (6H)

Example 17

Preparation of 5,6-dihydro-2-(2-phenylethyl)-4H-imidazo[4,5,1-ij]quinolin-6-amine (Step 1) Preparation of 4,5-dihydro-2-(2-phenylethyl)-6H-imidazo[4,5,1-ij]quinolin-6-one oxime A portion (16 g) of 4,5-dihydro-2-(2-phenylethyl)-6H-imidazo[4,5,1-ij]quinolin-6-one obtained in Example 1 was suspended in ethanol (160 mL) and hydroxylamine hydrochloride (8.06 g) and pyridine (14.1 mL) were added; following stirring for 17 hrs at room temperature, the precipitating crystals were collected by filtration and washed successively with ethanol and ether to yield the titled compound as colorless crystals (12.0 g).

m.p.: 161.2°–173.3° C.; IR: 3111, 3028, 1495, 1456, 1362, 1022, 750; NMR (DMSO-d$_6$): 12.0 s (1H), 7.9–7.0 m (8H), 4.4 t (2H), 3.7–2.8 m (6H)

(Step 2) Preparation of 5,6-dihydro-2-(2-phenylethyl)-4H-imidazo[4,5,1-ij]quinolin-6-amine A portion (4.9 g) of 4,5-dihydro-2-(2-phenylethyl)-6H-imidazo[4,5,1-ij]quinolin-6-one oxime obtained in Step 1 was suspended in methanol (50 mL) and acetic acid (25 mL), followed by stirring at room temperature for 18 hrs under a hydrogen atmosphere in the presence of 10% palladium-carbon (0.5 g). The insoluble matter was separated by filtration with Celite® pad and the filtrate was concentrated; thereafter, the residue was dissolved in water and the pH of the solution was adjusted to about 8 with sodium hydrogencarbonate, followed by extraction with dichloromethane. The organic layers were combined, washed with saturated brine and dried over anhydrous sodium sulfate; the solvent was removed under reduced pressure and the residue was purified by silica gel column chromatography (eluent: dichloromethane/methanol) to yield the titled compound as pale yellow crystals (4.0 g).

m.p.: 43.6°–45.6° C.; IR: 3359, 1502, 1475, 1429, 1412, 797, 754, 704; NMR (*CDCl$_3$): 7.6 d (1H), 7.3–7.1 m (7H), 4.3 dd (1H), 3.9–3.7 m (2H), 3.2–3.1 m (4H), 2.2–2.1 m (1H), 2.0–1.9 m (1H)

Example 18
Preparation of 5,6-dihydro-2-(2-phenylethyl)-4H-imidazo[4,5,1-ij]quinolin-6-amine hydrochloride A portion (1.9 g) of 5,6-dihydro-2-(2-phenylethyl)-4H-imidazo[4,5,1-ij]quinolin-6-amine obtained in Step 2 of Example 17 was dissolved in methanol (20 mL) and 10% HCl-methanol solution (3.0 g) was added slowly. The solvent was removed under reduced pressure to yield the titled compound as colorless crystals (2.1 g).

m.p.: 240.0°–250.1° C.; IR: 2810, 1525, 1495, 1452, 1358, 754; NMR (*DMSO-$d_6$): 9.2 brs (3H), 7.8 d (1H), 7.7 d (1H), 7.5 t (1H), 7.3–7.2 m (5H), 4.8 brs (1H), 4.6–4.3 m (2H), 3.5 t (2H), 3.2 t (2H), 2.6–2.3 m (2H)

Example 19
Preparation of 5,6-dihydro-2-(2-phenylethyl)-6-(2-propylamino)-4H-imidazo[4,5,1-ij]quinoline A portion (1.0 g) of 5,6-dihydro-2-(2-phenylethyl)-4H-imidazo[4,5,1-ij]quinolin-6-amine obtained in step 2 of Example 17 was dissolved in methanol (10 mL) and, following the addition of acetone (0.53 mL) and 10% HCl-methanol solution (0.1 mL), the mixture was stirred at room temperature for 4 days. The reaction solution was cooled with ice and, following the addition of sodium cyanoborohydride (0.23 g), the mixture was stirred at room temperature for 24 hrs. The reaction mixture was concentrated and, to the residue was added water followed by extraction with ethyl acetate; the organic layer was washed with saturated brine and dried over anhydrous sodium sulfate. The solvent was removed under reduced pressure and the residue was purified by silica gel column chromatography (eluent: dichloromethane/methanol) to yield the titled compound as pale yellow crystals (0.80 g).

m.p.: 95.5°–97.7° C.; IR: 2962, 2924, 1497, 1448, 1416, 1331, 748, 704; NMR (*CDCl$_3$): 7.6 dd (1H), 7.3–7.1 m (7H), 4.1 t (1H), 3.9–3.7 m (2H), 3.2–3.0 m (5H), 2.1–2.0 m (2H), 1.2 d (3H), 1.1 d (3H)

Example 20
Preparation of 5,6-dihydro-6-methoxy-2-(2-phenylethyl)-4H-imidazo[4,5,1-ij]quinoline A portion (115 mg) of 60% sodium hydride was added to anhydrous tetrahydrofuran (15 mL) under an argon atmosphere; 0.2 g of 5,6-dihydro-2-(2-phenylethyl)-4H-imidazo[4,5,1-ij]quinolin-6-ol obtained in Example 4 was dissolved in anhydrous tetrahydrofuran (4 mL) and the solution was added dropwise to the first mentioned solution at room temperature. After stirring for 35 min at room temperature, methyl iodide (1.02 g) was added dropwise and the mixture was stirred for 4 hrs. Water was added to the reaction solution and the mixture was stirred; thereafter, the reaction solution was extracted with dichloromethane, washed with saturated brine and dried over anhydrous sodium sulfate. The solvent was removed under reduced pressure and the residue was purified by silica gel column chromatography (eluent: hexane/ethyl acetate) to yield the titled compound as a yellow oil (103 mg).

IR (neat): 3354, 2929, 1651, 1605, 1502, 1450, 1412, 1093, 752, 702; NMR (CDCl$_3$): 7.7 dd (1H), 7.3–7.1 m (7H), 4.5 t (1H), 4.0–3.8 m (2H), 3.4 s (3H), 3.2 s (4H), 2.5–1.9 m (2H)

Example 21
Preparation of 5,6-dihydro-6-(2-methoxycarbonylphenyl)methoxy-2-(2-phenylethyl)-4H-imidazo[4,5,1-ij]quinoline A portion (1.15 g) of 60% sodium hydride was added to 50 mL of anhydrous N,N-dimethylformamide (DMF) in an argon atmosphere; 2.0 g of 5,6-dihydro-2-(2-phenylethyl)-4H-imidazo[4,5,1-ij]quinolin-6-ol obtained in Example 4 was dissolved in anhydrous DMF (40 mL) and the solution was added dropwise to the first mentioned solution at room temperature. After stirring for 1 hr at room temperature, a solution of methyl o-bromomethylbenzoate (6.6 g) in anhydrous DMF (40 mL) was added dropwise and the mixture was stirred for 1 hr. The reaction solution was poured into ice water (500 mL), and extracted with ethyl acetate, the organic layer was washed with saturated brine and dried over anhydrous sodium sulfate. The solvent was removed under reduced pressure and the residue was purified by silica gel column chromatography (eluent: hexane/ethyl acetate) to yield the titled compound as a yellow oil (2.38 g).

IR (neat): 2951, 1716, 1265, 1070, 750; NMR (*DMSO-$d_6$): 7.8 d (1H), 7.6–7.4 m (4H), 7.3–7.1 m (7H), 5.0 d (1H), 4.9 d (1H), 4.8 t (1H), 4.3–4.2 m (1H), 4.0–3.9 m (1H), 3.7 s (3H), 3.2–3.1 m (4H), 2.4–2.3 m (1H), 2.1–2.0 m (1H)

Example 22
Preparation of 6-(2-carboxyphenyl)methoxy-5,6-dihydro-2-(2-phenylethyl)-4H-imidazo[4,5,1-ij]quinoline Ethanol (4 mL) was added to 0.62 g of the 5,6-dihydro-6-(2-methoxycarbonylphenyl)methoxy-2-(2-phenylethyl)-4H-imidazo[4,5,1-ij]quinoline obtained in Example 19; to the solution, another solution having potassium hydroxide (0.19 g) dissolved in water (0.4 mL) was added and the mixture was heated under reflux for 1 hr. After standing to cool, the reaction solution was poured into water and its pH was adjusted to 4–5 using 10% aqueous citric acid; after extraction with ethyl acetate, the organic layer was washed with saturated brine and dried over anhydrous sodium sulfate. The solvent was removed under reduced pressure and the residue was purified by silica gel column chromatography (eluent: ethyl acetate) to yield the titled compound as pale yellow crystals (0.37 g).

m.p.: 206.1°–215.2° C.; IR: 2890, 1686, 1605, 1477, 1444, 1140, 1066, 756; NMR (*DMSO-$d_6$): 7.8 d (1H), 7.6–7.5 m (3H), 7.4–7.1 m (8H), 5.1 d (1H), 4.9 d (1H), 4.8 brs (1H), 4.3–4.1 m (1H), 4.0–3.9 m (1H), 3.2–3.1 m (4H), 2.4–2.3 m (1H), 2.1–2.0 m (1H)

Example 23
Preparation of (+)-5,6-dihydro-6-(2-methoxycarbonylphenyl)methoxy-2-(2-phenylethyl)-4H-imidazo[4,5,1-ij]quinoline A portion (10.0 g) of (+)-5,6-dihydro-2-(2-phenylethyl)-4H-imidazo[4,5,1-ij]quinolin-6-ol obtained in Example 11 was treated in the same manner as in Example 21 to yield the titled compound as a pale yellow oil (13.4 g).

IR (neat): 2951, 1718, 1265, 1070, 750; NMR (*DMSO-$d_6$): 7.8 d (1H), 7.6–7.1 m (11H), 5.0 d (1H), 4.9 d (1H), 4.8 t (1H), 4.3–4.2 m (1H), 4.0–3.9 m (1H), 3.7 s (3H), 3.2–3.1 m (4H), 2.4–2.3 m (1H), 2.1–2.0 m (1H); Optical rotation ([α]Na589) : +82.7° (28.4° C., c0.954 CHCl$_3$)

Example 24
Preparation of (+)-6-(2-carboxyphenyl)methoxy-5,6-dihydro-2-(2-phenylethyl)-4H-imidazo[4,5,1-ij]quinoline A portion (13.1 g) of (+)-5,6-dihydro-6-(2-methoxycarbonylphenyl)methoxy-2-(2-phenylethyl)-4H-imidazo[4,5,1-ij]quinoline obtained in Example 23 was treated in the same manner as in Example 22 to yield the titled compound as colorless crystals (10.9 g).

m.p.: 153.5°–154.9° C.; IR: 3423, 2875, 1701, 1477, 1450, 1259, 1074, 746; NMR (*DMSO-$d_6$): 7.9 d (1H), 7.6–7.5 m (3H), 7.4–7.1 m (8H), 5.1 d (1H), 4.9 d (1H), 4.8 t (1H), 4.3–4.1 m (1H), 4.0–3.9 m (1H), 3.2–3.1 m (4H), 2.4–2.3 m (1H), 2.1–2.0 m (1H); Optical rotation ([α]Na589) : +97.2° (28.0° C., c0.994 CHCl$_3$)

Example 25
Preparation of (−)-5,6-dihydro-6-(2-methoxycarbonylphenyl)methoxy-2-(2-phenylethyl)-4H-imidazo[4,5,1-ij]quinoline A portion (10.0 g) of (−)-5,6-dihydro-2-(2-phenylethyl)-4H-imidazo[4,5,1-ij]quinolin-6-ol obtained in Example 12 was treated in the same manner as in Example 21 to yield the titled compound as a pale yellow oil (12.5 g).

IR (neat): 2951, 1718, 1265, 1070, 750; NMR (*DMSO-d$_6$): 7.8 d (1H) , 7.6–7.1 m (11H) , 5.0 d (1H) 4.9 d (1H), 4.8 t (1H), 4.3–4.2 m (1H), 4.0–3.9 m (1H), 3.7 s (3H), 3.2–3.1 m (4H), 2.4–2.3 m (1H), 2.1–2.0 m (1H); Optical rotation ([α]Na589) : −80.5° (28.0° C., c0.814 CHCl$_3$)

Example 26
Preparation of (−)-6-(2-carboxyphenyl)methoxy-5,6-dihydro-2-(2-phenylethyl)-4H-imidazo[4,5,1-ij]quinoline A portion (12.1 g) of (−)-5,6-dihydro-6-(2-methoxycarbonylphenyl)methoxy-2-(2-phenylethyl)-4H-imidazo[4,5,1-ij]quinoline obtained in Example 25 was treated in the same manner as in Example 22 to yield the titled compound as colorless crystals (10.3 g).

m.p.: 153.3°–154.0° C.; IR: 3423, 2875, 1701, 1477, 1450, 1261, 1074, 746; NMR (*DMSO-d$_6$): 13.0 brs (1H), 7.8 d (1H), 7.6–7.5 m (3H), 7.4–7.1 m (8H), 5.1 d (1H), 4.9 d (1H), 4.8 t (1H), 4.3–4.1 m (1H), 4.0–3.9 m (1H), 3.2–3.1 m (4H), 2.4–2.3 m (1H), 2.1–2.0 m (1H); Optical rotation ([α]Na589): −98.1° (28.0° C., c0.878 CHCl$_3$)

Example 27
Preparation of 5,6-dihydro-2-(2-phenylethyl)-6-(2-pyridinecarboxamido)-4H-imidazo[4,5,1-ij]quinoline A portion (0.4 g) of the 5,6-dihydro-2-(2-phenylethyl)-4H-imidazo[4,5,1-ij]quinolin-6-amine obtained in Step 2 of Example 17 was dissolved in anhydrous dichloromethane (5 mL); following the addition of pyridine (0.26 mL), picolinoyl chloride hydrochloride (0.28 g) was added under cooling with ice. After stirring for 4 hrs at room temperature, water (50 mL) and dichloromethane (50 mL) were added to the reaction solution and then two layers were separated, and the aqueous layer was extracted with dichloromethane. The organic layers were combined, washed with saturated brine and dried over anhydrous sodium sulfate. The solvent was removed under reduced pressure and the residue was purified by silica gel column chromatography (eluent: ethyl acetate) to yield the titled compound as pale brown crystals (0.31 g).

m.p.: 173.0° C. - (dec.); IR: 3398, 3053, 1676, 1508, 1433, 1410, 752, 704; NMR (*DMSO-d$_6$): 9.0 d (1H), 8.6 d (1H), 8.1 d (1H), 8.0 t (1H), 7.6 dd (1H), 7.4 d (1H), 7.3–7.2 m (5H), 7.1 t (1H), 7.0 d (1H), 5.6–5.5 m (1H), 4.2–4.0 m (2H), 3.2–3.1 m (4H), 2.4–2.2 m (2H)

Example 28
Preparation of 5,6-dihydro-2-(2-phenylethyl)-4H-imidazo[4,5,1-ij]quinoline-6-thiol A portion (5.55 g) of 5,6-dihydro-2-(2-phenylethyl)-4H-imidazo[4,5,1-ij]quinolin-6-ol obtained in Example 4 was suspended in xylene (700 mL); following the addition of a Lawesson reagent (4.04 g), the suspension was heated under reflux for 30 min under an argon atmosphere. After standing to cool, the supernatant was concentrated under vacuum and the residue was purified by silica gel column chromatography (eluent: toluene/ethyl acetate) to yield the titled compound as colorless crystals (0.91 g).

m.p.: 75.7°–78.8° C.; IR: 3433, 3028, 2924, 1498, 1471, 1410, 748, 702; NMR (*DMSO-d$_6$): 7.4–7.1 m (8H), 4.5 brs (1H), 4.2–4.0 m (2H), 3.2–3.1 m (4H), 2.4–2.3 m (1H), 2.2–2.1 m (1H)

Example 29
Preparation of 5,6-dihydro-6-methylthio-2-(2-phenylethyl)-4H-imidazo[4,5,1-ij]quinoline The mixture of 60% sodium hydride (245 mg) and anhydrous tetrahydrofuran (20 mL) under an argon atmosphere was added dropwise the solusion of 5,6-dihydro-2-(2-phenylethyl)-4H-imidazo[4,5,1-ij]quinoline-6-thiol (0.45 g) obtained in Example 28 in anhydrous tetrahydrofuran (20 mL) at room temperature. After stirring for 1 hr at room temperature, methyl iodide (0.95 mL) was added dropwise and the mixture was stirred for 30 min. Ice water was added to the reaction solution and stirred; thereafter, the mixture was extracted with ethyl acetate and the organic layer was washed with saturated brine and dried over anhydrous sodium sulfate. The solvent was removed under reduced pressure and the residue was purified by silica gel column chromatography (eluent: hexane/ethyl acetate) to yield the titled compound as colorless crystals (356 mg).

m.p.: 62.1°–74.1° C.; IR: 2927, 1502, 1408, 748, 702; NMR (*DMSO-d$_6$): 7.4 dd (1H), 7.3–7.2 m (5H), 7.1–7.0 m (2H), 4.3 t (1H), 4.2–4.1 m (1H), 4.1–4.0 m (1H), 3.2–3.1 m (4H), 2.3–2.2 m (2H), 2.1 s (3H)

In Examples 30–42, 48–94 and 109–126, the compounds were prepared by modifications of the production process according to Reaction Step B. In Examples 43–47 and 95–108, the compounds were prepared by modifications of the production process according to Reaction Step A.

Examples 127 and 128
Preparation of (+)-5,6-dihydro-6-(2,3-bis(methoxycarbonyl)phenyl)methoxy-2-(2-phenylethyl)-4H-imidazo[4,5,1-ij]quinoline Example 127) and (−)-5,6-dihydro-6-(2,3-bis(methoxycarbonyl)phenyl)methoxy-2-(2-phenylethyl)-4H-imidazo[4,5,1-ij]quinoline Example 128)

A portion (0.31 g) of 5,6-dihydro-6-(2,3-bis(methoxycarbonyl)phenyl)methoxy-2-(2-phenylethyl)-4H-imidazo[4,5,1-ij]quinoline obtained in Example 123 was separated by high-performance liquid chromatography (CHIRALCEL OD of DAICEL CHEMICAL IND., LTD.; eluent: hexane/ethanol) to yield the titled (+)-5,6-dihydro-6-(2,3-bis(methoxycarbonyl)phenyl)methoxy-2-(2-phenylethyl)-4H-imidazo[4,5,1-ij]quinoline (0.110 g) as the more polar fraction and the titled (−)-5,6-dihydro-6-(2,3-bis(methoxycarbonyl)phenyl)methoxy-2-(2-phenylethyl)-4H-imidazo[4,5,1-ij]quinoline (0.105 g) as the less polar fraction.

(1) (+)-5,6-dihydro-6-(2,3-bis(methoxycarbonyl)phenyl)methoxy-2-(2-phenylethyl)-4H-imidazo[4,5,1-ij]quinoline

Example 127)

IR: 2951, 1722, 1284, 752; NMR (*CDCl$_3$): 7.9 dd (1H), 7.7 d (1H), 7.6 d (1H), 7.4 t (1H), 7.3–7.1 m (7H), 4.7–4.6 m (3H), 4.0–3.8 m (2H), 3.9 s (3H), 3.7 s (3H), 3.2–3.1 m (4H), 2.4–2.3 m (1H), 2.0–1.9 m (1H); Optical rotation ([α]Na589): +65.6° (28.7° C., c1.10 CHCl$_3$)

(2) (−)-5,6-dihydro-6-(2,3-bis(methoxycarbonyl)phenyl) methoxy-2-(2-phenylethyl)- 4H-imidazo[4,5,1-ij]quinoline Example 128)

IR: 2951, 1730, 1286, 754; NMR (*CDCl$_3$): 7.9 dd (1H), 7.7 d (1H), 7.6 d (1H), 7.4 t (1H), 7.3–7.1 m (7H), 4.7–4.6 m (3H), 4.0–3.8 m (2H), 3.9 s (3H), 3.7 s (3H), 3.2–3.1 m (4H), 2.4–2.3 m (1H), 2.0–1.9 m (1H); Optical rotation ([α]Na589): −69.4° (28.0° C., c1.05 CHCl$_3$)

The melting points of the compounds in the examples, as well as their IR and NMR spectrum data are listed collectively in Table 4.

Figure 2:
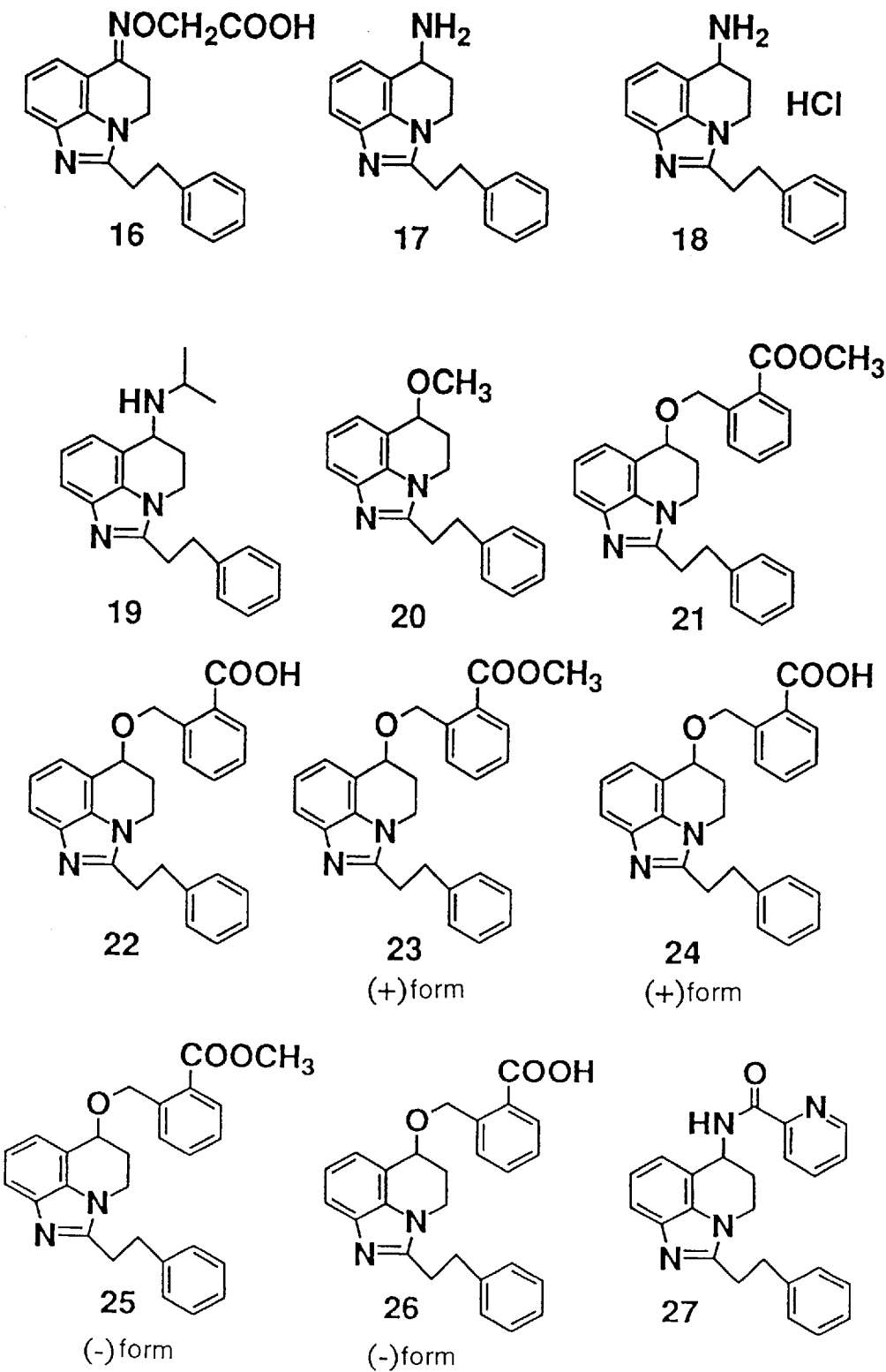
FIG. 2 is a drawing that gives chemical formulae describing the structures of the imidazoquinoline derivatives prepared in Examples 16–27.
Figure 3:
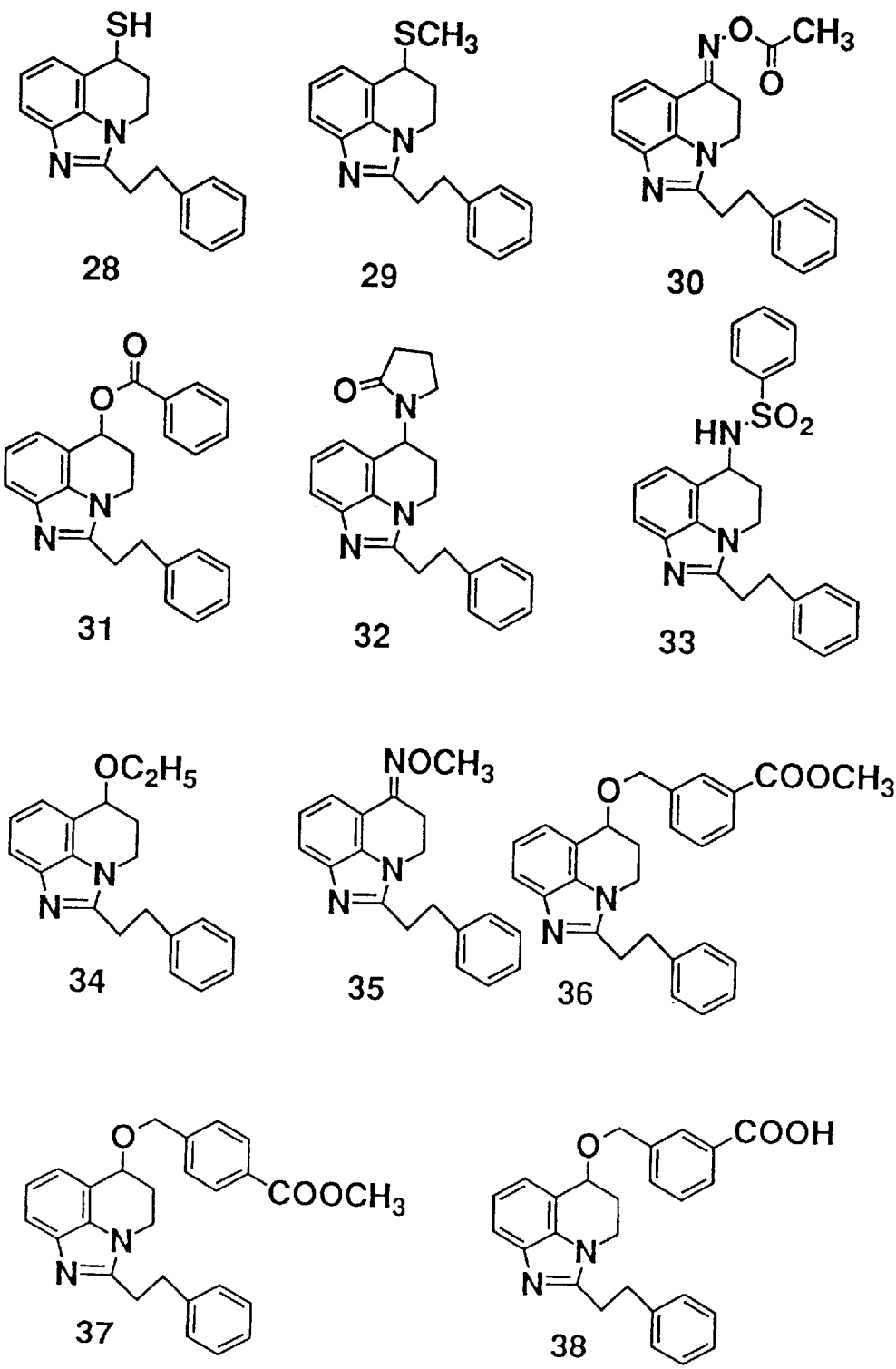
FIG. 3 is a drawing that gives chemical formulae describing the structures of the imidazoquinoline derivatives prepared in Examples 28–38.
Figure 4:
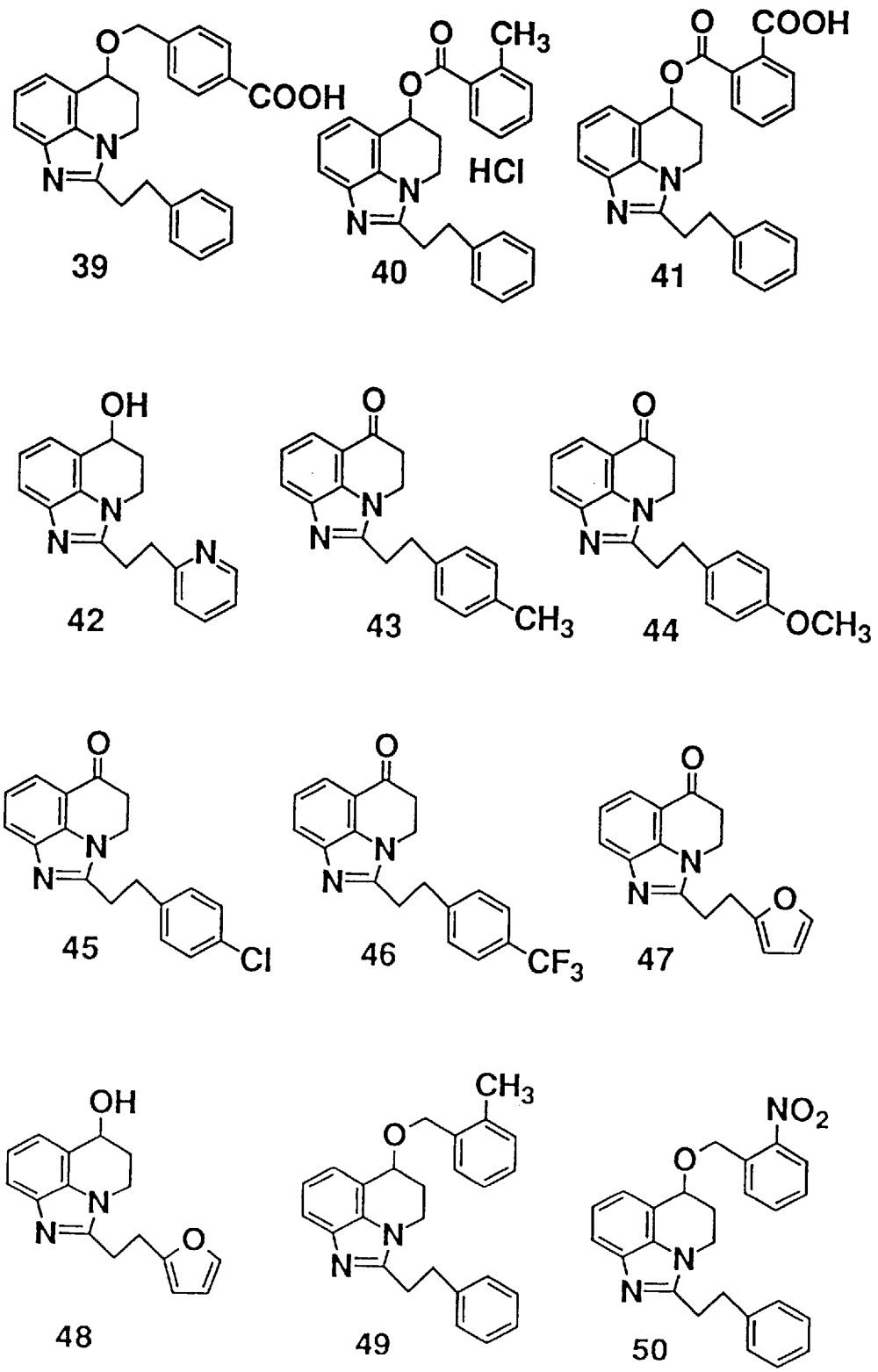
FIG. 4 is a drawing that gives chemical formulae describing the structures of the imidazoquinoline derivatives prepared in Examples 39–50.
Figure 5:
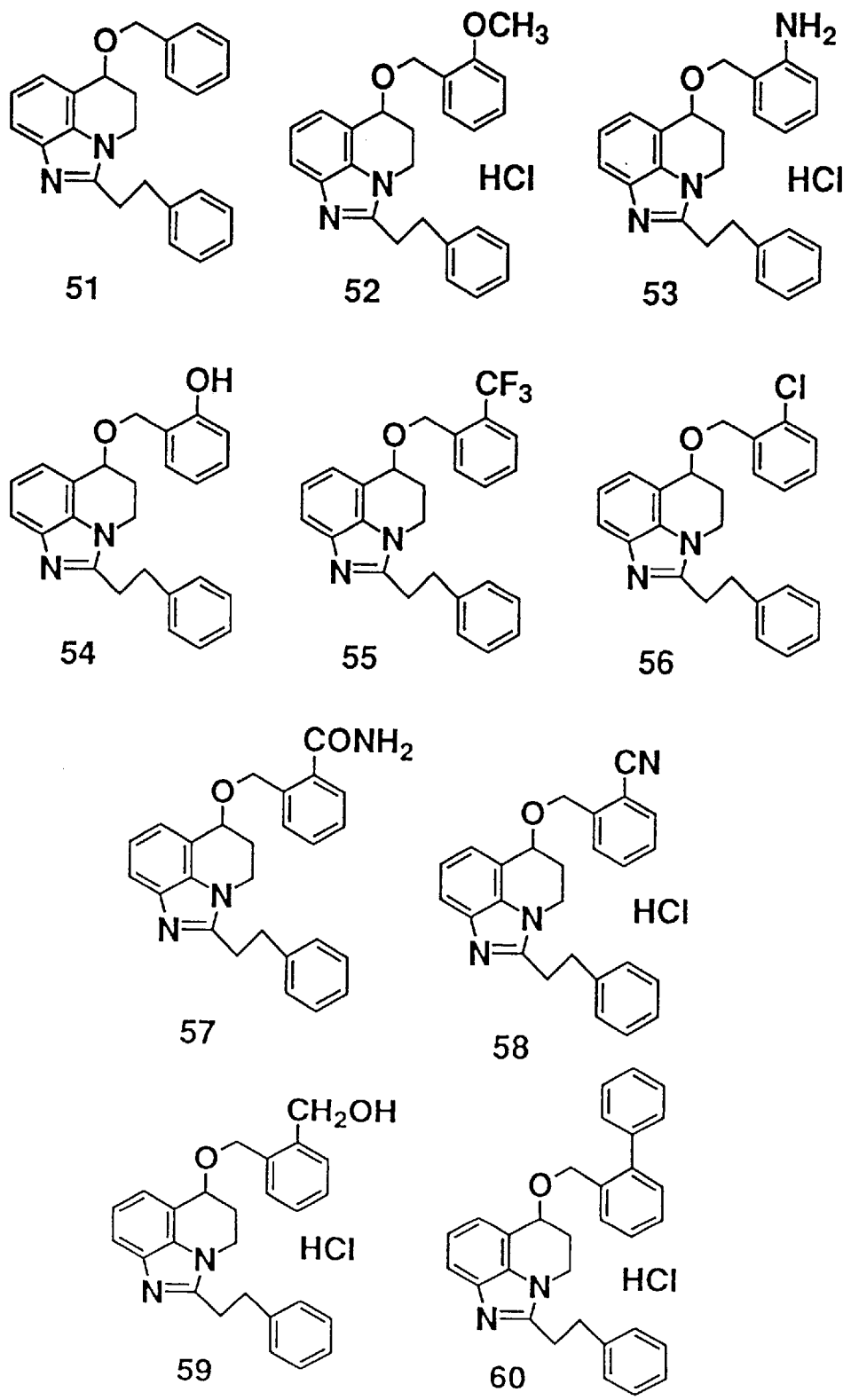
FIG. 5 is a drawing that gives chemical formulae describing the structures of the imidazoquinoline derivatives prepared in Examples 51–60.
Figure 6:
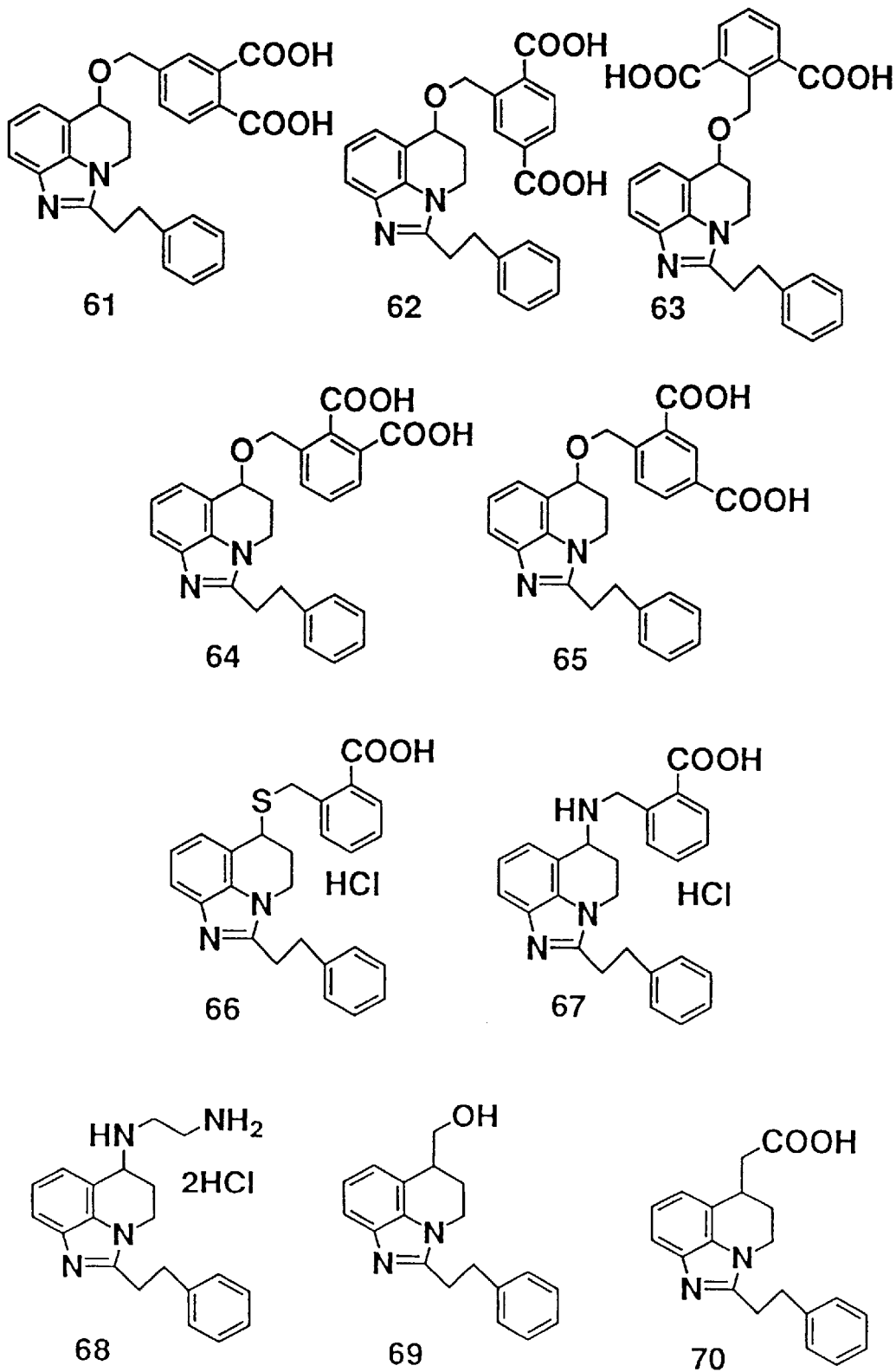
FIG. 6 is a drawing that gives chemical formulae describing the structures of the imidazoquinoline derivatives prepared in Examples 61–70.
Figure 7:
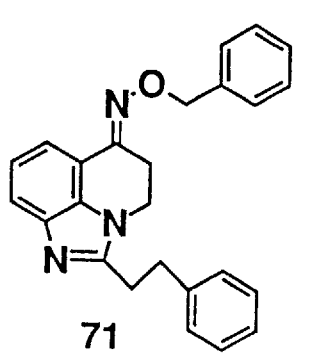
FIG. 7 is a drawing that gives chemical formulae describing the structures of the imidazoquinoline derivatives prepared in Examples 71–82.
Figure 7:
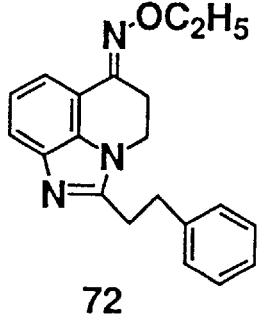
Figure 7:
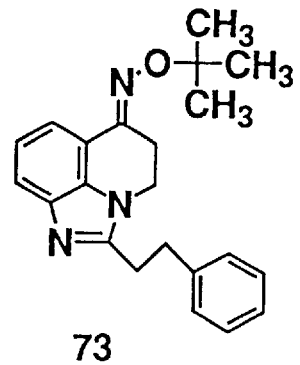
Figure 7:
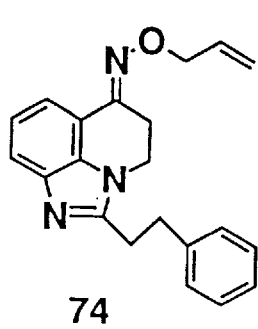
Figure 7:
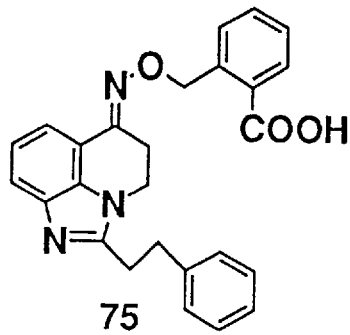
Figure 7:
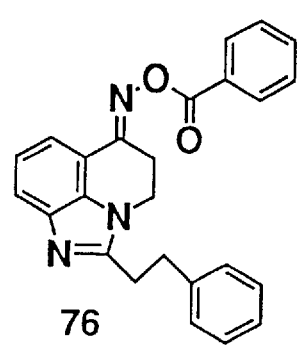
Figure 7:
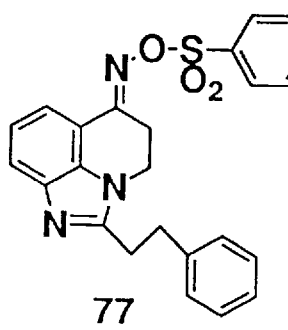
Figure 7:
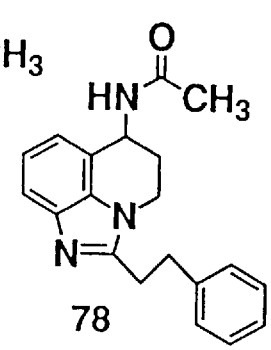
Figure 7:
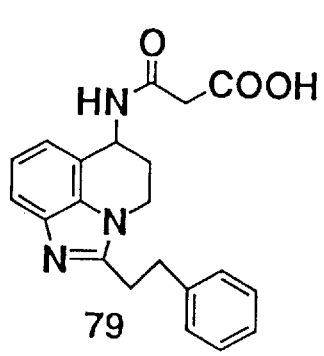
Figure 7:
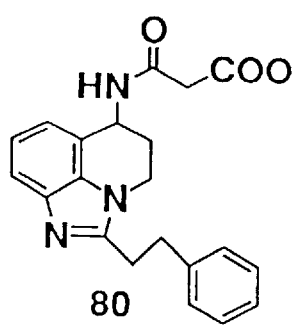
Figure 7:
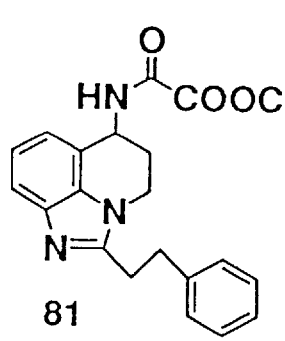
Figure 7:
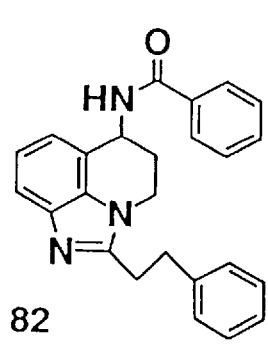
Figure 8:
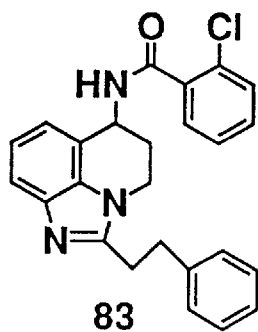
FIG. 8 is a drawing that gives chemical formulae describing the structures of the imidazoquinoline derivatives prepared in Examples 83–94.
Figure 8:
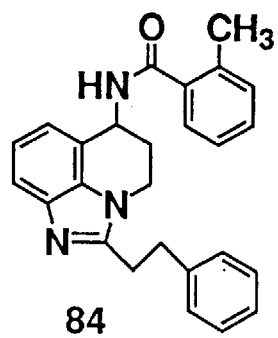
Figure 8:
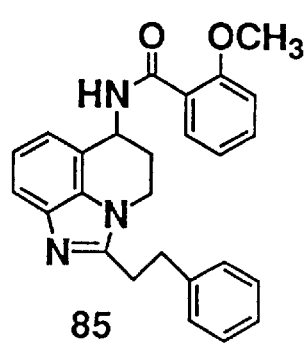
Figure 8:
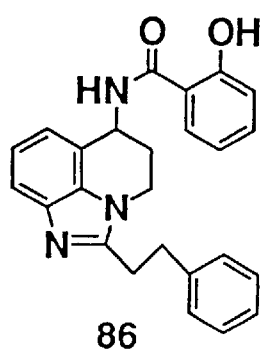
Figure 8:
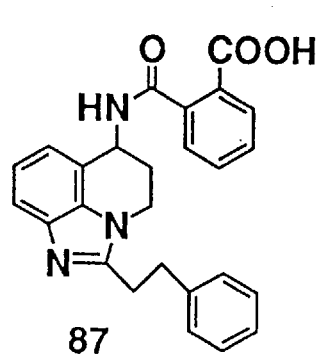
Figure 8:
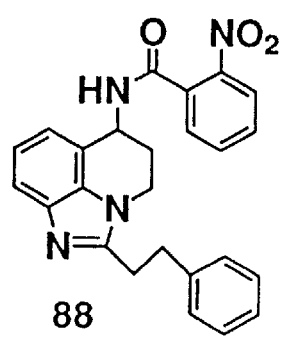
Figure 8:
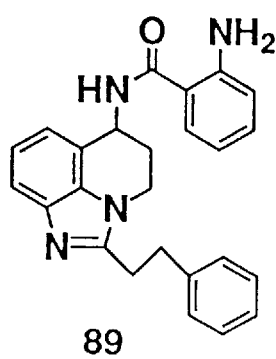
Figure 8:
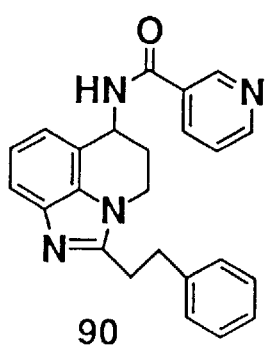
Figure 8:
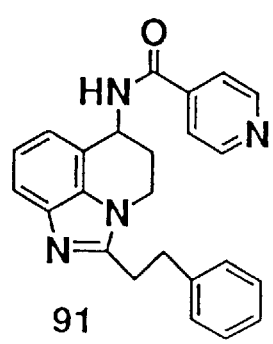
Figure 8:
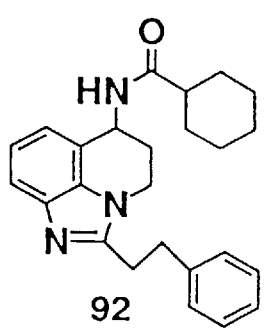
Figure 8:
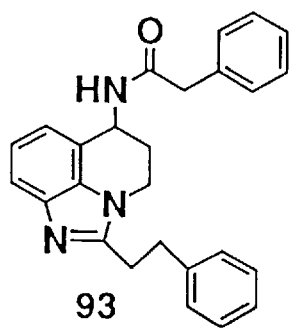
Figure 8:
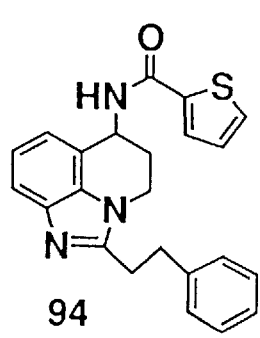
Figure 9:
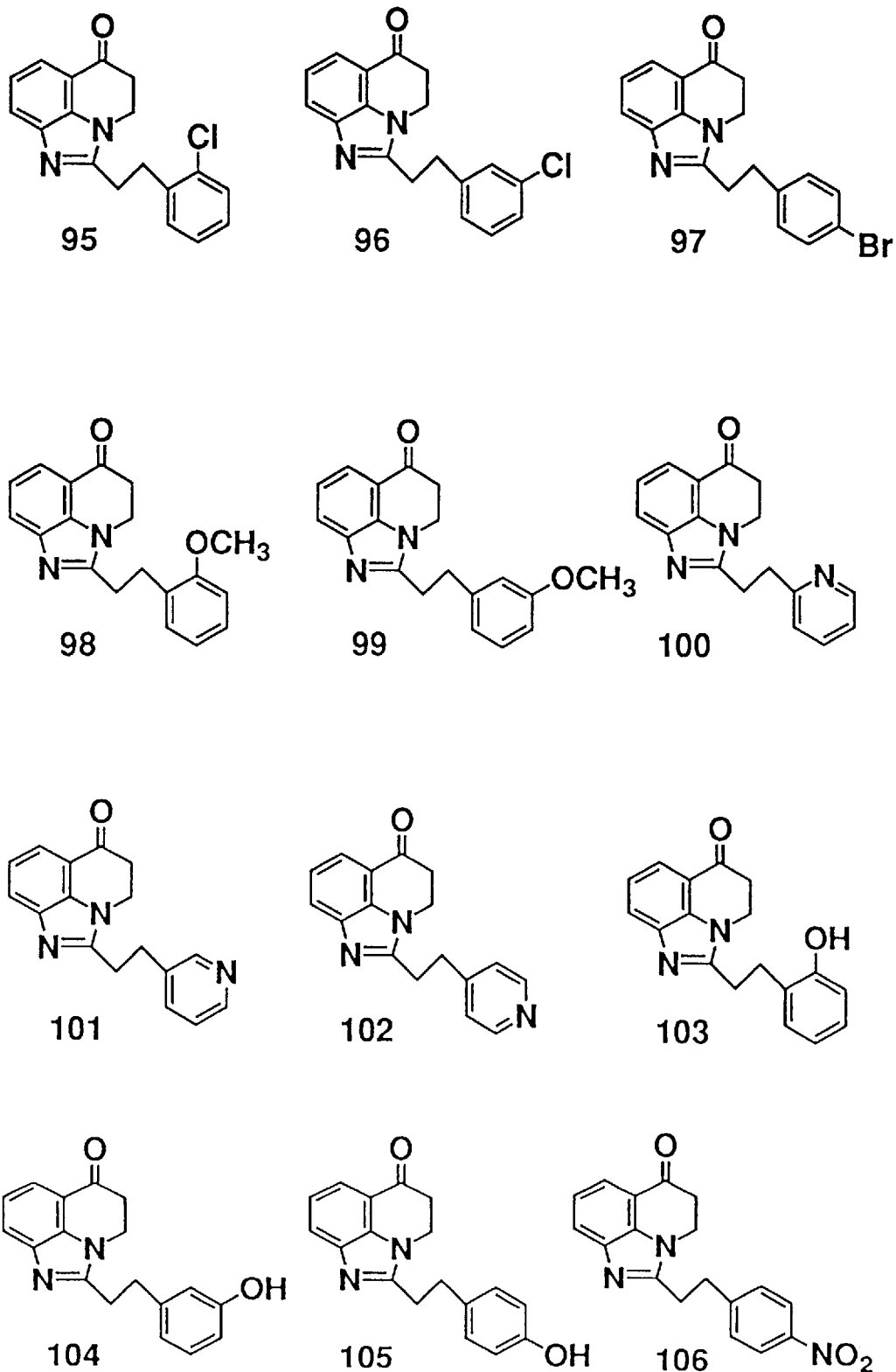
FIG. 9 is a drawing that gives chemical formulae describing the structures of the imidazoquinoline derivatives prepared in Examples 95–106.
Figure 10:
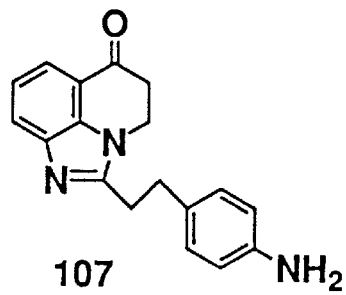
FIG. 10 is a drawing that gives chemical formulae describing the structures of the imidazoquinoline derivatives prepared in Examples 107–117.
Figure 10:
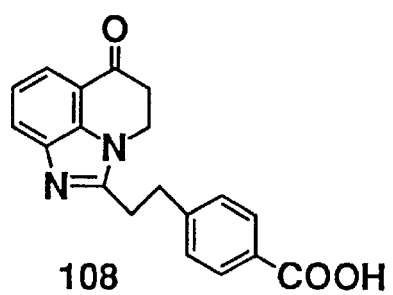
Figure 10:
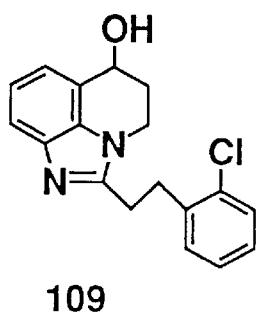
Figure 10:
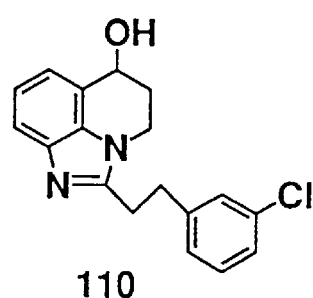
Figure 10:
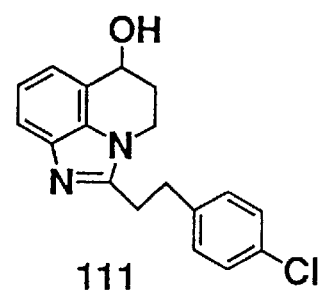
Figure 10:
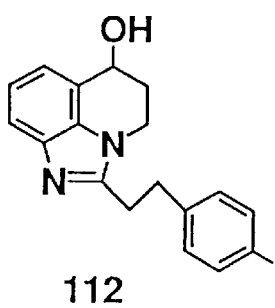
Figure 10:
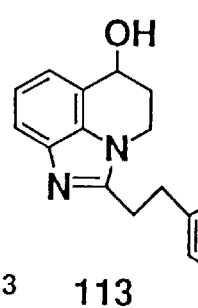
Figure 10:
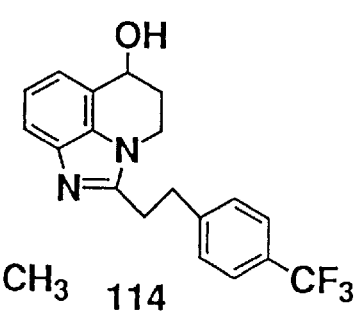
Figure 10:
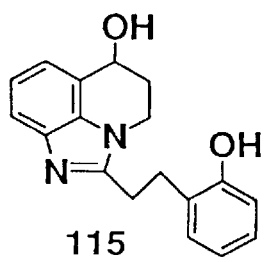
Figure 10:
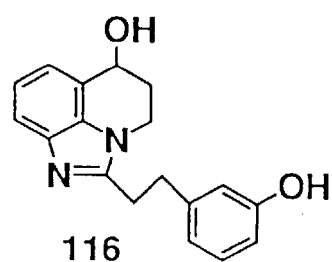
Figure 10:
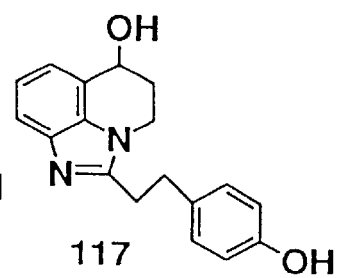
Figure 11:
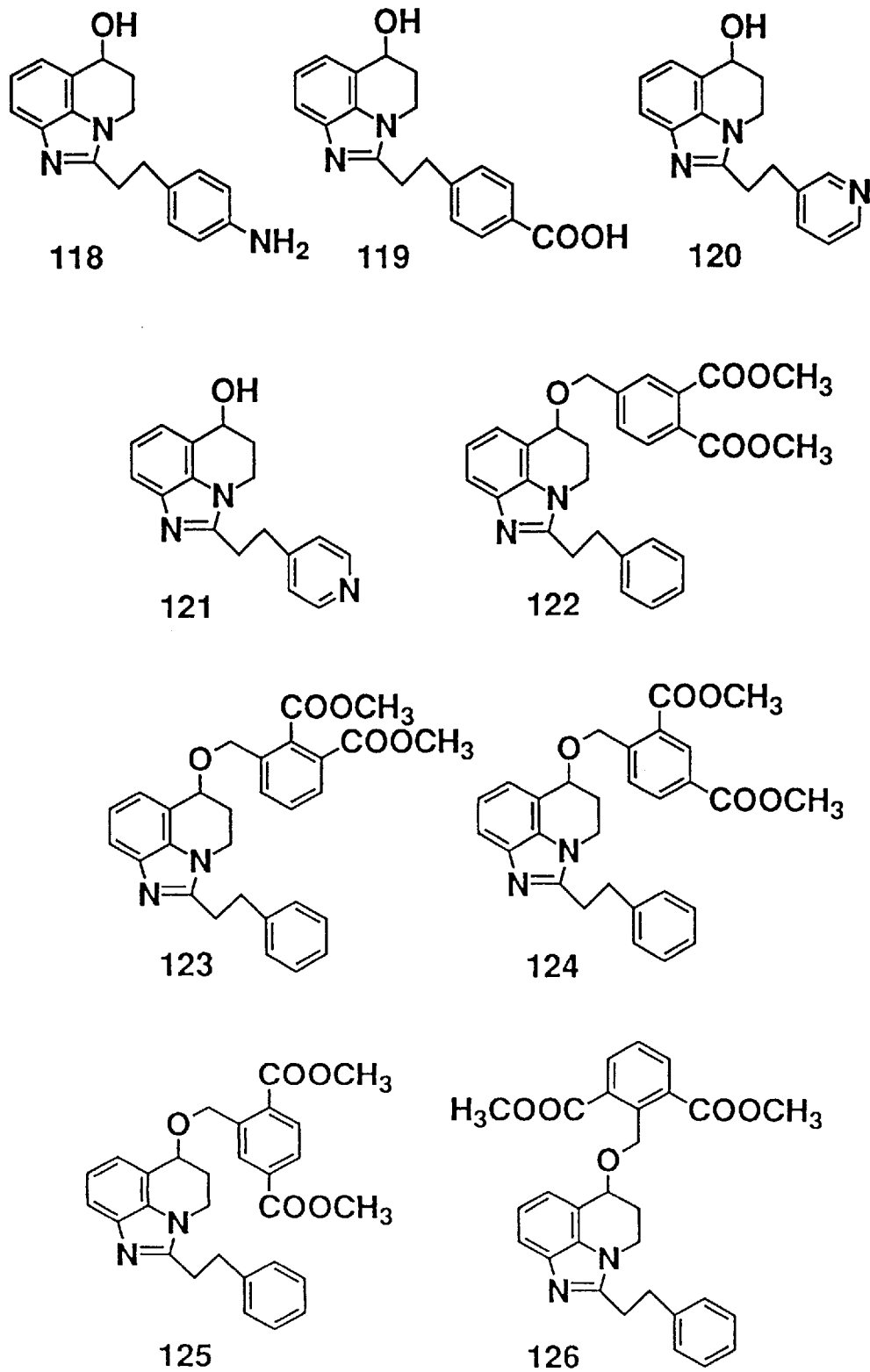
FIG. 11 is a drawing that gives chemical formulae describing the structures of the imidazoquinoline derivatives prepared in Examples 118–126.
Figure 12:
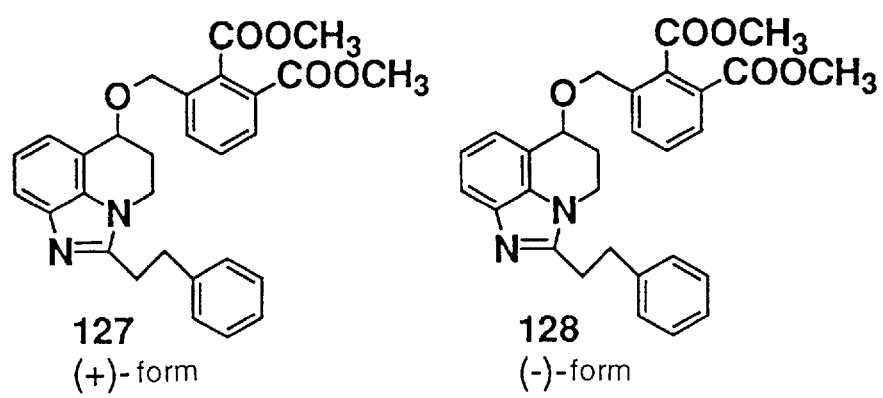
FIG. 12 is a drawing that gives chemical formulae describing the structures of the imidazoquinoline derivatives prepared in Examples 127 and 128.

The structural formulae of the compounds synthesized in the Examples are shown in FIGS. 1–12. The number affixed to the structual formula is the number of the Example wherein the compound of the structural formula is synthesized, and the number of the Example is used as the number of the compound.

TABLE 4

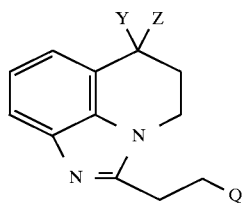

| Ex. No. | Y, Z | Q | IR cm$^{-1}$ | NMR ppm | m.p. (C.°) |
|---|---|---|---|---|---|
| 30 | N—O—C(=O)CH$_3$ | phenyl | 3431, 1763, 1498, 1196, 922, 752 | *CDCl$_3$: 7.8 d (2H), 7.3–7.1 m (6H), 3.8 t (2H), 3.3–3.2 m (4H), 3.1 t (2H), 2.3 s (3H) | 126.1–127.0 |
| 31 | H, O—C(=O)—phenyl | phenyl | 3059, 1720, 1502, 1450, 1265, 1111, 714 | *CDCl$_3$: 8.0–7.9 m (2H), 7.7 d (1H), 7.6–7.5 m (1H), 7.4–7.1 m (9H), 6.4 t (1H), 4.0–3.9 m (1H), 3.8–3.7 m (1H), 3.3–3.2 m (4H), 2.5–2.4 m (1H), 2.3–2.2 m (1H) | 98.0–99.3 |
| 32 | H, O-(2-oxopyrrolidinyl) | phenyl | 2968, 1676, 1502, 1406, 1271, 752 | *CDCl$_3$: 7.6 d (1H), 7.3–7.1 m (6H), 6.9 d (1H), 5.6 dd (1H), 3.8–3.7 m (2H), 3.2–3.0 m (6H), 2.6–2.4 m (2H), 2.2–2.0 m (4H) | 153.3–154.3 |
| 33 | H, HN—SO$_2$—phenyl | phenyl | 3435, 3061, 1493, 1452, 1335, 1155, 1092, 758, 692 | *DMSO-d$_6$: 8.5 d (1H), 8.0–7.9 m (2H), 7.7–7.6 m (4H), 7.4 t (1H), 7.4–7.2 m (5H), 7.1 d (1H), 4.9–4.8 m (1H), 4.4–4.2 m (2H), 3.4 t (2H), 3.1 t (2H), 2.1–1.9 m (2H) | 173.4–224.8 |
| 34 | H, OC$_2$H$_5$ | phenyl | neat: 2974, 1504, 1452, 1410, 1092, 752 | *CDCl$_3$: 7.7 dd (1H), 7.3–7.1 m (7H), 4.6 t (1H), 3.9–3.8 m (2H), 3.6 q (2H), 3.3–3.1 m (4H), 2.4–2.3 m (1H), 2.0–1.9 m (1H), 1.2 t (3H) | oil |
| 35 | NOCH$_3$ | phenyl | 1502, 1402, 1049, 874, 756 | *CDCl$_3$: 7.7 dd (1H), 7.6 dd (1H), 7.3–7.1 m (6H), 4.0 s (3H), 3.8 t (2H), 3.2 s (4H), 3.0 t (2H) | 109.2–113.5 |

TABLE 4-continued

| Ex. No. | Y, Z | Q | IR cm⁻¹ | NMR ppm | m.p. (C.°) |
|---|---|---|---|---|---|
| 36 | H, H₃COOC- (3-CH₂OCH₃-phenyl) | phenyl | neat: 3419, 2953, 1726, 1504, 1450, 1288, 1205, 752 | *DMSO-d₆: 8.0–7.9 m (2H), 7.6 d (1H), 7.53–7.47 m (2H), 7.3–7.1 m (7H), 4.82 t (1H), 4.77 d (1H), 4.65 d (1H), 4.2–4.1 m (1H), 4.0–3.9 m (1H), 3.8 s (3H), 3.2–3.1 m (4H), 2.4–2.3 m (1H), 2.1–2.0 m (1H) | oil |
| 37 | 4-COOCH₃-phenyl-CH₂-O- | phenyl | 3024, 2951, 1718, 1506, 1450, 1281, 1105, 1080, 754 | *CDCl₃: 8.0 d (2H), 7.7 dd (1H), 7.4 d (2H), 7.3–7.1 m (7H), 4.74 t (1H), 4.67 d (1H), 4.64 d (1H), 4.0–3.9 m (2H), 3.9 s (3H), 3.3–3.1 m (4H), 2.5–2.4 m (1H), 2.1–1.9 m (1H) | 83.2–85.4 |
| 38 | H, HOOC- (3-CH₂O-phenyl) | phenyl | 3427, 2933, 2870, 1701, 1450, 1269, 1205, 1072, 754 | *DMSO-d₆: 7.92 s (1H), 7.85 d (1H), 7.6–7.4 m (3H), 7.3–7.1 m (7H), 4.8 t (1H), 4.7 d (1H), 4.6 d (1H), 4.2–4.1 m (1H), 4.0–3.9 m (1H), 3.2–3.1 m (4H), 2.4–2.3 m (1H), 2.1–2.0 m (1H) | 187.4–194.4 |
| 39 | 4-COOH-phenyl-CH₂-O- | phenyl | 3427, 2927, 1697, 1603, 1549, 1498, 1414, 1269, 1076, 754 | *DMSO-d₆: 7.9 d (2H), 7.5 dd (1H), 7.4 d (2H), 7.3–7.1 m (7H), 4.8 t (1H), 4.7 d (1H), 4.6 d (1H), 4.3–4.2 m (1H), 4.0–3.9 m (1H), 3.2–3.1 m (4H), 2.4–2.3 m (1H), 2.1–2.0 m (1H) | 109.8–112.3 |
| 40 | 2-CH₃-benzoyloxy · HCl | phenyl | 2447, 1716, 1417, 1228, 1142, 1065, 746 | *DMSO-d₆: 7.8–7.2 m (12H), 6.4 t (1H), 4.6–4.5 m (1H), 4.1–4.0 m (1H), 3.6–3.5 m (2H), 3.3–3.2 m (2H), 2.6–2.3 m (2H), 2.5 s (3H) | 190.8–(dec.) |
| 41 | 2-COOH-benzoyloxy | phenyl | 2814, 1714, 1491, 1375, 1282, 1259, 1122 | *DMSO-d₆: 7.8–7.7 m (2H), 7.7–7.5 m (5H), 7.3–7.2 m (5H), 6.4 t (1H), 4.5–4.4 m (1H), 4.1–4.0 m (1H), 3.5 t (2H), 3.2 t (2H), 2.6–2.3 m (2H) | 171.2–172.8 |

TABLE 4-continued

| Ex. No. | Y, Z | Q | IR cm$^{-1}$ | NMR ppm | m.p. (C.°) |
|---|---|---|---|---|---|
| 42 | H, OH | 2-pyridyl | 3167, 2956, 2875, 1593, 1475, 1441, 1417, 1286, 1277, 1097, 756 | *DMSO-d$_6$: 8.5 d (1H), 7.7 dt (1H), 7.4–7.3 m (1H), 7.3 d (1H), 7.2 dd (1H), 7.1–7.0 m (2H), 5.4 d (1H), 5.0–4.9 m (1H), 4.2–4.1 m (2H), 3.3 s (4H), 2.1–2.0 m (2H) | 178.1–179.0 |
| 43 | =O | 4-CH$_3$-phenyl | 1682, 1605, 1506, 1479, 1311, 1227, 1095 | *CDCl$_3$: 7.9 d (1H), 7.7 d (1H), 7.3 t (1H), 7.1–7.0 m (4H), 4.0 t (2H), 3.2 s (4H), 2.9 t (2H), 2.3 s (3H) | 126.9–127.8 |
| 44 | =O | 4-OCH$_3$-phenyl | 1687, 1605, 1514, 1246, 1028, 845 | *CDCl$_3$: 7.9 dd (1H), 7.7 dd (1H), 7.3 t (1H), 7.1 d (2H), 6.8 d (2H), 4.1 t (2H), 3.8 s (3H), 3.2 s (4H), 2.9 t (2H) | 117.9–123.2 |
| 45 | =O | 4-Cl-phenyl | 3034, 1682, 1605, 1506, 1493, 1481, 1281, 1093, 829 | *CDCl$_3$: 7.9 d (1H), 7.7 d (1H), 7.33 t (1H), 7.25 d (2H), 7.1 d (2H), 4.2 t (2H), 3.3–3.1 m (4H), 3.0 t (2H) | 116.1–129.2 |
| 46 | =O | 4-CF$_3$-phenyl | 1682, 1603, 1504, 1481, 1333, 1117, 827 | *CDCl$_3$: 7.9 d (1H), 7.7 d (1H), 7.6 d (2H), 7.4–7.3 m (3H), 4.2 t (2H), 3.4–3.2 m (4H), 3.0 t (2H) | 125.5–126.1 |
| 47 | =O | 2-furyl | 1689, 1603, 1504, 1481, 1317, 1255, 1099, 800, 743 | *CDCl$_3$: 7.9 d (1H), 7.7 d (1H), 7.3–7.2 m (2H), 6.3–6.2 m (1H), 6.0–5.9 m (1H), 4.2 t (2H), 3.3 s (4H), 3.0 t (2H) | 103.8–105.1 |
| 48 | H, OH | 2-furyl | 3132, 2964, 1504, 1446, 1421, 1095, 800, 754 | *CDCl$_3$: 7.7 dd (1H), 7.3 d (1H), 7.3–7.2 m (2H), 6.3 dd (1H), 6.0 d (1H), 5.2–5.1 m (1H), 4.1–4.0 m (2H), 3.2 s (4H), 2.4–2.3 m (1H), 2.2–2.1 m (1H), 1.9 d (1H) | 123.9–125.2 |
| 49 | H, OCH$_2$-(2-CH$_3$-phenyl) | phenyl | neat: 2927, 1605, 1500, 1450, 1410, 1335, 1068, 750, 702 | *CDCl$_3$: 7.7 dd (1H), 7.3–7.1 m (11H), 4.7 t (1H), 4.62 d (1H), 4.58 d (1H), 4.0–3.8 m (2H), 3.3–3.1 (4H), 2.5–2.4 m (1H), 2.2 s (3H), 2.1–1.9 m (1H) | oil |
| 50 | H, OCH$_2$-(2-NO$_2$-phenyl) | phenyl | 2891, 1518, 1444, 1408, 1335, 1093, 1068, 752, 725 | *CDCl$_3$: 8.0 dd (1H), 7.7–7.6 m (2H), 7.6 t (1H), 7.4 t (1H), 7.2–7.1 m (7H), 5.1 d (1H), 4.9 d (1H), 4.8 t (1H), 3.9–3.8 m (2H), 3.3–3.1 m (4H), 2.5–2.4 m (1H), 2.1–2.0 m (1H) | 106.6–110.8 |
| 51 | H, OCH$_2$-phenyl | phenyl | neat: 3030, 2929, 1605, 1502, 1475, 1452, 1412, 1092, 1068, 752, 700 | CDCl$_3$: 7.7 dd (1H), 7.6–7.1 m (12H), 4.7 t (1H), 4.6 s (2H), 4.0–3.8 m (2H), 3.2 s (4H), 2.5–1.9 m (2H) | oil |

TABLE 4-continued

[Structure: tetrahydroquinoline with Y,Z at 4-position and N=C-CH2-CH2-Q at the 8-N imine]

| Ex. No. | Y, Z | Q | IR cm⁻¹ | NMR ppm | m.p. (C.°) |
|---|---|---|---|---|---|
| 52 | H, OCH₂-(2-OCH₃-phenyl) · HCl | phenyl | 2387, 1493, 1454, 1240, 1082, 750, 706 | *DMSO-d₆: 7.8–7.7 m (1H), 7.5 d (2H), 7.3–7.2 m (7H), 7.0 d (1H), 6.9 t (1H), 4.9 d (1H), 4.7 d (1H), 4.6 d (1H), 4.4–4.3 m (1H), 4.1–4.0 m (1H), 3.8 s (3H), 3.5 t (2H), 3.2 t (2H), 2.5–2.4 m (1H), 2.2–2.1 m (1H) | 121.0–125.1 |
| 53 | H, OCH₂-(2-NH₂-phenyl) · HCl | phenyl | 3338, 2860, 1622, 1495, 1456, 1093, 1057, 754, 702 | *DMSO-d₆: 7.7 dd (1H), 7.5–7.4 m (2H), 7.3–7.2 m (5H), 7.1–7.0 m (2H), 6.7 d (1H), 6.6 t (1H), 4.8 t (1H), 4.6 d (1H), 4.5 d (1H), 4.4–4.3 m (1H), 4.1–4.0 m (1H), 3.4 t (2H), 3.2 t (2H), 2.5–2.3 m (1H), 2.2–2.1 m (1H) | 86.5–90.7 |
| 54 | H, OCH₂-(2-OH-phenyl) | phenyl | 3450, 3062, 2931, 1599, 1454, 1271, 1070, 754 | *DMSO-d₆: 9.5 s (1H), 7.5 dd (1H), 7.3–7.1 m (9H), 6.8–6.7 m (2H), 4.8 t (1H), 4.7 d (1H), 4.5 d (1H), 4.2–4.1 m (1H), 4.0–3.9 m (1H), 3.2–3.1 m (4H), 2.4–2.3 m (1H), 2.1–2.0 m (1H) | 61.5–64.7 |
| 55 | H, OCH₂-(2-CF₃-phenyl) | phenyl | 2870, 1504, 1452, 1408, 1311, 1159, 1111, 1088, 770, 752 | *CDCl₃: 7.7 d (1H), 7.6 t (2H), 7.5 t (1H), 7.4 t (1H), 7.3–7.1 m (7H), 4.8 d (1H), 4.8–4.7 m (2H), 3.9–3.8 m (2H), 3.2–3.1 m (4H), 2.5–2.4 m (1H), 2.1–2.0 m (1H) | 77.9–79.2 |
| 56 | H, OCH₂-(2-Cl-phenyl) | phenyl | 2931, 1475, 1446, 1416, 1088, 754, 704 | *CDCl₃: 7.7–7.6 m (1H), 7.4–7.1 m (11H), 4.79 t (1H), 4.75 d (1H), 4.67 d (1H), 4.0–3.8 m (2H), 3.2–3.1 m (4H), 2.5–2.4 m (1H), 2.1–2.0 m (1H) | 54.1–57.5 |
| 57 | H, OCH₂-(2-CONH₂-phenyl) | phenyl | 3356, 3151, 1664, 1622, 1500, 1448, 1410, 1390, 1099, 750 | *DMSO-d₆: 7.8 brs (1H), 7.5–7.1 m (13H), 4.9 d (1H), 4.8 t (1H), 4.7 d (1H), 4.2–4.1 m (1H), 4.0–3.9 m (1H), 3.2–3.1 m (4H), 2.4–2.3 m (1H), 2.1–2.0 m (1H) | 169.6–172.8 |
| 58 | H, OCH₂-(2-CN-phenyl) · HCl | phenyl | 2476, 2226, 1495, 1454, 1092, 818, 764 | *DMSO-d₆: 7.9 d (1H), 7.8–7.5 m (6H), 7.4–7.2 m (5H), 5.0 brs (1H), 4.9 d (1H), 4.7 d (1H), 4.5–4.4 m (1H), 4.1–4.0 m (1H), 3.5 t (2H), 3.2 t (2H), 2.5–2.4 m (1H), 2.3–2.2 m (1H) | 166.6–173.7 |
| 59 | H, OCH₂-(2-CH₂OH-phenyl) · HCl | phenyl | 3288, 2561, 2513, 1493, 1454, 1080, 762 | *DMSO-d₆: 7.7–7.2 m (12H), 5.1 brs (1H), 4.9 brs (1H), 4.8 d (1H), 4.6 d (1H), 4.5 s (2H), 4.4–4.2 m (1H), 4.0–3.9 m (1H), 3.2 t (2H), 3.1 t (2H), 2.5–2.3 m (1H), 2.2–2.0 m (1H) | 149.4–155.3 |

TABLE 4-continued

| Ex. No. | Y, Z | Q | IR cm⁻¹ | NMR ppm | m.p. (C.°) |
|---|---|---|---|---|---|
| 60 | biphenyl-2-CH₂OH, H (HCl) | phenyl | 3431, 2366, 1784, 1626, 1497, 1454, 1439, 1144, 1092, 1076, 743, 704 | *CDCl₃: 16.9 brs (1H), 7.9 d (1H), 7.4–7.0 m (16H), 4.5–4.4 m (3H), 3.7–3.3 m (6H), 2.2–2.1 m (1H), 1.8–1.7 m (1H) | 167.5–179.6 |
| 61 | 1,2-(HOOC)₂-4-CH₂OH-phenyl, H | phenyl | 3433, 1695, 1585, 1564, 1495, 1454, 1365, 1092, 770, 756, 644 | *DMSO-d₆: 7.8–7.1 m (11H), 4.84 brs (1H), 4.78 d (1H), 4.7 d (1H), 4.3–4.2 m (1H), 4.0–3.9 m (1H), 3.3–3.1 m (4H), 2.5–2.3 m (1H), 2.1–2.0 m (1H) | 180.1–191.2 |
| 62 | 1,4-(HOOC)₂-2-CH₂OH-phenyl | phenyl | 3431, 2929, 1703, 1495, 1242, 1093, 1066, 754 | *DMSO-d₆: 8.2 s (1H), 7.9 s (2H), 7.5 d (1H), 7.3–7.1 m (7H), 5.1 d (1H), 4.94 d (1H), 4.87 brs (1H), 4.3–4.2 m (1H), 4.0–3.9 m (1H), 3.2–3.0 m (4H), 2.5–2.3 m (1H), 2.2–2.0 m (1H) | 154.9–157.6 |
| 63 | 1,3-(HOOC)₂-2-CH₂OH-phenyl | phenyl | 3433, 1703, 1630, 1495, 1454, 1269, 1107, 756 | *DMSO-d₆: 7.7 d (2H), 7.5–7.4 m (2H), 7.3–7.1 m (7H), 5.1 d (1H), 5.0 d (1H), 4.7 brs (1H), 4.2–4.1 m (1H), 4.0–3.8 m (1H), 3.3–3.1 m (4H), 2.3–2.2 m (1H), 2.1–1.9 m (1H) | 245.0–245.7 |
| 64 | 1,2-(HOOC)₂-3-CH₂OH-phenyl, H | phenyl | 3431, 1703, 1522, 1497, 1460, 1097, 748 | *DMSO-d₆: 7.8 d (1H), 7.7 d (1H), 7.5 t (2H), 7.3–7.1 m (7H), 4.8–4.7 m (2H), 4.6 d (1H), 4.2–4.1 m (1H), 4.0–3.9 m (1H), 3.2–3.1 m (4H), 2.4–2.3 m (1H), 2.1–2.0 m (1H) | 179.9–185.7 |
| 65 | 1,3-(HOOC)₂-4-CH₂OH-phenyl, H | phenyl | 3421, 2927, 1707, 1701, 1497, 1375, 1246, 1095, 1068, 756 | *DMSO-d₆: 13.3 brs (2H), 8.4 d (1H), 8.1 dd (1H), 7.7 d (1H), 7.6 dd (1H), 7.3–7.2 m (7H), 5.1 d (1H), 5.0 d (1H), 4.9 t (1H), 4.3–4.2 m (1H), 4.1–3.9 m (1H), 3.3 t (2H), 3.1 t (2H), 2.5–2.4 m (1H), 2.2–2.1 m (1H) | 147.2–149.8 |

TABLE 4-continued

| Ex. No. | Y, Z | Q | IR cm⁻¹ | NMR ppm | m.p. (C.°) |
|---|---|---|---|---|---|
| 66 | H, HOOC; HCl; (2-chloro-6-(methylthiomethyl)phenyl) | phenyl | 3421, 1701, 1495, 1452, 1292, 1248, 1076, 752, 702 | *DMSO-d₆: 7.9 d (1H), 7.6–7.4 m (3H), 7.3–7.2 m (7H), 7.1 d (1H), 4.3–4.1 m (4H), 4.0–3.9 m (1H), 3.2 t (2H), 3.1 t (2H), 2.3–2.2 m (2H) | 93.9–100.3 |
| 67 | H, HOOC; HCl; (2-chloro-6-(aminomethyl)phenyl) | phenyl | 3041, 1684, 1495, 1471, 1456, 1410, 1304, 737 | *DMSO-d₆: 7.8 d (1H), 7.7 d (1H), 7.7–7.5 m (4H), 7.4–7.2 m (5H), 7.1 d (1H), 5.9–5.8 m (1H), 4.6–4.3 m (3H), 4.2 d (1H), 3.6–3.5 m (2H), 3.2–3.1 m (2H), 2.5–2.4 m (2H) | 230.0–(dec.) |
| 68 | H, HN-CH₂CH₂-NH₂; 2HCl | phenyl | 2943, 2856, 1518, 1497, 1454, 760 | *DMSO-d₆: 10.7 brs (1H), 10.5 brs (1H), 8.4 brs (3H), 7.83 d (1H), 7.78 d (1H), 7.6 t (1H), 7.4–7.2 m (5H), 4.9 brs (1H), 4.8–4.5 m (2H), 3.6–3.0 m (8H), 2.9–2.8 m (1H), 2.5–2.4 m (1H) | 280.3–(dec.) |
| 69 | H, CH₂OH | phenyl | 3215, 2914, 1497, 1452, 1417, 1340, 1057, 750 | *DMSO-d₆: 7.4–7.2 m (6H), 7.1–7.0 m (2H), 4.9 t (1H), 4.1–3.9 m (2H), 3.8–3.7 m (1H), 3.5–3.4 m (1H), 3.2–3.0 m (5H), 2.1–2.0 m (2H) | 125.4–127.0 |
| 70 | H, CH₂COOH | phenyl | 3423, 2933, 1716, 1427, 1294, 1215, 1200, 750 | *CD₃OD: 7.5 d (1H), 7.3–7.1 m (7H), 3.9–3.7 m (2H), 3.6–3.4 m (1H), 3.3–3.1 m (4H), 2.8 dd (1H), 2.5 dd (1H), 2.2–2.1 m (1H), 2.0–1.9 m (1H) | 218.3–219.6 |
| 71 | =N–O–CH₂–C₆H₅ | phenyl | 3028, 2924, 1506, 1454, 1400, 1360, 1320, 1005, 754 | *CDCl₃: 7.7 d (1H), 7.6 d (1H), 7.4–7.1 m (11H), 5.3 s (2H), 3.8 t (2H), 3.2–3.1 m (4H), 3.1 t (2H) | 101.1–102.8 |
| 72 | =N–OC₂H₅ | phenyl | 3026, 2935, 1606, 1506, 1400, 1051, 958, 756 | *CDCl₃: 7.7 dd (1H), 7.6 dd (1H), 7.3–7.1 m (6H), 4.3 q (2H), 3.8 t (2H), 3.3–3.1 m (4H), 3.0 t (2H), 1.3 t (3H) | 125.4–128.1 |
| 73 | =N–O–C(CH₃)₃ | phenyl | 2972, 1504, 1477, 1429, 1362, 1192, 989, 960, 935, 743 | *CDCl₃: 7.7 dd (1H), 7.6 dd (1H), 7.3–7.1 m (6H), 3.8 t (2H), 3.2–3.1 m (4H), 3.0 t (2H), 1.4 s (9H) | 160.4–165.3 |
| 74 | =N–O–CH₂–CH=CH₂ | phenyl | 3026, 2924, 1502, 1402, 1348, 1032, 993, 754 | *CDCl₃: 7.7 d (1H), 7.6 d (1H), 7.3–7.1 m (6H), 6.2–6.0 m (1H), 5.4–5.2 m (2H), 4.7 dt (2H), 3.8 t (2H), 3.3–3.1 m (4H), 3.1 t (2H) | 67.8–70.6 |

TABLE 4-continued

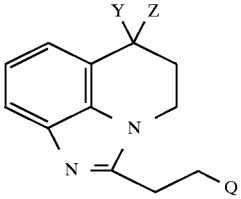

| Ex. No. | Y, Z | Q | IR cm$^{-1}$ | NMR ppm | m.p. (C.°) |
|---|---|---|---|---|---|
| 75 | HOOC-C6H4-CH2-O-N= | phenyl | 3392, 1686, 1417, 1248, 1049, 1018, 744 | *DMSO-d$_6$: 13.0 brs (1H), 7.9 d (1H), 7.6–7.1 m (11H), 5.6 s (2H), 4.2 t (2H), 3.4–3.1 m (6H) | 200.0–210.0 |
| 76 | C6H5-C(O)-O-N= | phenyl | 3469, 1741, 1252, 1059, 702 | *CDCl$_3$: 8.1 d (2H), 7.9 d (1H), 7.8 d (1H), 7.6 t (1H), 7.5 t (2H), 7.4–7.1 m (6H), 3.9 t (2H), 3.3 t (2H), 3.3–3.1 m (4H) | 152.1–154.5 |
| 77 | 4-CH3-C6H4-SO2-O-N= | phenyl | 1597, 1502, 1365, 1192, 1178, 850 | *CDCl$_3$: 8.0 d (2H), 7.8 d (1H), 7.5 d (1H), 7.4 d (2H), 7.3–7.1 m (6H), 3.7 t (2H), 3.2–3.1 m (4H), 3.1 t (2H), 2.5 s (3H) | 127.2–132.0 |
| 78 | H, HN-C(O)-CH3 | phenyl | 3180, 3024, 1668, 1547, 1504, 1414, 1279, 758 | *CDCl$_3$: 7.6 d (1H), 7.3–7.1 m (7H), 6.1 d (1H), 5.3 q (1H), 3.8–3.6 m (2H), 3.2–3.0 m (4H), 2.2 q (2H), 2.1 s (3H) | 213.6–214.6 |
| 79 | HOOC-CH2-C(O)-NH, H | phenyl | 3396, 1641, 1500, 1417, 1161 | *DMSO-d$_6$: 7.4 d (1H), 7.3–7.2 m (5H), 7.1 t (1H), 7.0 d (1H), 5.3–5.2 m (1H), 4.1 t (2H), 3.2–3.1 m (4H), 2.9 brs (2H), 2.3–2.2 m (1H), 2.0–1.9 m (1H) | 262.9–(dec.) |
| 80 | H, H5C2OOC-CH2-C(O)-NH | phenyl | 3188, 2962, 1740, 1678, 1547, 1416, 1165, 758 | *CDCl$_3$: 7.6 d (1H), 7.5 d (1H), 7.3–7.1 m (7H), 5.4–5.3 m (1H), 4.2 q (2H), 3.7 t (2H), 3.42 d (1H), 3.40 d (1H), 3.2–3.1 m (4H), 2.3–2.0 m (2H), 1.3 t (3H) | 134.2–142.8 |
| 81 | H, H5C2OOC-C(O)-NH | phenyl | 3448, 3153, 2985, 1734, 1676, 1547, 1203, 754 | *DMSO-d$_6$: 9.3 d (1H), 7.4 d (1H), 7.3–7.2 m (5H), 7.1 t (1H), 6.9 d (1H), 5.4–5.3 m (1H), 4.4–4.0 m (4H), 3.2–3.1 m (4H), 2.2–2.1 m (2H), 1.3 t (3H) | 170.9–174.6 |
| 82 | H, C6H5-C(O)-NH | phenyl | 3437, 3246, 3026, 1651, 1637, 1527, 1491, 1412, 752, 700 | *CDCl$_3$: 7.9–7.8 m (2H), 7.6 d (1H), 7.6–7.4 m (3H), 7.3–7.1 m (7H), 6.7 d (1H), 5.5 q (1H), 3.8–3.6 m (2H), 3.2–3.0 m (4H), 2.3–2.2 m (2H) | 212.9–214.9 |

TABLE 4-continued
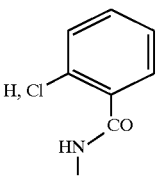
| Ex. No. | Y, Z | Q | IR cm$^{-1}$ | NMR ppm | m.p. (C.°) |
|---|---|---|---|---|---|
| 83 | 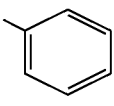 H, Cl | 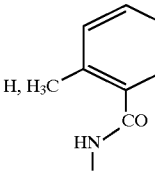 | 3151, 3028, 2935, 1659, 1533, 1500, 1414, 752 | *DMSO-d$_6$: 8.9 d (1H), 7.5–7.1 m (12H), 5.5–5.4 m (1H), 4.3–4.1 m (2H), 3.2–3.0 m (4H), 2.3–2.1 m (2H) | 222.5–(dec.) |
| 84 | 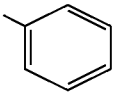 H, H$_3$C | 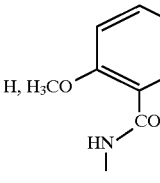 | 3201, 3026, 2927, 1651, 1524, 1502, 1414, 750, 700 | *DMSO-d$_6$: 8.7 d (1H), 7.5–7.1 m (12H), 5.5–5.4 m (1H), 4.3–4.1 m (2H), 3.2–3.1 m (4H), 2.4 s (3H), 2.4–2.1 m (2H) | 194.3–(dec.) |
| 85 | 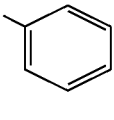 H, H$_3$CO | 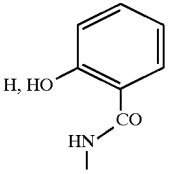 | 3377, 2914, 1649, 1518, 1479, 1408, 1232, 1018, 750 | *CDCl$_3$: 8.3 dd (1H), 8.2 d (1H), 7.7 d (1H), 7.5–7.4 m (1H), 7.3–7.1 m (8H), 7.0 d (1H), 5.6–5.5 m (1H), 3.9 s (3H), 3.9–3.8 m (2H), 3.3–3.1 m (4H), 2.6–2.5 m (1H), 2.2–2.0 m (1H) | 169.3–169.9 |
| 86 | 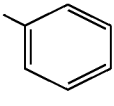 H, HO | 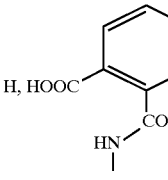 | 3228, 2933, 2767, 1635, 1595, 1541, 1493, 1346, 758 | *DMSO-d$_6$: 12.3 brs (1H), 9.2 d (1H), 7.9 d (1H), 7.7 d (1H), 7.6 t (1H), 7.5–7.3 m (7H), 7.1–6.9 m (2H), 5.7–5.6 m (1H), 4.5–4.3 m (2H), 3.6–3.5 m (2H), 3.2–3.1 m (2H), 2.5–2.3 m (2H) | 221.9–226.6 |
| 87 | 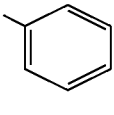 H, HOOC | 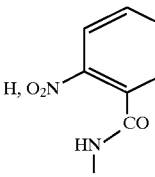 | 3419, 3259, 3028, 1713, 1651, 1541, 1269, 752 | *CDCl$_3$: 8.8 d (1H), 7.9–7.7 m (2H), 7.5–7.4 m (3H), 7.3–7.1 m (4H), 7.0 t (1H), 6.9–6.8 m (2H), 5.4–5.3 m (1H), 4.0–3.9 m (1H), 3.5–3.4 m (1H), 2.9–2.8 m (4H), 2.4–2.3 m (1H), 2.0–1.9 m (1H) | 159.4–162.2 |
| 88 | 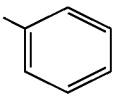 H, O$_2$N | | 1651, 1531, 1414, 1350, 748, 700 | *DMSO-d$_6$: 9.1 d (1H), 8.1 d (1H), 7.8–7.6 m (3H), 7.5–7.1 m (8H), 5.5–5.4 m (1H), 4.2–4.1 m (2H), 3.2–3.0 m (4H), 2.4–2.0 m (2H) | 221.1–224.5 |

TABLE 4-continued

| Ex. No. | Y, Z | Q | IR cm⁻¹ | NMR ppm | m.p. (C.°) |
|---|---|---|---|---|---|
| 89 | H, H₂N-C₆H₄-C(O)NH- (2-aminobenzamido) | phenyl | 3470, 3352, 3024, 1635, 1583, 1522, 1259, 752, 700 | *DMSO-d₆: 8.6 d (1H), 7.6 d (1H), 7.5 d (1H), 7.3–7.1 m (7H), 7.0 d (1H), 6.7 d (1H), 6.5 t (1H), 5.5–5.4 m (1H), 4.3–4.0 m (2H), 3.2–3.1 m (4H), 2.3–2.1 m (2H) | 190.1–198.4 |
| 90 | H, nicotinamido (3-pyridyl-C(O)NH-) | phenyl | 3223, 1655, 1502, 1413, 1281, 754, 708 | *DMSO-d₆: 9.1–9.0 m (2H), 8.7 dd (1H), 8.3–8.2 m (1H), 7.5–7.4 m (2H), 7.3–7.0 m (7H), 5.6–5.5 m (1H), 4.3–4.1 m (2H), 3.2–3.1 m (4H), 2.3–2.1 m (2H) | 174.4–175.9 |
| 91 | H, isonicotinamido (4-pyridyl-C(O)NH-) | phenyl | 3211, 1660, 1533, 1500, 1414, 1331, 754, 702 | *DMSO-d₆: 9.2 d (1H), 8.7 dd (2H), 7.8 dd (2H), 7.5 d (1H), 7.3–7.2 m (5H), 7.1 t (1H), 7.0 d (1H), 5.6–5.5 m (1H), 4.3–4.1 m (2H), 3.2–3.1 m (4H), 2.3–2.1 m (2H) | 188.4–190.4 |
| 92 | H, cyclohexyl-C(O)NH- | phenyl | 3257, 2929, 2852, 1641, 1552, 1498, 1448, 748, 698 | *CDCl₃: 7.6 d (1H), 7.3–7.0 m (7H), 5.7 d (1H), 5.4–5.3 m (1H), 3.8–3.6 m (2H), 3.2–3.1 m (4H), 2.3–2.0 m (3H), 2.0–1.2 m (10H) | 193.9–(dec.) |
| 93 | H, PhCH₂C(O)NH- | phenyl | 3028, 1662, 1535, 1497, 1412, 754, 700 | *CDCl₃: 7.6 d (1H), 7.4–7.1 m (11H), 6.9 d (1H), 5.9 d (1H), 5.4–5.3 m (1H), 3.7–3.6 m (4H), 3.2–3.0 m (4H), 2.3–2.2 m (1H), 2.0–1.9 m (1H) | 160.5–(dec.) |
| 94 | H, 2-thienyl-C(O)NH- | phenyl | 3440, 3022, 1628, 1539, 1504, 1416, 750, 698 | *DMSO-d₆: 8.9 d (1H), 7.9–7.8 m (1H), 7.8 d (1H), 7.5 d (1H), 7.3–7.1 m (7H), 7.3–7.1 m (7H), 7.0 d (1H), 5.5–5.4 m (1H), 4.2–4.1 m (2H), 3.2–3.1 m (4H), 2.3–2.1 m (2H) | 232.2–233.7 |
| 95 | =O | 2-chlorophenyl | 1687, 1603, 1502, 1479, 1282, 746 | *CDCl₃: 7.9 d (1H), 7.7 d (1H), 7.4–7.1 m (5H), 4.2 t (2H), 3.4–3.2 m (4H), 2.9 t (2H) | 111.0–112.3 |
| 96 | =O | 3-chlorophenyl | 1686, 1603, 1504, 1479, 1317, 1228, 1095 | *CDCl₃: 7.9 dd (1H), 7.7 dd (1H), 7.3 d (1H), 7.3–7.2 m (3H), 7.1–7.0 m (1H), 4.2 t (2H), 3.3–3.2 m (4H), 3.0 t (2H) | 121.1–121.3 |
| 97 | =O | 4-bromophenyl | 1684, 1604, 1506, 1491, 1283, 825 | CDCl₃: 7.9 d (1H), 7.7 d (1H), 7.4 d (2H), 7.3 t (1H), 7.1 d (2H), 4.2 t (2H), 3.2 s (4H), 3.0 t (2H) | 123.2–125.8 |

TABLE 4-continued

| Ex. No. | Y, Z | Q | IR cm$^{-1}$ | NMR ppm | m.p. (C.°) |
|---|---|---|---|---|---|
| 98 | =O | 2-OCH₃-phenyl | 1684, 1605, 1500, 1246, 758 | *CDCl₃: 7.9 d (1H), 7.7 d (1H), 7.3–7.2 m (2H), 7.0 dd (1H), 6.9–6.8 m (2H), 4.1 t (2H), 3.8 s (3H), 3.2 s (4H), 2.9 t (2H) | 151.7–152.4 |
| 99 | =O | 3-OCH₃-phenyl | 1687, 1603, 1504, 1489, 1263, 791 | *CDCl₃: 7.9 d (1H), 7.7 d (1H), 7.3 t (1H), 7.2 t (1H), 6.8–6.7 m (2H), 6.7 t (1H), 4.1 t (2H), 3.7 s (3H), 3.2 s (4H), 2.9 t (2H) | 135.2–136.3 |
| 100 | =O | 2-pyridyl | 1684, 1603, 1504, 1479, 1279, 1097, 754 | CDCl₃: 8.6 dd (1H), 7.9 d (1H), 7.7–7.5 m (2H), 7.3 d (1H), 7.2–7.0 m (2H), 4.4 t (2H), 3.4 s (4H), 3.0 t (2H) | 128.9–131.4 |
| 101 | =O | 3-pyridyl | 1684, 1603, 1502, 1479, 1423, 1315, 1095, 798, 710 | *CDCl₃: 8.5–8.4 m (2H), 7.9 d (1H), 7.7 d (1H), 7.5–7.4 m (1H), 7.3 t (1H), 7.3–7.2 m (1H), 4.2 t (2H), 3.3–3.1 m (4H), 3.0 t (2H) | 124.2–125.2 |
| 102 | =O | 4-pyridyl | 1693, 1605, 1502, 1414, 1317, 1257, 808 | *CDCl₃: 8.5 dd (2H), 7.9 d (1H), 7.7 d (1H), 7.3 t (1H), 7.2 dd (2H), 4.3 t (2H), 3.3–3.2 m (4H), 3.0 t (2H) | 129.9–132.2 |
| 103 | =O | 2-OH-phenyl | 3433, 1689, 1603, 1483, 1257, 760 | *CDCl₃: 11.2 s (1H), 7.9 d (1H), 7.7 d (1H), 7.3 t (1H), 7.2–7.1 m (2H), 7.0 d (1H), 6.9 t (1H), 4.4 t (2H), 3.4–3.3 m (4H), 3.1 t (2H) | 192.7–193.5 |
| 104 | =O | 3-OH-phenyl | 3433, 2931, 1687, 1605, 1587, 1483, 1352, 1281 | *DMSO-d₆: 9.3 s (1H), 7.9 d (1H), 7.5 d (1H), 7.3 t (1H), 7.1 t (1H), 6.7–6.6 m (3H), 4.4 t (2H), 3.2–2.9 m (6H) | 187.3–188.7 |
| 105 | =O | 4-OH-phenyl | 1693, 1603, 1510, 1481, 1240, 1099 | *DMSO-d₆: 9.2 s (1H), 7.8 dd (1H), 7.5 d (1H), 7.3 t (1H), 7.1 d (2H), 6.7 d (2H), 4.4 t (2H), 3.2–3.1 m (2H), 3.0–2.9 m (4H) | 196.5–200.5 |
| 106 | =O | 4-NO₂-phenyl | 1684, 1603, 1512, 1344, 1097 | *CDCl₃: 8.2 d (2H), 7.9 d (1H), 7.7 d (1H), 7.4 d (2H), 7.3 t (1H), 4.3 t (2H), 3.4 t (2H), 3.2 t (2H), 3.0 t (2H) | 203.9–205.2 |
| 107 | =O | 4-NH₂-phenyl | 3423, 3342, 1684, 1605, 1516, 1481, 1352, 1281, 1099, 829 | *CDCl₃: 7.9 d (1H), 7.7 d (1H), 7.3 t (1H), 6.9 d (2H), 6.6 d (2H), 4.0 t (2H), 3.2–3.0 m (4H), 2.9 t (2H) | 160.4–180.8 |
| 108 | =O | 4-COOH-phenyl | 3427, 1680, 1605, 1481, 1414, 1311, 1279 | *DMSO-d₆: 7.9–7.8 m (3H), 7.5 d (1H), 7.4 d (2H), 7.3 t (1H), 4.5 t (2H), 3.2 brs (4H), 3.0 t (2H) | 234.9–239.9 |

TABLE 4-continued

| Ex. No. | Y, Z | Q | IR cm⁻¹ | NMR ppm | m.p. (C.°) |
|---|---|---|---|---|---|
| 109 | H, OH | 2-chlorophenyl | 3199, 2968, 2933, 1502, 1475, 1446, 1414, 1288, 1105, 1034, 748 | *CDCl₃: 7.7–7.6 m (1H), 7.4 d (1H), 7.2–7.1 m (5H), 5.1 t (1H), 4.0–3.9 m (2H), 3.3–3.1 m (4H), 2.3–2.2 m (2H), 2.1–2.0 m (1H) | 171.3–172.2 |
| 110 | H, OH | 3-chlorophenyl | 3213, 2960, 2937, 1597, 1504, 1477, 1416, 1286, 1105, 760 | *CDCl₃: 7.7–7.6 m (1H), 7.3–7.0 m (6H), 5.1 t (1H), 4.0–3.9 m (2H), 3.2–3.0 m (4H), 2.5 brs (1H), 2.4–2.3 m (1H), 2.1–2.0 m (1H) | 148.0–152.4 |
| 111 | H, OH | 4-chlorophenyl | 3174, 2964, 1495, 1479, 1416, 1090, 822, 750 | *CDCl₃: 7.7–7.6 m (1H), 7.3–7.2 m (4H), 7.1 d (2H), 5.1 t (1H), 4.0–3.8 m (2H), 3.2–3.0 m (4H), 2.4 brs (1H), 2.3–2.2 m (1H), 2.1–2.0 m (1H) | 159.7–160.8 |
| 112 | H, OH | 4-methylphenyl | 3151, 2954, 1504, 1477, 1444, 1408, 1090, 752 | *CDCl₃: 7.7–7.6 m (1H), 7.3–7.2 m (2H), 7.1 d (2H), 7.0 d (2H), 5.1 t (1H), 3.9–3.8 m (2H), 3.2–3.1 m (4H), 2.3 s (3H), 2.3–2.2 m (1H), 2.2 brs (1H), 2.1–2.0 m (1H) | 147.2–149.5 |
| 113 | H, OH | 4-methoxyphenyl | 3194, 1610, 1514, 1450, 1412, 1244, 1092, 825 | *CDCl₃: 7.7 dd (1H), 7.3–7.2 m (2H), 7.1 d (2H), 6.8 d (2H), 5.1 t (1H), 3.9–3.8 m (2H), 3.8 s (3H), 3.2–3.1 m (4H), 2.3–2.2 m (1H), 2.1–2.0 m (2H) | 160.2–161.8 |
| 114 | H, OH | 4-trifluoromethylphenyl | 1614, 1500, 1416, 1325, 1159, 1109, 1065 | *CDCl₃: 7.7–7.6 m (1H), 7.5 d (2H), 7.3–7.1 m (4H), 5.1 brs (1H), 4.0–3.8 m (2H), 3.3–3.0 m (4H), 2.4 brs (1H), 2.3–2.2 m (1H), 2.1–2.0 m (1H) | 160.7–161.7 |
| 115 | H, OH | 2-hydroxyphenyl | 3433, 2929, 1595, 1504, 1456, 1417, 1267, 1244, 752 | *CDCl₃: 11.9 brs (1H), 7.7 dd (1H), 7.2–7.1 m (4H), 6.9 d (1H), 6.8 t (1H), 5.1 t (1H), 4.2–4.1 m (2H), 3.4–3.2 m (4H), 2.4–2.3 m (1H), 2.2–2.1 m (1H), 1.9 brs (1H) | 182.3–184.9 |
| 116 | H, OH | 3-hydroxyphenyl | 3390, 2926, 1583, 1477, 1423, 1281, 752 | *DMSO-d₆: 9.3 s (1H), 7.5–7.4 m (1H), 7.1–7.0 m (3H), 6.7–6.6 m (3H), 5.4 d (1H), 5.0–4.9 m (1H), 4.1–4.0 m (2H), 3.1–3.0 m (4H), 2.1–2.0 m (2H) | 187.1–190.9 |
| 117 | H, OH | 4-hydroxyphenyl | 3365, 2925, 1612, 1516, 1419, 1244, 827, 750 | *DMSO-d₆: 9.2 s (1H), 7.5–7.4 m (1H), 7.1–7.0 m (2H), 7.0 d (2H), 6.7 d (2H), 5.4 d (1H), 4.9–4.8 m (1H), 4.1–4.0 m (2H), 3.1–2.9 m (4H), 2.1–2.0 m (2H) | 104.2–(dec.) |
| 118 | H, OH | 4-aminophenyl | 3435, 3350, 1630, 1518, 1477, 1417, 1281, 804, 760 | *CDCl₃: 7.7–7.6 m (1H), 7.2–7.1 m (2H), 6.9 d (2H), 6.6 d (2H), 5.1 t (1H), 3.9–3.8 m (2H), 3.6 brs (2H), 3.1 s (4H), 2.3–2.0 m (3H) | 184.0–188.3 |
| 119 | H, OH | 4-carboxyphenyl | 3398, 1697, 1610, 1271, 1101, 752 | *DMSO-d₆: 12.8 brs (1H), 7.9 d (2H), 7.4–7.3 m (3H), 7.1–7.0 m (2H), 5.5–5.4 m (1H), 5.0–4.9 m (1H), 4.2–4.0 m (2H), 3.2 s (4H), 2.1–2.0 m (2H) | 233.5–236.7 |

TABLE 4-continued

| Ex. No. | Y, Z | Q | IR cm$^{-1}$ | NMR ppm | m.p. (C.°) |
|---|---|---|---|---|---|
| 120 | H, OH | 3-pyridyl | 3365, 1579, 1504, 1479, 1431, 1412, 1267, 1095, 758 | *CDCl$_3$: 8.5–8.3 m (2H), 7.7–7.6 m (1H), 7.5–7.4 m (1H), 7.2–7.1 m (3H), 5.1 t (1H), 4.0–3.9 m (2H), 3.3–3.1 m (4H), 2.8 brs (1H), 2.3–2.2 m (1H), 2.1–2.0 m (1H) | 53.3–54.3 |
| 121 | H, OH | 4-pyridyl | 3392, 3176, 1606, 1502, 1414, 1103, 758 | *CDCl$_3$: 8.5 d (2H), 7.7–7.6 m (1H), 7.2–7.1 m (2H), 7.1 d (2H), 5.1 t (1H), 4.1–3.9 m (2H), 3.3–3.1 m (4H), 2.6 brs (1H), 2.4–2.3 m (1H), 2.2–2.0 m (1H) | 147.0–150.0 |
| 122 | H, H$_3$COOC / H$_3$COOC- with -OCH$_2$- substituted phenyl | phenyl | neat: 2953, 1730, 1606, 1502, 1437, 1412, 1298, 1203, 1128, 1072, 754, 704 | *CDCl$_3$: 7.7–7.6 m (2H), 7.6 s (1H), 7.5 dd (1H), 7.3–7.1 m (7H), 4.7 t (1H), 4.6 s (2H), 3.9–3.8 m (2H), 3.90 s (3H), 3.90 s (3H), 3.3–3.1 m (4H), 2.5–2.4 m (1H), 2.1–1.9 m (1H) | oil |
| 123 | H, H$_3$COOC / H$_3$COOC- with -OCH$_2$- substituted phenyl | phenyl | neat: 2953, 1734, 1284, 1246, 1149, 1070, 754 | *CDCl$_3$: 7.9 dd (1H), 7.7 dd (1H), 7.6 d (1H), 7.5 t (1H), 7.3–7.1 m (7H), 4.7–4.6 m (3H), 4.0–3.8 m (2H), 3.9 s (3H), 3.7 s (3H), 3.3–3.1 m (4H), 2.4–2.3 m (1H), 2.0–1.9 m (1H) | oil |
| 124 | H, H$_3$COOC / H$_3$COOC- with -OCH$_2$- substituted phenyl | phenyl | neat: 2954, 1732, 1714, 1614, 1506, 1456, 1317, 1254, 1072, 756, 702 | *CDCl$_3$: 8.6 d (1H), 8.1 dd (1H), 7.7–7.6 m (2H), 7.3–7.1 m (7H), 5.1 d (1H), 5.0 d (1H), 4.8 t (1H), 4.0–3.8 m (2H), 3.93 s (3H), 3.87 s (3H), 3.3–3.2 m (4H), 2.5–2.4 m (1H), 2.1–2.0 m (1H) | oil |
| 125 | H, H$_3$COOC / H$_3$COOC- with -OCH$_2$- substituted phenyl | phenyl | 1718, 1302, 1255, 1111, 1070, 750 | *CDCl$_3$: 8.2 s (1H), 8.0–7.9 m (2H), 7.7–7.6 m (1H), 7.3–7.2 m (7H), 5.02 d (1H), 4.97 d (1H), 4.8 t (1H), 4.0–3.8 m (2H), 3.9 s (3H), 3.8 s (3H), 3.3–3.1 m (4H), 2.5–2.4 m (1H), 2.1–2.0 m (1H) | 97.1–99.5 |
| 126 | H, COOCH$_3$ / H$_3$COOC- with -OCH$_2$- substituted phenyl | phenyl | neat: 2951, 1724, 1676, 1433, 1304, 1259, 1205, 1153, 752 | *CDCl$_3$: 7.8 d (2H), 7.7 d (1H), 7.4 t (1H), 7.3–7.1 m (7H), 5.2 d (1H), 5.0 d (1H), 4.6 t (1H), 3.9–3.8 m (2H), 3.7 s (6H), 3.2–3.1 m (4H), 2.4–2.3 m (1H), 2.0–1.9 m (1H) | oil |

The following are exemplary pharmaceutical formulations that contain compounds of the invention but the invention is by no means limited to these examples.

Formulation 1

| Capsule | |
|---|---|
| Ingredient | Amount of Use, g |
| Compound of Example 1 | 50 |
| Lactose | 935 |
| Magnesium stearate | 15 |

The respective ingredients were weighed and thereafter mixed uniformly. The mixed powder was divided in 200-mg portions, which were charged into suitable hard capsules to prepare capsule formulations.

Formulation 2

| Tablet | |
|---|---|
| Ingredient | Amount of Use, g |
| Compound of Example 22 | 50 |
| Lactose | 755 |
| Potato starch | 165 |
| Polyvinyl alcohol | 15 |
| Magnesium stearate | 15 |

The respective ingredients were weighed and, thereafter, the titled compound, lactose and potato starch were mixed uniformly. To the resulting mixture, an aqueous solution of polyvinyl alcohol was added and granules were prepared by the wet-granulation method. The granulation was dried, mixed with magnesium stearate, compressed and punched to prepare tablets each weighing 200 mg.

Formulation 3

| Granule | |
|---|---|
| Ingredient | Amount of Use, g |
| Compound of Example 13 | 200 |
| Lactose | 450 |
| Corn starch | 300 |
| Hydroxypropyl cellulose | 50 |

The respective ingredients were weighed and uniformly mixed; the mixed powder was processed in the usual manner to prepare granules.

Formulation 4

| Injection | |
|---|---|
| Ingredient | Amount of Use |
| Compound of Example 5 | 1 g |
| Sodium chloride | 9 g |
| Sterile distilled water for injection | 1,000 mL |

The respective ingredients were weighed and uniformly mixed; the mixed powder was dissolved in sterile distilled water for injection, sterilized by filtration, divided into 10-mL ampules at 5-mL portions, which were fused and sealed for preparing injections.

Industrial Applicability

Using the compounds of the invention which have an imidazoquinoline skeleton contributes a great potency in inhibiting the increase of eosinophils. In addition, the compounds of the invention which have an imidazoquinoline skeleton are extremely low in toxicity and feature high safety, thereby exhibiting a great potency in inhibiting the increase of eosinophils not only clinically but also in animals so that they are expected to provide remarkable efficacy in preventing and/or treating diseases that manifest the increase of eosinophils.

The purpose of preventing and/or treating diseases that manifest the increase of eosinophils can also be achieved by the pharmaceutical compositions of the invention. Specifically, they have a great potency in inhibiting the increase of eosinophils and, hence, are effective in preventing and/or treating those diseases in which eosinophils are believed to participate as primary immunocytes in their pathophysiology, namely, such diseases as verminations, hypereosinophilic syndrome (HES), eosinophilic pneumonia, eosinophilic enterogastritis, bronchial asthma, etc.

We claim:

1. A compound represented by the following formula (I) or a salt thereof:

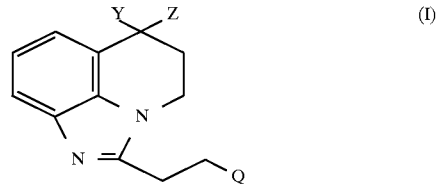

where Q represents a phenyl group that may be mono- or di-substituted with any group selected from the group consisting of a halogen atom, a nitro group, a straight or branched alkyl group having 1–4 carbon atoms that may be substituted with one or more halogen atoms, a straight or branched alkoxy group having 1–4 carbon atoms, an optionally protected hydroxyl group, an optionally protected amino group and an optionally protected carboxyl group, pyridyl group or furyl group;

Y and Z taken together represent an oxygen atom, and a methylene group that may be substituted with a carboxyl group or Y represents a hydrogen atom; and Z represents a hydrogen atom, a hydroxymethyl group, a carboxymethyl group, a 2-oxo-1-pyrrolidinyl group or the following formula (III):

where A represents an oxygen atom, a sulfur atom or the group —NH—; $R^2$ represents a hydrogen atom, an alkyl group having 1–4 carbon atoms, an aminoalkyl group having 1–4 carbon atoms, a phenylsulfonyl group, an alkanoyl group whose alkyl group has 1–6 carbon atoms that may be mono- or di-substituted with any group selected from the group consisting of a phenyl group, an alkoxycarbonyl group whose alkyl group has 1–4 carbon atoms and an optionally protected carboxyl group, a benzoyl group that may be mono- or di-substituted with any group selected from the group consisting of a halogen atom, a nitro group, an alkyl group having 1–4 carbon atoms, an alkoxy group having 1–4 carbon atoms, an optionally protected hydroxyl group, an optionally protected carboxyl group and an optionally protected amino group, a benzyl group that may be mono- or di-substituted in the phenyl moiety with any group selected from the group consisting of a halogen atom, a nitro group, a phenyl group, a cyano group, a carbamoyl group, a hydroxymethyl group, a sulfo group, a carboxymethyl group, an alkyl group having 1–4 carbon atoms that may be substituted with one or more halogen atoms, an alkoxy group having 1–4 carbon atoms, an alkoxycarbonyl group whose alkyl group has 1–4 carbon atoms, an optionally protected hydroxyl group, an optionally protected carboxyl group and an optionally protected amino group, an alkoxyoxalyl group whose alkyl group has 1 or 2 carbon atoms, a cycloalkylcarbonyl group whose cycloalkyl group has 3–6 carbon atoms, a pyridinecarbonyl group or a thiophenecarbonyl group.

2. The compound or the salt thereof recited in claim 1, wherein Q in the formula (I) represents a phenyl group, Y represents either a hydrogen atom or, when taken together with Z, an oxygen atom, Z represents a hydrogen atom or the formula (III) (A and $R^2$ each have the same meaning as defined in claim 1) or a salt of said compound.

3. The compound or the salt thereof recited in claim 1 or 2, wherein when Y and Z in the formula (I) are a hydrogen atom and the formula (III), respectively, A represents an oxygen atom and $R^2$ represents a hydrogen atom or a benzyl group that may be mono- or di-substituted in the phenyl moiety with any group selected from the group consisting of an alkoxycarbonyl group whose alkyl group has 1–4 carbon atoms and an optionally protected carboxyl group.

4. A pharmaceutical composition comprising an effective amount of the compound of claim 1 and a pharmaceutically suitable carrier.

5. A pharmaceutical composition comprising an effective amount of the compound of claim 2 and a pharmaceutically suitable carrier.

6. A pharmaceutical composition comprising an effective amount of the compound of claim 3 and a pharmaceutically suitable carrier.

7. A method of preventing or treating verminations, bypereosinophilic syndrome (HES), eosinophilic pneumonia, eosinophilic enterogastritis and bronchial asthma comprising administering to a patient an effective amount of the pharmaceutical composition of claim 4.

8. A method of preventing or treating diseases that manifest an increase of eosinophils comprising administering to a patient an effective amount of a pharmaceutical composition that comprises a compound represented by the following formula (I) or a salt thereof:

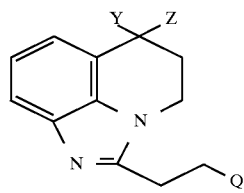

(I)

where Q represents a phenyl group that may be mono- or di-substituted with any group selected from the group consisting of a halogen atom, a nitro group, a straight or branched alkyl group having 1–4 carbon atoms that may be substituted with one or more halogen atoms, a straight or branched alkoxy group having 1–4 carbon atoms, an optionally protected hydroxyl group, an optionally protected amino group and an optionally protected carboxyl group, pyridyl group or furyl group;

Y and Z together represent an oxygen atom, and a methylene group that may be substituted with a carboxyl group or Y represents a hydrogen atom; and Z represents a hydrogen atom, a hydroxymethyl group, a carboxymethyl group, a 2-oxo-1-pyrrolidinyl group or the following formula (III):

$$—A—R^2 \qquad (III)$$

where A represents an oxygen atom, a sulfur atom or the group —NH—; $R^2$ represents a hydrogen atom, an alkyl group having 1–4 carbon atoms, an aminoalkyl group having 1–4 carbon atoms, a phenylsulfonyl group, an alkanoyl group whose alkyl group has 1–6 carbon atoms that may be mono- or di-substituted with any group selected from the group consisting of a phenyl group, an alkoxycarbonyl group whose alkyl group has 1–4 carbon atoms and an optionally protected carboxyl group, a benzoyl group that may be mono- or di-substituted with any group selected from the group consisting of a halogen atom, a nitro group, an alkyl group having 1–4 carbon atoms, an alkoxy group having 1–4 carbon atoms, an optionally protected hydroxyl group, an optionally protected carboxyl group and an optionally protected amino group, a benzyl group that may be mono- or di-substituted in the phenyl moiety with any group selected from the group consisting of a halogen atom, a nitro group, a phenyl group, a cyano group, a carbamoyl group, a hydroxymethyl group, a sulfo group, a carboxymethyl group, an alkyl group having 1–4 carbon atoms that may be substituted with one or more halogen atoms, an alkoxy group having 1–4 carbon atoms, an alkoxycarbonyl group whose alkyl group has 1–4 carbon atoms, an optionally protected hydroxyl group, an optionally protected carboxyl group and an optionally protected amino group, an alkoxyoxalyl group whose alkyl group has 1 or 2 carbon atoms, a cycloalkylcarbonyl group whose cycloalkyl group has 3–6 carbon atoms, a pyridinecarbonyl group or a thiophenecarbonyl group, and a suitable carrier.

9. The method of claim 8, wherein Q in the formula (I) represents a phenyl group, Y represents either a hydrogen atom or, when taken together with Z, an oxygen atom, Z represents a hydrogen atom or the formula (III), A and $R^2$ each have the same meaning as defined in claim 11 or a salt of said compound.

10. The method of claim 8 or 9, wherein when Y and Z in the formula (I) are a hydrogen atom and the formula (III), respectively, A represents an oxygen atom and $R^2$ represents a hydrogen atom or a benzyl group that may be mono- or di-substituted in the phenyl moiety with any group selected from the group consisting of an alkoxycarbonyl group whose alkyl group has 1–4 carbon atoms and an optionally protected carboxyl group.

* * * * *